US009498789B2

(12) United States Patent
Esaki et al.

(10) Patent No.: US 9,498,789 B2
(45) Date of Patent: Nov. 22, 2016

(54) NEBULIZER AND NEBULIZER KIT

(71) Applicant: OMRON HEALTHCARE CO., LTD., Muko-shi, Kyoto (JP)

(72) Inventors: Masayuki Esaki, Kyoto (JP); Yoichi Sasai, Kyoto (JP)

(73) Assignee: OMRON HEALTHCARE CO., LTD., Muko-Shi (JP)

(*) Notice: Subject to any disclaimer, the term of this patent is extended or adjusted under 35 U.S.C. 154(b) by 328 days.

(21) Appl. No.: 14/289,300

(22) Filed: May 28, 2014

(65) Prior Publication Data

US 2014/0263743 A1 Sep. 18, 2014

Related U.S. Application Data

(63) Continuation of application No. PCT/JP2012/076117, filed on Oct. 9, 2012.

(30) Foreign Application Priority Data

Dec. 27, 2011 (JP) ................................ 2011-285863

(51) Int. Cl.
*A61M 11/06* (2006.01)
*B05B 7/24* (2006.01)
*A61M 11/00* (2006.01)

(52) U.S. Cl.
CPC ........... *B05B 7/2491* (2013.01); *A61M 11/002* (2014.02); *A61M 11/06* (2013.01); *B05B 7/2429* (2013.01); *A61M 2206/14* (2013.01); *A61M 2209/06* (2013.01); *A61M 2209/10* (2013.01)

(58) Field of Classification Search
CPC ............. B05B 7/2491; B05B 7/2429; A61M 11/002; A61M 11/06; A61M 2206/14; A61M 2209/06; A61M 2209/10

USPC ......................... 239/338, 343, 346, 369, 370

See application file for complete search history.

(56) References Cited

U.S. PATENT DOCUMENTS 2,202,701 A * 5/1940 Lehmann ............... A61M 11/06 128/200.22
2,655,918 A * 10/1953 Jones ..................... A61M 11/06 128/200.22

(Continued)

FOREIGN PATENT DOCUMENTS

JP U-59-79140 5/1984
JP A-06-285168 10/1994

(Continued)

OTHER PUBLICATIONS

Jan. 8, 2013 International Search Report issued in International Patent Application No. PCT/JP2012/076117.

*Primary Examiner* — Justin Jonaitis
(74) *Attorney, Agent, or Firm* — Oliff PLC

(57) ABSTRACT

A nebulizer kit includes a case body having a compressed air introduction tube in an upper end portion of which is a nozzle hole that expels compressed air, a suction channel formation member forming a suction channel for sucking liquid toward the upper end portion and forming an atomizing area in an exit region of the hole, and a flow channel formation member having an aerosol discharge port. The suction channel has first and second suction channels respectively extending upward along an outer circumferential surface of the tube and from the suction channel toward the hole at a leading end area of the tube and has a liquid suction port that expels the liquid. A particle segregating portion having a blade portion, whose orientation to the atomizing area is adjustable, is between the atomizing area and the port. The suction channel formation member is fixed to the case body.

10 Claims, 37 Drawing Sheets

(56) References Cited

U.S. PATENT DOCUMENTS 5,054,477 A * 10/1991 Terada .................. A61M 11/06
128/200.14
5,687,912 A * 11/1997 Denyer .................. A61M 11/06
128/200.21

FOREIGN PATENT DOCUMENTS

| JP | A-2000-217916 | 8/2000 |
| JP | A-2003-079731 | 3/2003 |
| JP | A-2006-206976 | 8/2006 |

* cited by examiner

NEBULIZER AND NEBULIZER KIT

This is a Continuation of International Application No. PCT/JP2012/076117 filed Oct. 9, 2012, which claims the benefit of Japanese Patent Application No. 2011-285863 filed Dec. 27, 2011. The disclosure of the prior applications is hereby incorporated by reference herein in its entirety.

TECHNICAL FIELD

The present invention relates to nebulizers and nebulizer kits.

BACKGROUND ART

Nebulizers produce aerosol by atomizing water, saline solutions, drug solutions for treating diseases in the respiratory system or the like, or liquids such as vaccines. A typical nebulizer includes a nebulizer kit that produces the aerosol. JP H6-285168A (Patent Literature 1) can be given as an example of a background art document disclosing a nebulizer kit.

A typical nebulizer kit 1000Z will be described hereinafter with reference to FIG. 60. FIG. 60 is a cross-sectional view illustrating the nebulizer kit 1000Z. The nebulizer kit 1000Z includes a case body 900, an atomizing area formation member 920, a flow channel formation member 930, and an atomizing area M.

Case Body 900

The case body 900 is formed as a closed-ended cylinder. An upper opening 902 is provided in an upper area of the case body 900. A compressed air introduction tube 913 and a liquid reservoir portion 916 are provided within the case body 900. The compressed air introduction tube 913 extends upward from a base of the case body 900 (that is, from the side on which the liquid reservoir portion 916 is located). Compressed air (not shown) is introduced into the compressed air introduction tube 913.

A nozzle hole 915 for ejecting the compressed air is provided in an upper tip area 913a of the compressed air introduction tube 913. The liquid reservoir portion 916, which serves to hold a liquid W, is provided so as to surround an outer circumferential surface of the compressed air introduction tube 913 on a lower end of the compressed air introduction tube 913.

Atomizing Area Formation Member 920

The atomizing area formation member 920 includes a liquid suction tube formation area 924, a baffle portion 922, and a baffle support portion 923. The liquid suction tube formation area 924 is formed as a cylinder. The diameter of the liquid suction tube formation area 924 decreases as the liquid suction tube formation area 924 progresses upward. An opening 924a is provided at the apex of the liquid suction tube formation area 924. The baffle portion 922 has a projection 925 located immediately above the opening 924a. The projection 925 is provided as necessary.

The baffle support portion 923 extends toward a side area of the baffle portion 922 from an outside surface of the liquid suction tube formation area 924. The baffle portion 922 and the projection 925 face the opening 924a with a gap provided therebetween. The atomizing area formation member 920 is contained and disposed within the case body 900 so that an outer surface of the compressed air introduction tube 913 is covered by the liquid suction tube formation area 924.

Flow Channel Formation Member 930

The flow channel formation member 930 is attached to the case body 900 so as to cap an upper opening 902 in the case body 900. The flow channel formation member 930 includes an aerosol discharge port 932 and an outside air introduction tube 934. The aerosol discharge port 932 is provided in an upper area of the flow channel formation member 930. Aerosol produced within the case body 900 (at the atomizing area M) is discharged to the exterior from the aerosol discharge port 932. The outside air introduction tube 934 is provided so as to pass through the flow channel formation member 930 from top to bottom. Outside air used to produce the aerosol is introduced through the outside air introduction tube 934, from the exterior of the case body 900 toward the interior of the case body 900 (the atomizing area M).

Atomizing Area M

FIG. 61 is a cross-sectional view illustrating the atomizing area M in the nebulizer kit 1000Z in an enlarged manner. The atomizing area M is formed between the baffle portion 922 (the projection 925) provided in the atomizing area formation member 920 and the nozzle hole 915 provided in the compressed air introduction tube 913 (see FIG. 60).

The compressed air introduced into the compressed air introduction tube 913 is expelled through the nozzle hole 915 provided in the upper tip area 913a (see an arrow AR913). After being expelled from the nozzle hole 915 toward the projection 925, the compressed air collides with the projection 925 and the baffle portion 922, changes direction, and spreads out radially (see an arrow AR922). A negative pressure, where the pressure is lower than the surroundings, is produced at the atomizing area M and the vicinity thereof.

The liquid W is sucked upward to the vicinity of the atomizing area M from the liquid reservoir portion 916 due to the negative pressure produced at the atomizing area M and the vicinity thereof (see an arrow AR915). The liquid W collides with the compressed air flowing in the direction of the arrow AR922 and breaks up as a result, changing into mist particles (fine droplets) (not shown).

These mist particles attach to the outside air introduced into the case body 900 through the outside air introduction tube 934 (see an arrow AR934). The aerosol is produced at the atomizing area M. The aerosol swirls (see an arrow AR932) toward the aerosol discharge port 932 (see FIG. 60) and is discharged to the exterior through the aerosol discharge port 932 (see FIG. 60).

CITATION LIST

Patent Literature

Patent Literature 1: JP H6-285168A

SUMMARY OF INVENTION

Technical Problem

FIG. 62 is a cross-sectional view illustrating the atomizing area M in the nebulizer kit 1000Z in a further enlarged manner. As described above, the compressed air expelled through the nozzle hole 915 (see the arrow AR913) collides with a lower end 925T of the projection 925 and the baffle portion 922 (see FIG. 61). The compressed air that has collided with the lower end 925T of the projection 925 and so on changes direction and spreads radially (see the arrow AR922).

After breaking up the liquid W through air pressure (wind pressure), the compressed air collides with an inner circumferential surface of the baffle support portion 923 (see FIG. 61) or the outside air introduction tube 934 (see FIG. 61).

The compressed air that has turned into aerosol swirls (see the arrow AR932 in FIG. 61) toward the aerosol discharge port 932 (see FIG. 60) and is discharged to the exterior through the aerosol discharge port 932 (see FIG. 60).

When the aerosol is produced in the nebulizer kit 1000Z, the compressed air expelled from the nozzle hole 915 first collides with the projection 925 (an/or the baffle portion 922), then collides with the baffle support portion 923 (see FIG. 61), and finally collides with the inner circumferential surface of the outside air introduction tube 934 (see FIG. 61). The compressed air expelled from the nozzle hole 915 loses pressure with each of these collisions.

For the compressed air introduced into the compressed air introduction tube 913, it is necessary to prepare compressed air that has the pressure required to produce the aerosol while also taking into consideration such a loss in pressure. Accordingly, in conventional nebulizer kits such as the nebulizer kit 1000Z, it has been necessary to use a high-capacity (high-flow rate) and large-size compressor or the like in order to generate compressed air having a high flow rate.

Having been achieved in light of the aforementioned circumstances, it is an object of the present invention to provide a nebulizer kit and a nebulizer capable of reducing pressure loss in compressed air when producing aerosol.

Solution to Problem

A nebulizer kit according to the present invention includes: a case body, having an open upper end, and including a compressed air introduction tube, extending upward, into which compressed air is introduced and in an upper end portion of which a nozzle hole that expels the compressed air is formed, and further including a liquid reservoir portion provided surrounding an outer circumferential surface of the compressed air introduction tube at a bottom area of the compressed air introduction tube; a suction channel formation member that forms a suction channel that sucks a liquid held in the liquid reservoir portion toward the upper end portion of the compressed air introduction tube and forms an atomizing area in an exit region of the nozzle hole provided in the compressed air introduction tube by covering the outer circumferential surface of the compressed air introduction tube; and a flow channel formation member, including an aerosol discharge port that discharges an aerosol formed at the atomizing area to the exterior, that is attached to the case body so as to cover an upper opening of the case body. Here, the suction channel includes a first suction channel that extends upward along the outer circumferential surface of the compressed air introduction tube and a second suction channel that extends from the first suction channel toward the nozzle hole at a leading end area of the compressed air introduction tube and has a liquid suction port that expels the liquid that has been sucked up; a particle segregating portion that has a blade portion and that segregates particles of the aerosol using the blade portion and discharges the aerosol of a desired particle size to the exterior is provided between the atomizing area and the aerosol discharge port; the suction channel formation member is fixed to the case body; an orientation or a position of the blade portion relative to the atomizing area can be adjusted; and the position of the blade portion relative to the atomizing area is adjusted by moving the blade portion so as to increase or decrease a gap between the blade portion and the atomizing area.

Preferably, the orientation of the blade portion relative to the atomizing area is adjusted by rotating the blade portion.

Preferably, the blade portion is configured to occupy a space between the atomizing area and the aerosol discharge port in a fan shape.

Preferably, the blade portion is configured to occupy a space between the atomizing area and the aerosol discharge port in a linear shape.

Preferably, the blade portion is configured to be removable from the flow channel formation member.

Preferably, the blade portion is provided toward an end of the particle segregating portion in the lengthwise direction of the particle segregating portion.

Preferably, the particle segregating portion is configured to be removable from the flow channel formation member.

Preferably, the flow channel formation member includes an upper cylinder portion having the aerosol discharge port, and the blade portion and the particle segregating portion are assembled with the upper cylinder portion.

Preferably, a channel through which the aerosol flows between the atomizing area and the aerosol discharge port is configured to have a smaller inner diameter in an area near the aerosol discharge port than in an area near the atomizing area.

A nebulizer according to the present invention includes: a main body including a compressor that discharges compressed air; a compressed air tube portion through which the compressed air discharged by the compressor is introduced; and the aforementioned nebulizer kit according to the present invention, to which one end of the compressed air tube portion is attached and that produces an aerosol.

Advantageous Effects of Invention

According to the present invention, a nebulizer kit and a nebulizer capable of reducing a loss of pressure in compressed air when producing aerosol can be provided.

FIG. 38 is a cross-sectional perspective view illustrating the particle segregating portion used in the nebulizer kit according to the sixteenth embodiment.

FIG. 39 is an exploded perspective view illustrating a particle segregating portion and a flow channel formation member used in a nebulizer kit according to a seventeenth embodiment.

FIG. 40 is a cross-sectional view taken along a XL-XL line shown in FIG. 39.

FIG. 41 is an exploded perspective view illustrating a particle segregating portion and a flow channel formation member used in a nebulizer kit according to an eighteenth embodiment.

FIG. 42 is an exploded perspective view illustrating a particle segregating portion and a flow channel formation member used in a nebulizer kit according to a nineteenth embodiment.

FIG. 43 is an exploded perspective view illustrating a particle segregating portion and a flow channel formation member used in a nebulizer kit according to a twentieth embodiment.

FIG. 44 is an exploded perspective view illustrating a particle segregating portion and a flow channel formation member used in a nebulizer kit according to a twenty-first embodiment.

FIG. 45 is a perspective view illustrating a nebulizer kit according to a twenty-second embodiment.

FIG. 46 is an exploded perspective view illustrating the nebulizer kit according to the twenty-second embodiment.

FIG. 47 is a cross-sectional perspective view illustrating a case body and a suction channel formation member used in the nebulizer kit according to the twenty-second embodiment.

FIG. 48 is a perspective view illustrating an upper cylinder portion of a flow channel formation member used in the nebulizer kit according to the twenty-second embodiment.

FIG. 49 is a cross-sectional perspective view illustrating a state when a particle segregating portion used in the nebulizer kit according to the twenty-second embodiment is fixed to the upper cylinder portion of the flow channel formation member.

FIG. 50 is a cross-sectional perspective view illustrating a state when a particle segregating portion used in the nebulizer kit according to the twenty-second embodiment is fixed to a lower cylinder portion of the flow channel formation member.

FIG. 51 is a perspective view illustrating operations of the nebulizer kit according to the twenty-second embodiment.

FIG. 52 is a first plan view illustrating the particle segregating portion and the flow channel formation member used in the nebulizer kit according to the twenty-second embodiment.

FIG. 53 is a second plan view illustrating the particle segregating portion and the flow channel formation member used in the nebulizer kit according to the twenty-second embodiment.

Figure 54:
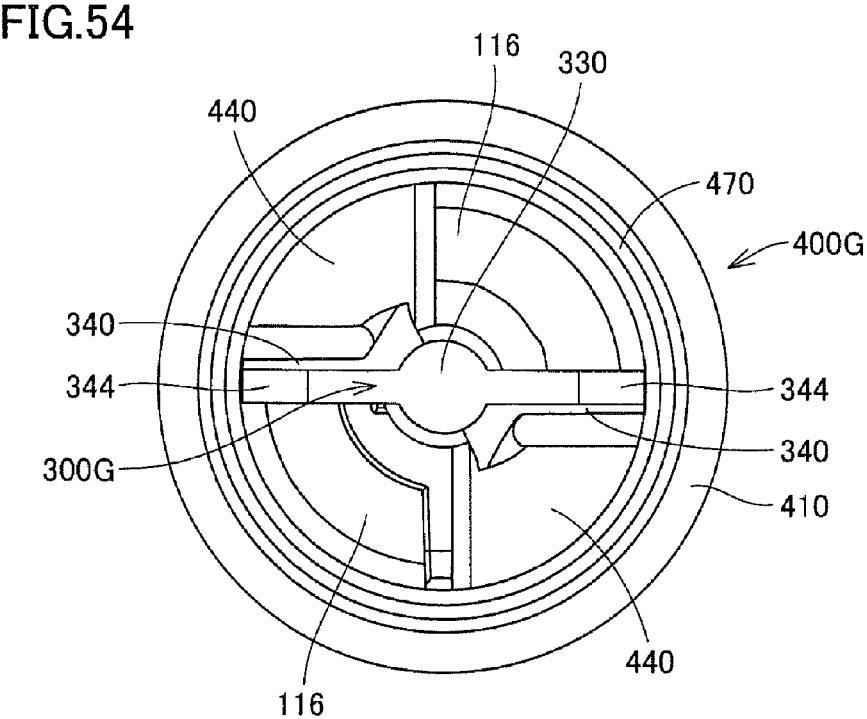

FIG. 54 is a third plan view illustrating the particle segregating portion and the flow channel formation member used in the nebulizer kit according to the twenty-second embodiment.

Figure 55:
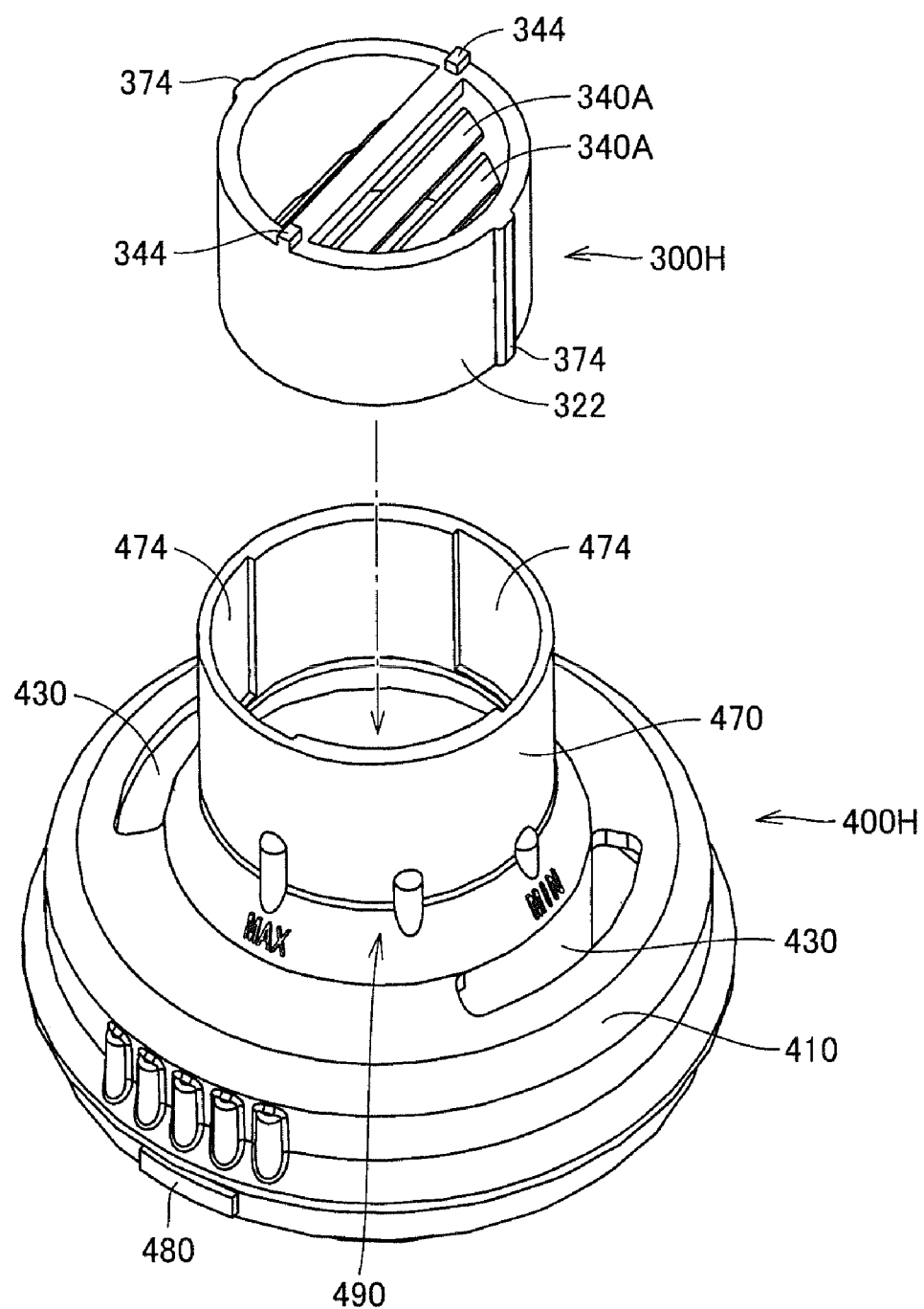

FIG. 55 is an exploded perspective view illustrating a particle segregating portion and a flow channel formation member used in a nebulizer kit according to a twenty-third embodiment.

Figure 56:
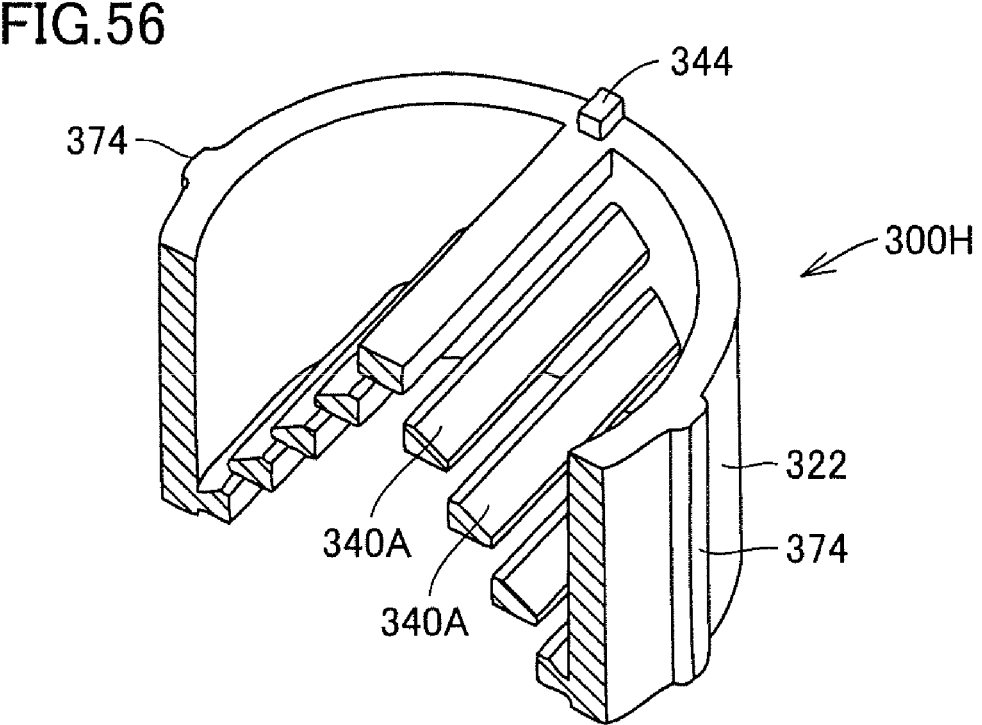

FIG. 56 is a cross-sectional perspective view illustrating the particle segregating portion used in the nebulizer kit according to the twenty-third embodiment.

Figure 57:
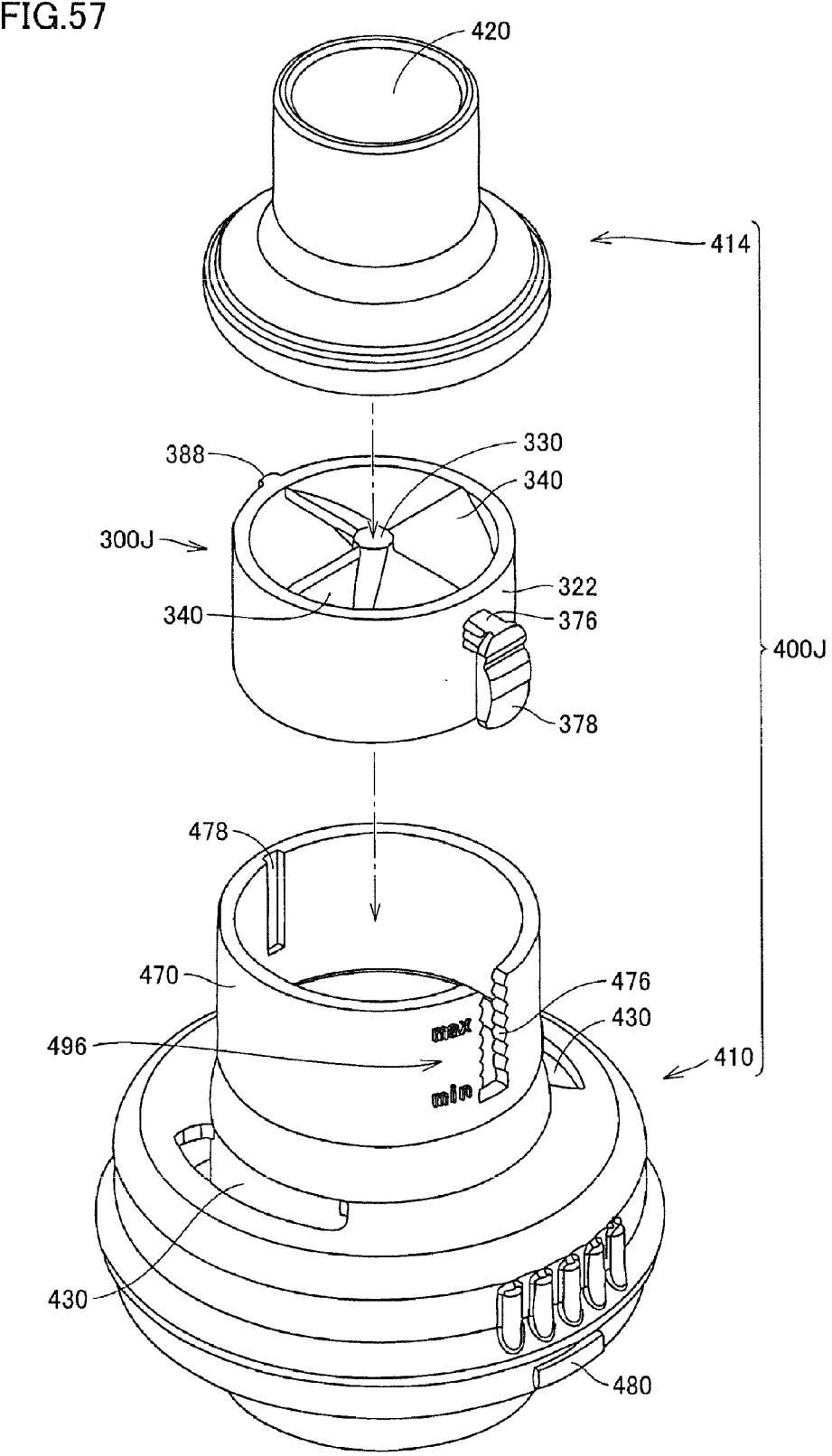

FIG. 57 is an exploded perspective view illustrating a particle segregating portion and a flow channel formation member used in a nebulizer kit according to a twenty-fourth embodiment.

Figure 58:
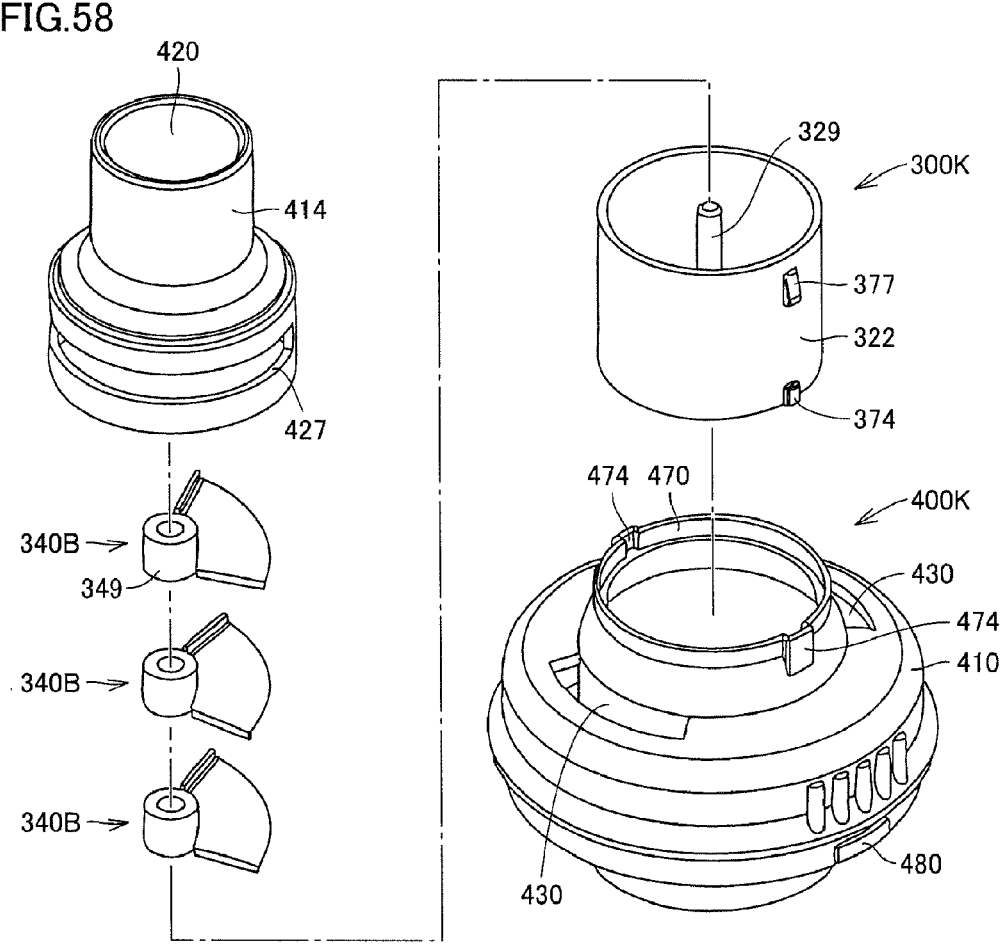

FIG. 58 is an exploded perspective view illustrating a particle segregating portion and a flow channel formation member used in a nebulizer kit according to a twenty-fifth embodiment.

Figure 59:
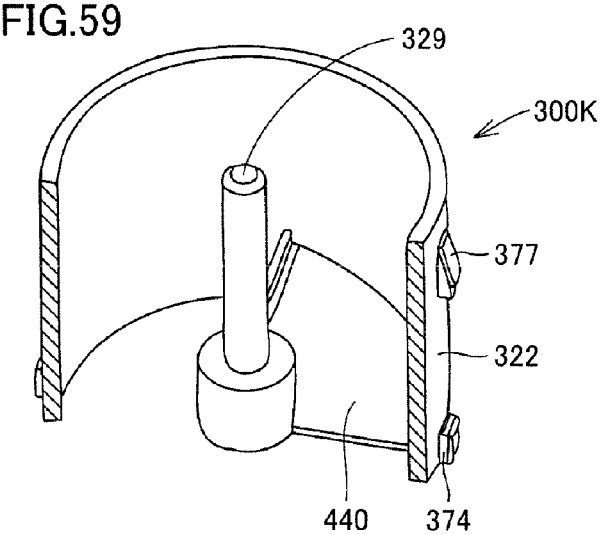

FIG. 59 is a cross-sectional perspective view illustrating the particle segregating portion used in the nebulizer kit according to the twenty-fifth embodiment.

Figure 60:
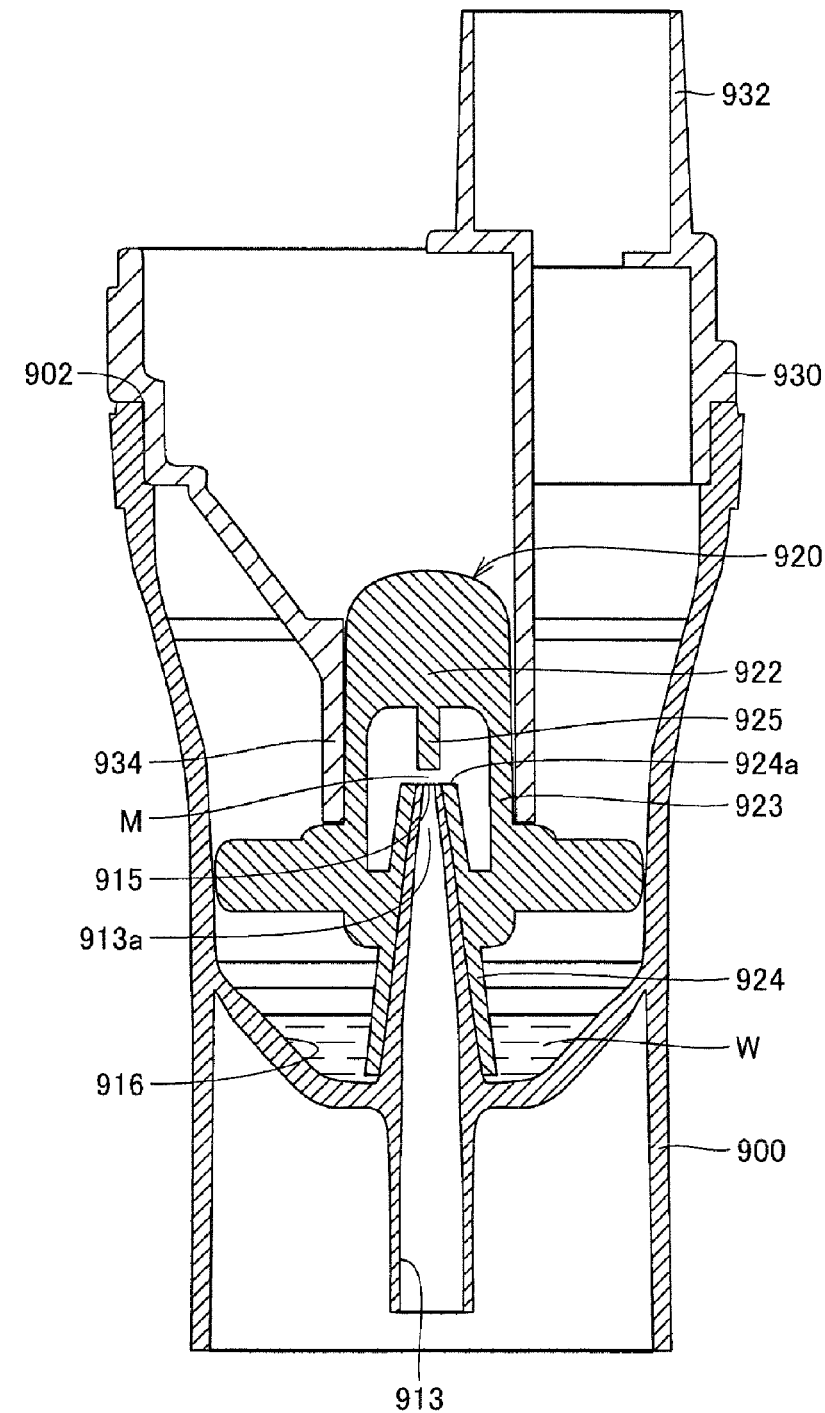

FIG. 60 is a cross-sectional view illustrating a typical nebulizer kit.

Figure 61:
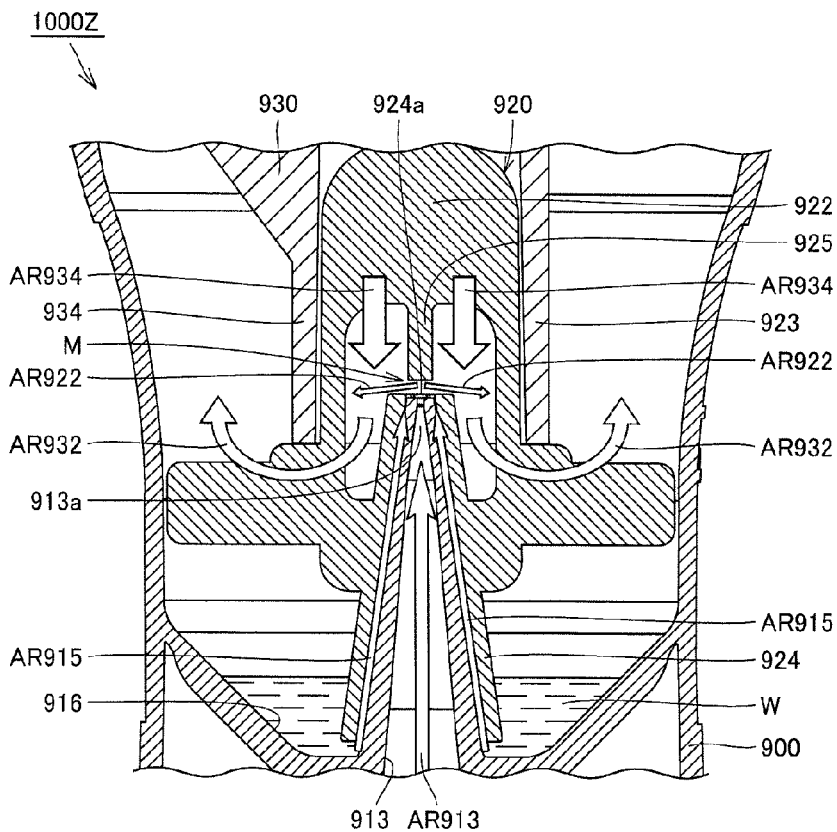

FIG. 61 is a cross-sectional view illustrating an atomizing area of a typical nebulizer kit in an enlarged manner.

Figure 62:
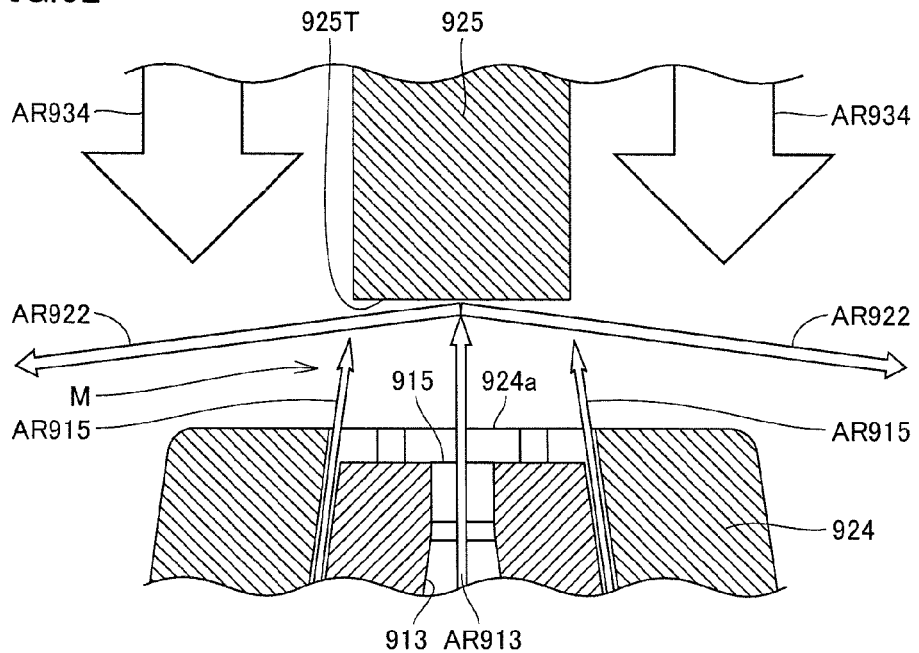

FIG. 62 is a cross-sectional view illustrating the atomizing area of a typical nebulizer kit in a further enlarged manner.

DESCRIPTION OF EMBODIMENTS

Several embodiments based on the present invention will be described hereinafter with reference to the drawings. When numbers, amounts, and so on are discussed in the following embodiments, unless explicitly mentioned otherwise, the scope of the present invention is not necessarily limited to those numbers, amounts, and so on. In the embodiments, identical and corresponding components may be assigned identical reference numerals, and redundant descriptions thereof may be omitted. Unless otherwise specified, it is assumed from the outset that the configurations described in the respective embodiments are used in combination with each other as appropriate.

First Embodiment

Nebulizer 2000

Figure 1:
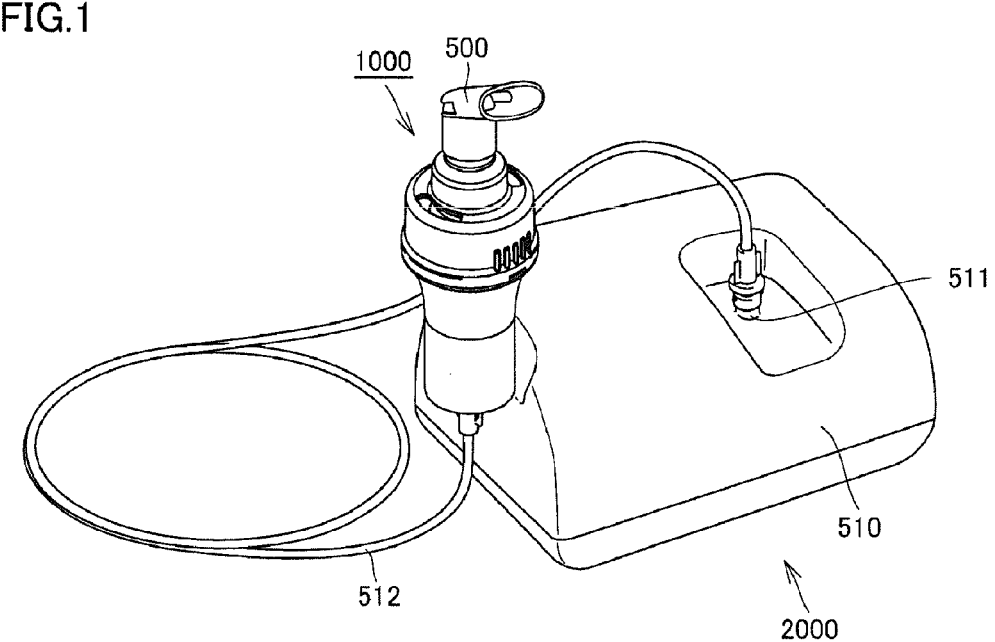
FIG. 1 is a perspective view illustrating a nebulizer according to a first embodiment.

A nebulizer 2000 according to the present embodiment will be described with reference to FIG. 1. The nebulizer 2000 includes a main body 510, a tube 512 (a compressed air tube portion), a nebulizer kit 1000, and a mouthpiece 500. The main body 510 includes a compressor that discharges compressed air, electrical components, and so on. The tube 512 is flexible. One end of the tube 512 is connected to a compressed air expulsion port 511 provided in the main body 510. The other end of the tube 512 is connected to the nebulizer kit 1000.

Figure 2:
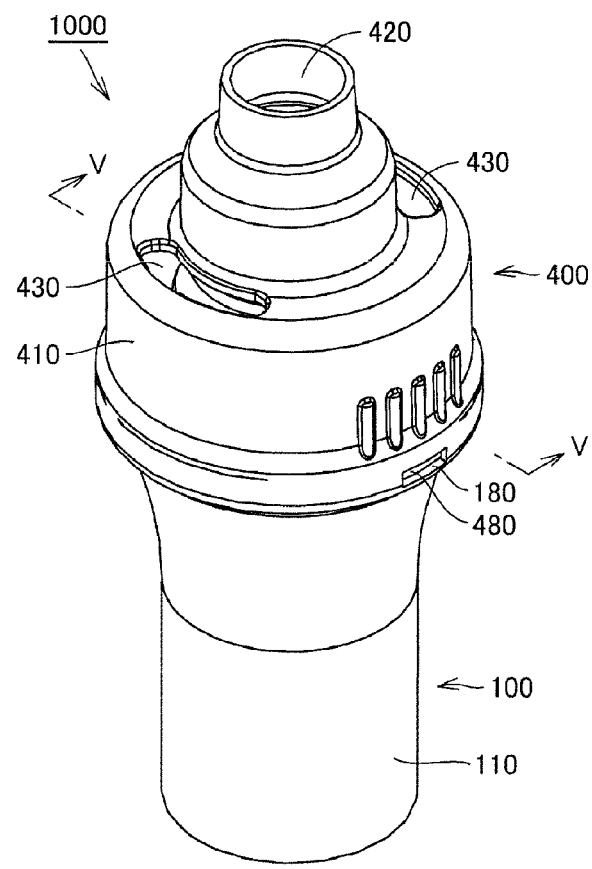
FIG. 2 is a perspective view illustrating a nebulizer kit according to the first embodiment.

The mouthpiece 500 is attached to an aerosol discharge port 420 (see FIG. 2) of the nebulizer kit 1000. The mouthpiece 500 is used by a user to suck aerosol into his/her nose or mouth. The mouthpiece 500 is formed in a tube shape such as that shown in FIG. 1. The mouthpiece 500 may instead be formed in a mask shape. The mouthpiece 500 is a disposable type that for sanitary purposes is discarded after use.

When the nebulizer kit 1000 is used, the nebulizer kit 1000 is held by the user so that a lengthwise direction of the nebulizer kit 1000 is approximately parallel to the vertical direction, as shown in FIG. 1. An "upward" and a "downward" direction of the nebulizer kit 1000 respectively correspond to upward in the vertical direction and downward in the vertical direction relative to the nebulizer kit 1000 when used in this state (a reference orientation employed when the nebulizer kit 1000 is used).

Nebulizer Kit 1000

FIG. 2 is perspective view illustrating the nebulizer kit 1000. FIG. 3 is an exploded perspective view illustrating the nebulizer kit 1000. FIG. 4 is an exploded cross-sectional view illustrating the nebulizer kit 1000. FIG. 5 is a cross-sectional view taken along a V-V line shown in FIG. 2. As shown in FIGS. 2 to 5, the nebulizer kit 1000 includes a case body 100, a suction channel formation member 200 (see FIGS. 3 to 5), a particle segregating portion 300 (see FIGS. 3 to 5), and a flow channel formation member 400.

Case Body 100

Referring primarily to FIG. 4, the case body 100 includes a cylinder portion 110, an opening 102 (an upper opening), a compressed air introduction tube 113, and a liquid reservoir portion 116, and is configured as a closed-ended cylinder overall. A lower end of the cylinder portion 110 is closed off by the liquid reservoir portion 116, whereas an upper end of the cylinder portion 110 is left open by the opening 102 provided therein. Interlocking holes 180 are provided in the vicinity of the opening 102 in the cylinder portion 110. When the flow channel formation member 400 is attached to the case body 100, the interlocking holes 180 interlock with corresponding interlocking protrusions 480 provided in the flow channel formation member 400 (see FIGS. 2, 3, and 5).

The compressed air introduction tube 113 extends in a tapered form, decreasing in diameter as the compressed air introduction tube 113 progresses upward from the lower-center of the cylinder portion 110. A nozzle hole 115 is provided in an upper tip area 113*a* of the compressed air introduction tube 113. The nozzle hole 115 passes through the approximate center of a leading end surface 113*s* of the upper tip area 113*a*.

The tube 512 (see FIG. 1) is attached to a lower leading end area of the compressed air introduction tube 113. The compressor provided in the main body 510 of the nebulizer 2000 (see FIG. 1) introduces compressed air into the compressed air introduction tube 113 through the compressed air expulsion port 511 (see FIG. 1) and the tube 512 (see FIG. 1). The compressed air introduced into the compressed air introduction tube 113 is ejected toward the interior of the case body 100 from the nozzle hole 115.

The liquid reservoir portion 116 is provided so as to surround an outer circumferential surface 113*b* of the compressed air introduction tube 113 on a lower end of the compressed air introduction tube 113. The liquid reservoir portion 116 temporarily holds a liquid W such as water, a saline solution, a drug solution for treating respiratory system conditions or the like, a vaccine, or the like.

Suction Channel Formation Member 200

FIG. 6 is a first perspective view illustrating the suction channel formation member 200, and illustrates the overall configuration of the suction channel formation member 200 from above at an angle. FIG. 7 is a cross-sectional perspective view taken along a VII-VII line shown in FIG. 6, and is a first cross-sectional perspective view illustrating the suction channel formation member 200. FIG. 7 illustrates the internal structure of the suction channel formation member

Figure 8:
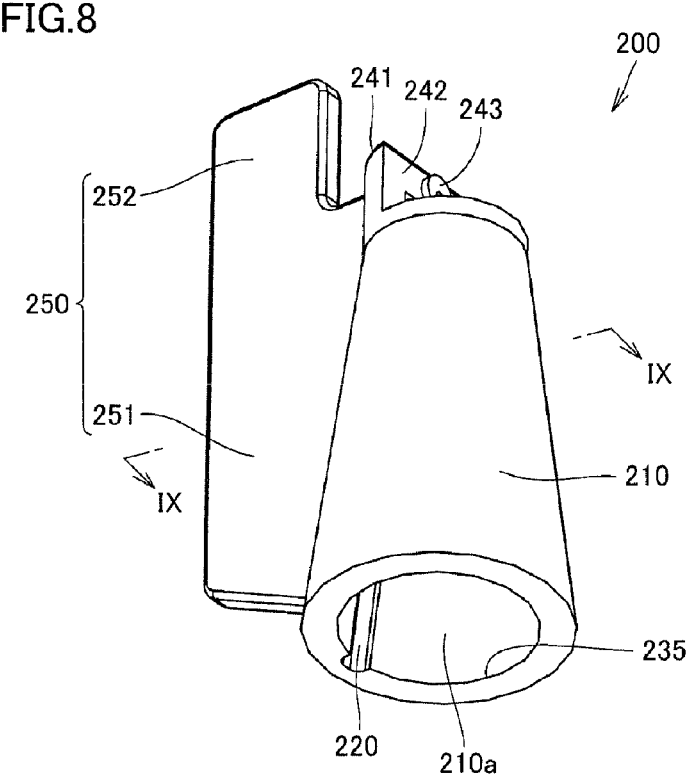
FIG. 8 is a second perspective view illustrating the suction channel formation member used in the nebulizer kit according to the first embodiment.
Figure 9:
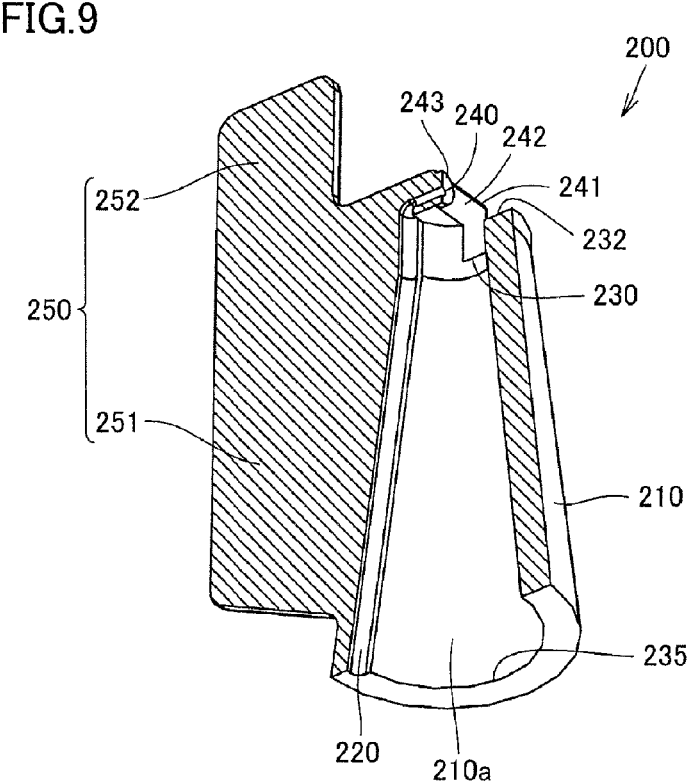
FIG. 9 is a cross-sectional perspective view taken along a IX-IX line shown in FIG. 8, and is a second cross-sectional perspective view illustrating the suction channel formation member used in the nebulizer kit according to the first embodiment.

200 from above at an angle. FIG. 8 is a second perspective view illustrating the suction channel formation member 200, and illustrates the overall configuration of the suction channel formation member 200 from below at an angle. FIG. 9 is a cross-sectional perspective view taken along a IX-IX line shown in FIG. 8, and is a second cross-sectional view illustrating the suction channel formation member 200. FIG. 9 illustrates the internal structure of the suction channel formation member 200 from below at an angle.

As shown in FIGS. 6 to 9, the suction channel formation member 200 includes a cylinder portion 210, a suction channel formation portion 220 (see FIGS. 7 to 9), an opening 230 (see FIGS. 6 and 7), an opening 235 (see FIGS. 8 and 9), a liquid suction port 240, and a plate-shaped gripping portion 250.

The cylinder portion 210 is formed as a circular cylinder in a tapered shape, with the diameter thereof decreasing as the cylinder portion 210 progresses upward. The opening 230 is formed in an apex of the cylinder portion 210. The opening 235 is formed in a base area of the cylinder portion 210. The shape of an inner circumferential surface 210*a* of the cylinder portion 210 corresponds to the shape of the outer circumferential surface 113*b* of the compressed air introduction tube 113 provided in the case body 100 (see FIG. 5).

An expanded portion 241 formed in a half-circular column shape is provided on an upper end surface 232 of the cylinder portion 210. A liquid suction port formation member 243 that projects in a circular column shape is provided in an end surface 242 of the expanded portion 241. The liquid suction port formation member 243 projects in a direction perpendicular relative to the end surface 242. The plate-shaped gripping portion 250 is provided so as to extend outward in the normal direction of the cylinder portion 210 from an outer surface of the cylinder portion 210. The plate-shaped gripping portion 250 includes a plate portion 251 and a protrusion 252. The protrusion 252 is provided above the plate portion 251 as an integral part of the plate portion 251, and projects further upward than the surface of the apex of the expanded portion 241.

The suction channel formation portion 220 is formed having an overall approximate L shape. The suction channel formation portion 220 is provided in the inner circumferential surface 210*a* of the cylinder portion 210 as an indentation that extends approximately linearly from the opening 235 toward the opening 230, and is provided so as to pass through the interior of the expanded portion 241 and the liquid suction port formation member 243.

A leading end in the extension direction of the suction channel formation portion 220 that passes through the liquid suction port formation member 243 reaches the surface of the liquid suction port formation member 243. The liquid suction port 240 is formed in a leading end portion of the suction channel formation portion 220 that reaches the surface of the liquid suction port formation member 243. The diameter of the liquid suction port 240 is no less than 0.45 mm and no more than 0.5 mm, for example.

Figure 10:
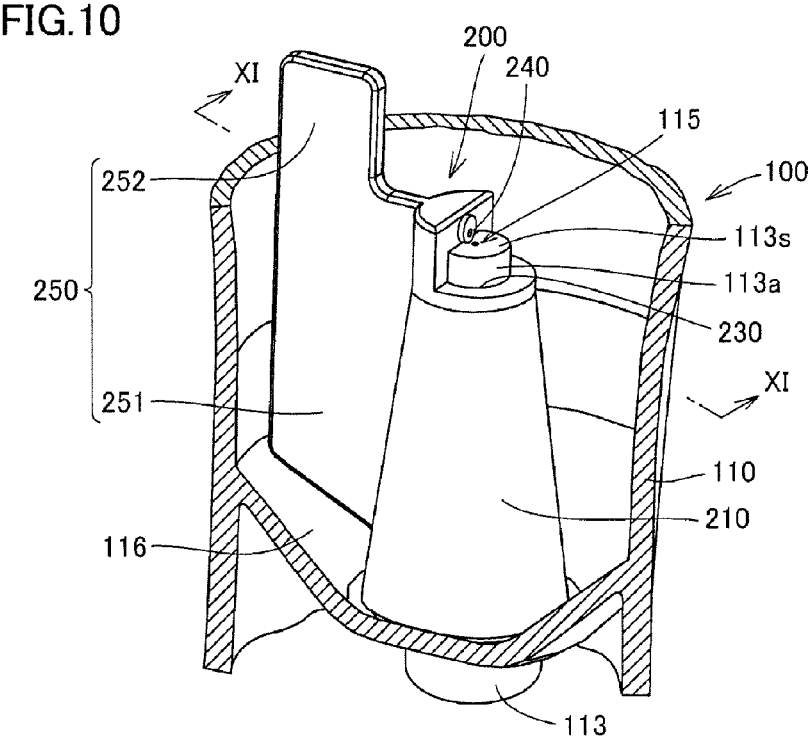
FIG. 10 is a cross-sectional perspective view illustrating the suction channel formation member used in the nebulizer kit according to the first embodiment, contained and disposed within a case body.
Figure 11:
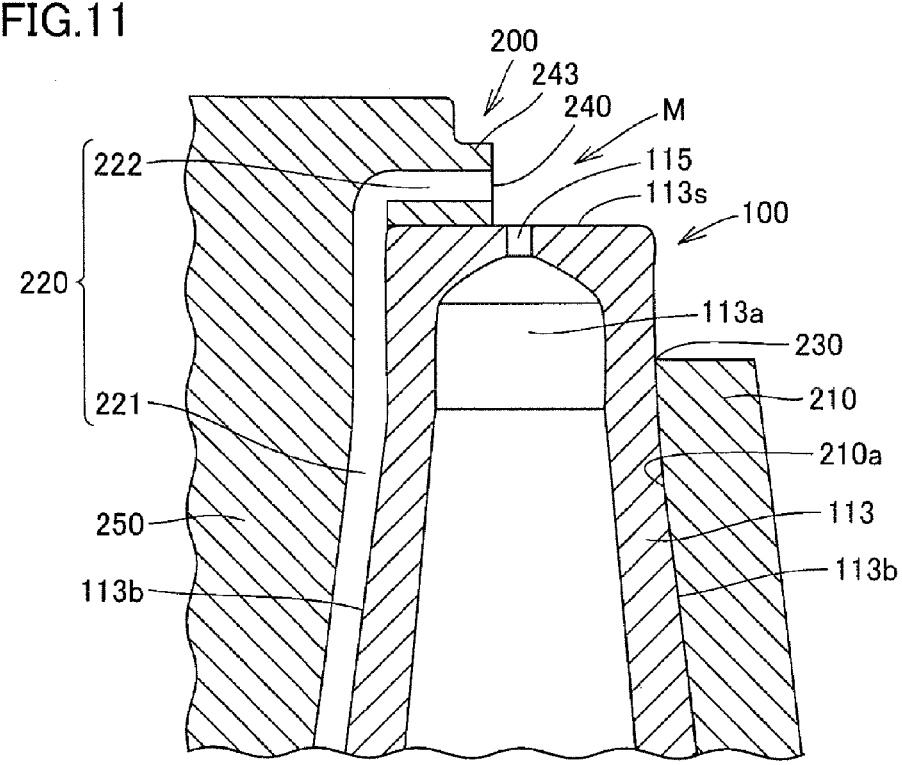
FIG. 11 is a cross-sectional view taken along a XI-XI line shown in FIG. 10.

FIG. 10 is a cross-sectional perspective view illustrating a state in which the suction channel formation member 200 is contained and disposed within the case body 100. FIG. 11 is a cross-sectional view taken along a XI-XI line shown in FIG. 10.

As shown in FIGS. 10 and 11, the suction channel formation member 200 is contained and disposed within the case body 100 so that the outer circumferential surface 113*b* of the compressed air introduction tube 113 is covered by the cylinder portion 210. When the suction channel formation member 200 is contained and disposed within the case body 100, the upper tip area 113*a* of the compressed air introduction tube 113 is exposed from the opening 230 in the suction channel formation member 200.

As shown in FIG. 11, the nozzle hole 115 and the liquid suction port 240 are provided so that a center line of the nozzle hole 115 and a center line of the liquid suction port 240 are approximately orthogonal to each other. The inner circumferential surface 210*a* of the cylinder portion 210 and the outer circumferential surface 113*b* of the compressed air introduction tube 113 are essentially in tight contact with each other, aside from an area of the inner circumferential surface 210*a* of the cylinder portion 210 where the suction channel formation portion 220 is provided.

A suction channel 221 (a first suction channel) is formed between the suction channel formation portion 220 and the outer circumferential surface 113*b* of the compressed air introduction tube 113. The suction channel 221 extends upward, from the side on which the liquid reservoir portion 116 is located (see FIG. 10) toward the nozzle hole 115, along the outer circumferential surface 113*b* of the compressed air introduction tube 113.

A suction channel 222 (a second suction channel) is formed so as to connect with an upper end of the suction channel 221. In the present embodiment, the suction channel 222 extends in a direction orthogonal to the upper end of the suction channel 221. At the leading end of the compressed air introduction tube 113, the suction channel 222 extends from the upper end of the suction channel 221 toward the nozzle hole 115, approximately orthogonally to the direction of a center axis of the nozzle hole 115. The liquid suction port 240 is formed in a leading end area of the suction channel 222. In the present embodiment, the liquid suction port 240 does not overlap with the nozzle hole 115, and is instead disposed slightly back from the nozzle hole 115.

Particle Segregating Portion 300

Figure 12:
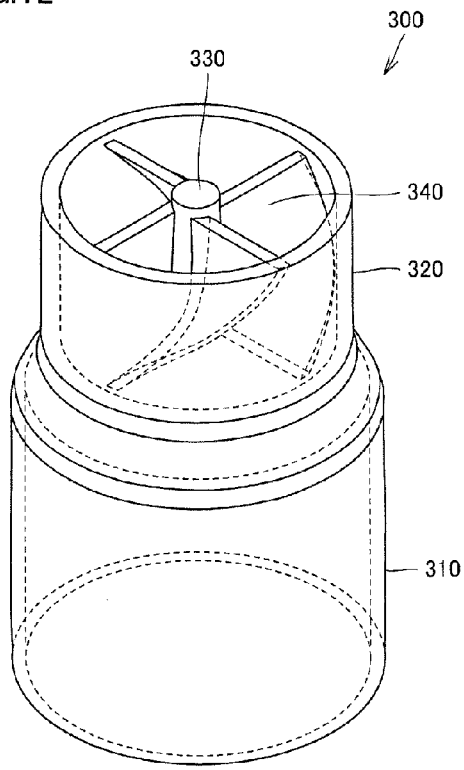
FIG. 12 is a perspective view illustrating a particle segregating portion used in the nebulizer kit according to the first embodiment.

FIG. 12 is a perspective view illustrating the particle segregating portion 300. The particle segregating portion 300 is generally configured in an approximately cylindrical shape that extends upward from below while decreasing in diameter. The particle segregating portion 300 includes a lower cylinder portion 310, an upper cylinder portion 320, a center shaft portion 330, and four blade portions 340. The lower cylinder portion 310 is disposed coaxially with the upper cylinder portion 320. The diameter of the lower cylinder portion 310 is greater than the diameter of the upper cylinder portion 320.

The four blade portions 340 are provided between the center shaft portion 330, which is located in the center of the upper cylinder portion 320, and the inner circumferential surface of the upper cylinder portion 320. The four blade portions 340 are formed having essentially the same plate shape. The four blade portions 340 are disposed so as to be separated from each other by 90°. The four blade portions 340 curve in a twisting manner from a lower area of the upper cylinder portion 320 toward an upper area of the upper cylinder portion 320. The four blade portions 340 are disposed in an overall screw shape. The four blade portions 340 occupy a space between the atomizing area M and the aerosol discharge port 420 in a fan shape.

Figure 4:
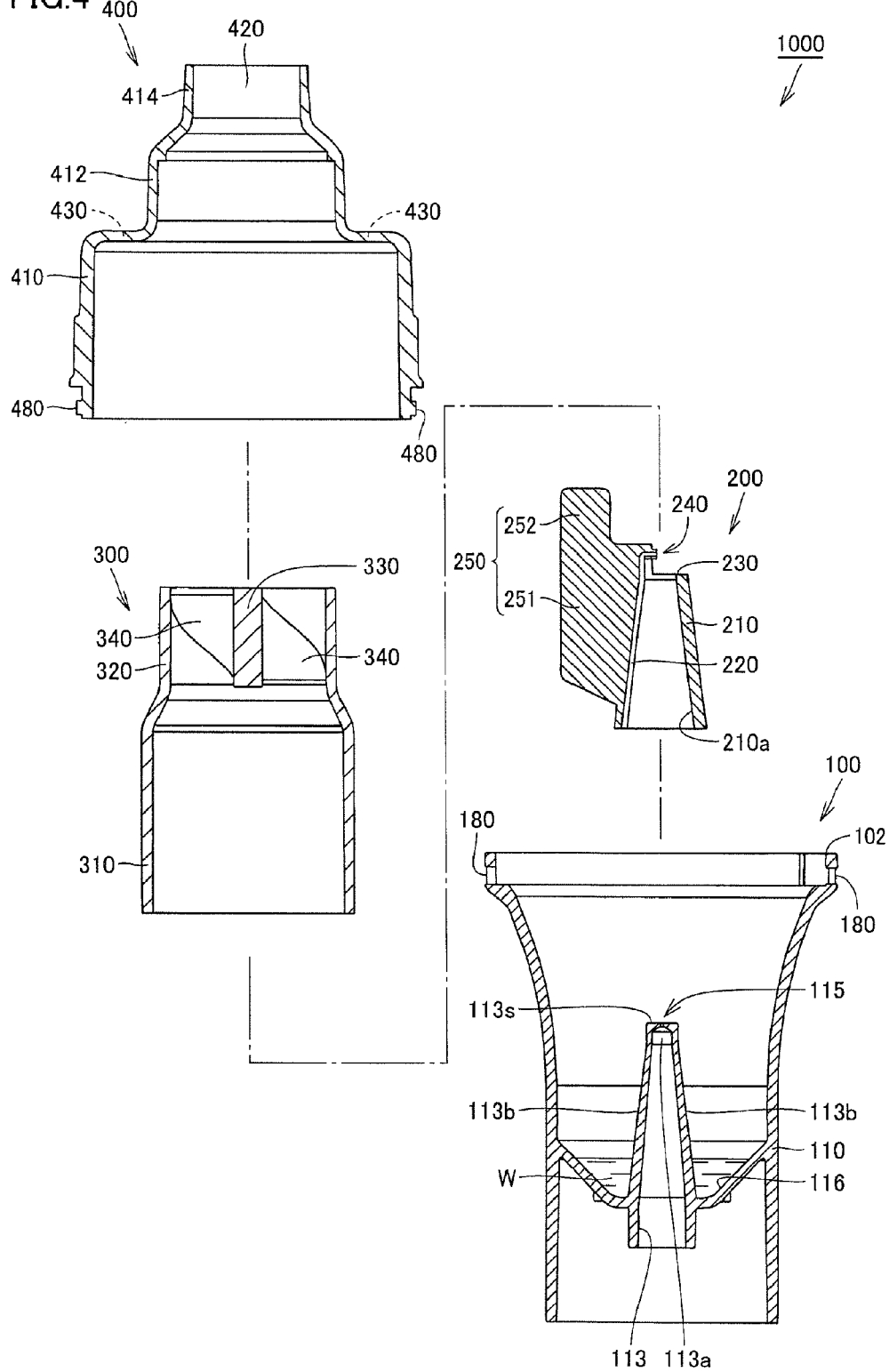
FIG. 4 is an exploded cross-sectional view illustrating the nebulizer kit according to the first embodiment.

Referring again to FIGS. 4 and 5, the particle segregating portion 300 is disposed above the suction channel formation member 200 that is in turn disposed within the case body 100. A lower end of the particle segregating portion 300 makes contact with an upper end of the protrusion 252 of the suction channel formation member 200. The upper cylinder portion 320 of the particle segregating portion 300 is fixed to an inner side of a central cylinder portion 412 of the flow channel formation member 400, which will be described next (see FIG. 5).

Fixing the flow channel formation member 400 to the case body 100 positions the particle segregating portion 300. The suction channel formation member 200 is fixed to the case body 100 as a result of the lower end of the positioned particle segregating portion 300 and the upper end of the protrusion 252 of the suction channel formation member 200 making contact with each other. Vertical movement of the suction channel formation member 200 relative to the case body 100 is limited as a result of this fixing.

Flow Channel Formation Member 400

Figure 3:
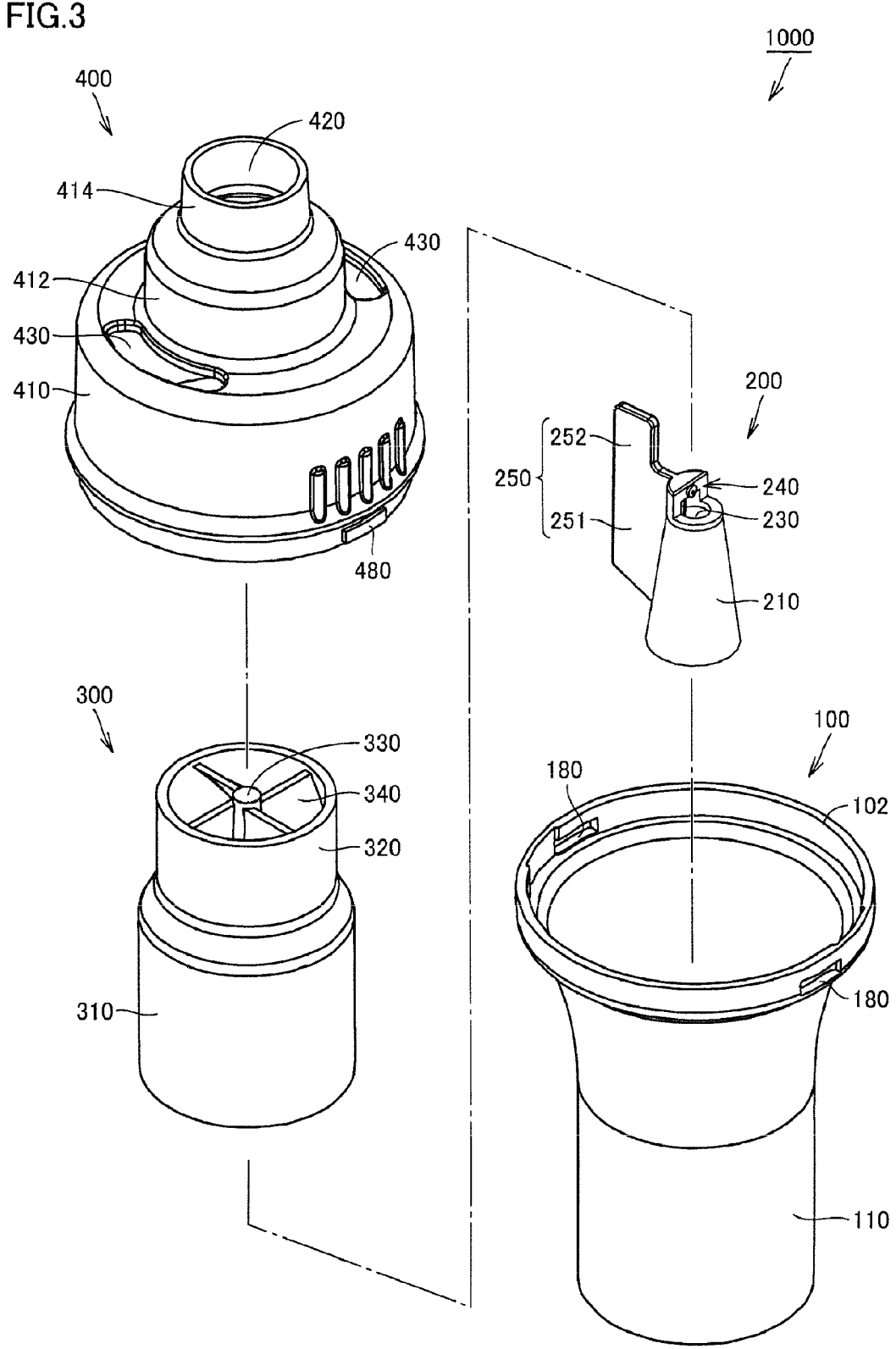
FIG. 3 is an exploded perspective view illustrating the nebulizer kit according to the first embodiment.

Referring again to FIGS. 3 to 5, the flow channel formation member 400 is attached to the case body 100 so as to cover the opening 102 of the case body 100. The flow channel formation member 400 includes a lower cylinder portion 410, the central cylinder portion 412, an upper cylinder portion 414, the aerosol discharge port 420, an outside air introduction port 430, and the interlocking protrusions 480.

The lower cylinder portion 410 is disposed coaxially with the central cylinder portion 412 and the upper cylinder portion 414. The diameter of the central cylinder portion 412 is greater than the diameter of the upper cylinder portion 414. The diameter of the lower cylinder portion 410 is greater than the diameter of the central cylinder portion 412. The flow channel formation member 400 is generally configured in an approximately cylindrical shape that extends upward from below while decreasing in diameter.

The aerosol discharge port 420 is formed on the inner side of the upper cylinder portion 414. The outside air introduction port 430 is provided in an area where the lower cylinder portion 410 and the central cylinder portion 412 are connected to each other (see FIG. 3). The interlocking protrusions 480 are provided in the vicinity of a lower end of the lower cylinder portion 410. As described above, when the flow channel formation member 400 is attached to the case body 100, the interlocking protrusions 480 interlock with corresponding interlocking holes 180 provided in the case body 100 (see FIGS. 2, 3, and 5). The upper cylinder portion 320 of the particle segregating portion 300 is fixed to an inner side of the central cylinder portion 412 (see FIG. 5).

Operations of Nebulizer Kit 1000

Operations of the nebulizer kit 1000 will be described with reference to FIGS. 13 and 14. FIG. 13 is a cross-sectional view illustrating the atomizing area M and the vicinity thereof when aerosol is produced by the nebulizer kit 1000 (see FIG. 2). FIG. 14 is a cross-sectional view illustrating a state of the nebulizer kit 1000 as a whole when aerosol is produced by the nebulizer kit 1000.

As shown in FIG. 13, the atomizing area M is formed at an exit region R115 of the nozzle hole 115 provided in the compressed air introduction tube 113 (a region where the center axis of the nozzle hole 115 provided in the compressed air introduction tube 113 intersects with the center axis of the liquid suction port 240 provided in the suction channel formation member 200) and in the vicinity of the exit region R115.

The compressed air introduced into the compressed air introduction tube 113 is expelled through the nozzle hole 115 provided in the upper tip area 113*a* (see an arrow AR113). A negative pressure, where the pressure is lower than the surroundings, is produced at the atomizing area M and the vicinity thereof as a result of the compressed air being expelled toward the exit region R115 from the nozzle hole 115.

The liquid W (see FIG. 14) is sucked upward, through the suction channel 221 and the suction channel 222, to the vicinity of the atomizing area M from the liquid reservoir portion 116 (see FIG. 14) due to the negative pressure produced at the atomizing area M and the vicinity thereof (see an arrow AR220 in FIG. 13). The liquid W is gradually discharged toward the atomizing area M from the liquid suction port 240. A small amount of the liquid W discharged from the liquid suction port 240 collides with the compressed air flowing in the direction of the arrow AR113 and breaks up at the atomizing area M, changing into mist particles (fine droplets) (not shown).

Referring to FIG. 14, these mist particles attach to the outside air introduced into the case body 100 through the outside air introduction port 430 (see an arrow AR430). The aerosol is produced at the atomizing area M. The aerosol moves toward the aerosol discharge port 420 through the interior of the particle segregating portion 300.

In the present embodiment, the blade portions 340 of the particle segregating portion 300 are disposed between the atomizing area M and the aerosol discharge port 420. Large (for example, a diameter of 10 μm or greater) particles of the aerosol moving toward the aerosol discharge port 420 from the atomizing area M adhere to the surfaces of the blade portions 340. Aerosol having desired particle diameters (for example, greater than or equal to 2 μm and less than 10 μm) segregated by the blade portions 340 is then discharged to the exterior through the aerosol discharge port 420. The aerosol is then sucked into the nose or mouth of the user through the mouthpiece 500 (see FIG. 1).

Actions and Effects

When the aerosol is produced in the nebulizer kit 1000, the compressed air expelled from the nozzle hole 115 makes contact with the liquid W discharged from the liquid suction port 240 while continuing to flow in a linear manner (see the arrow AR113 in FIGS. 13 and 14). Unlike the nebulizer kit 1000Z described earlier (see FIGS. 60 to 62), the compressed air expelled from the nozzle hole 115 is used in the production of aerosol without first making contact with other members or swirling greatly. Thus the compressed air introduced into the compressed air introduction tube 113 loses almost no pressure when producing the aerosol.

It is thus necessary to prepare compressed air at a lower flow rate in the nebulizer kit 1000 than in the nebulizer kit 1000Z in order to produce aerosol having the same quantity of mist in the nebulizer kit 1000 and the nebulizer kit 1000Z. The nebulizer kit 1000 uses the compressed air efficiently when producing the aerosol, and thus a compressor whose capacity (flow rate) and overall size are lower than that of the nebulizer kit 1000Z can be used. Accordingly, the nebulizer kit 1000 not only can be manufactured cheaply, but also can reduce the amount of energy consumed to produce the aerosol.

The nebulizer kit 1000 can be broken down into individual components and thus the individual components can be cleaned with ease. In the nebulizer kit 1000, the plate-shaped gripping portion 250 is provided in the suction channel formation member 200. The suction channel formation member 200 is prevented from being lost during cleaning by using the plate-shaped gripping portion 250.

In the suction channel formation member 200, the direction in which the suction channel 222 extends and the position in which the liquid suction port 240 is provided are on the opposite side from the direction in which the plate-shaped gripping portion 250 extends. Thus the spray of the aerosol produced at the atomizing area M is not inhibited by the plate-shaped gripping portion 250.

Figure 5:
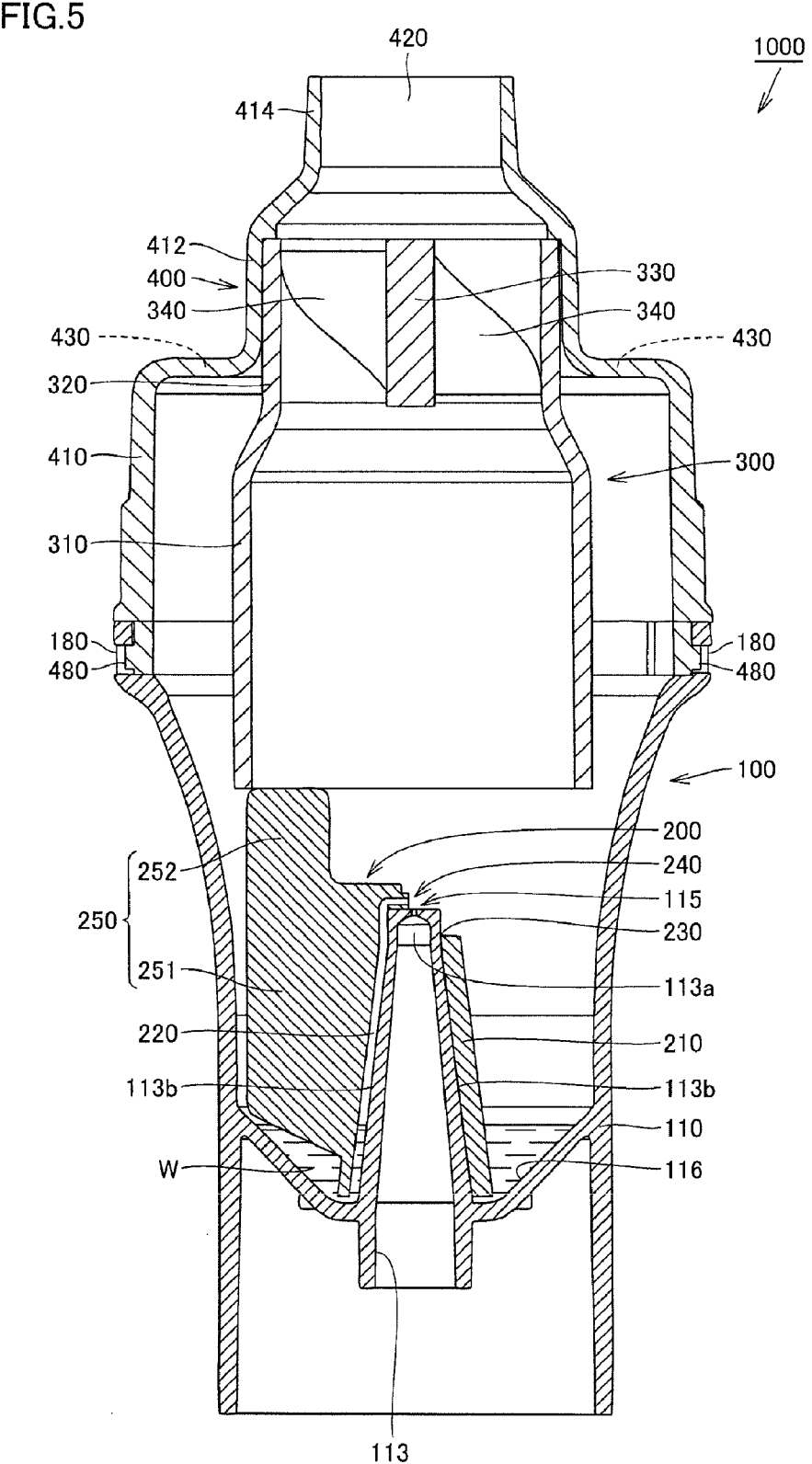
FIG. 5 is a cross-sectional view taken along a V-V line shown in FIG. 2.
Figure 6:
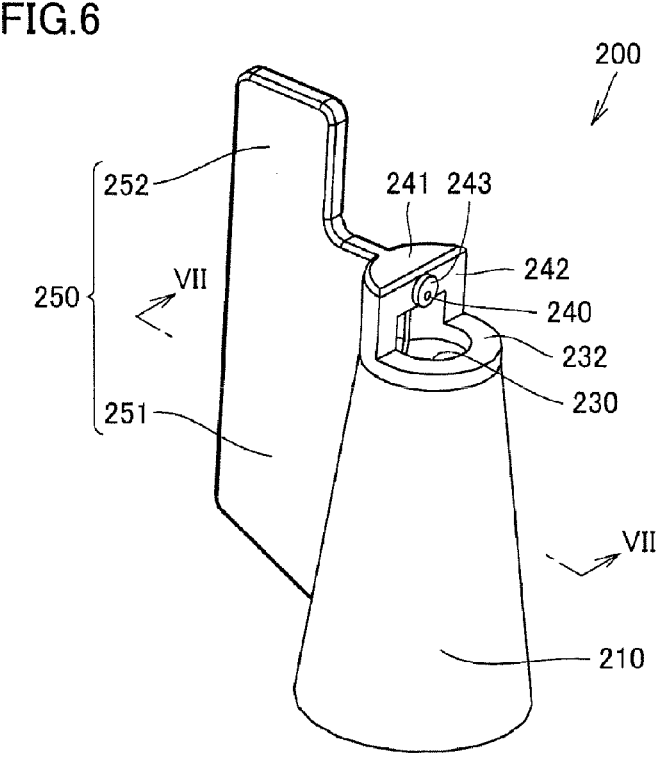
FIG. 6 is a first perspective view illustrating a suction channel formation member used in the nebulizer kit according to the first embodiment.
Figure 7:
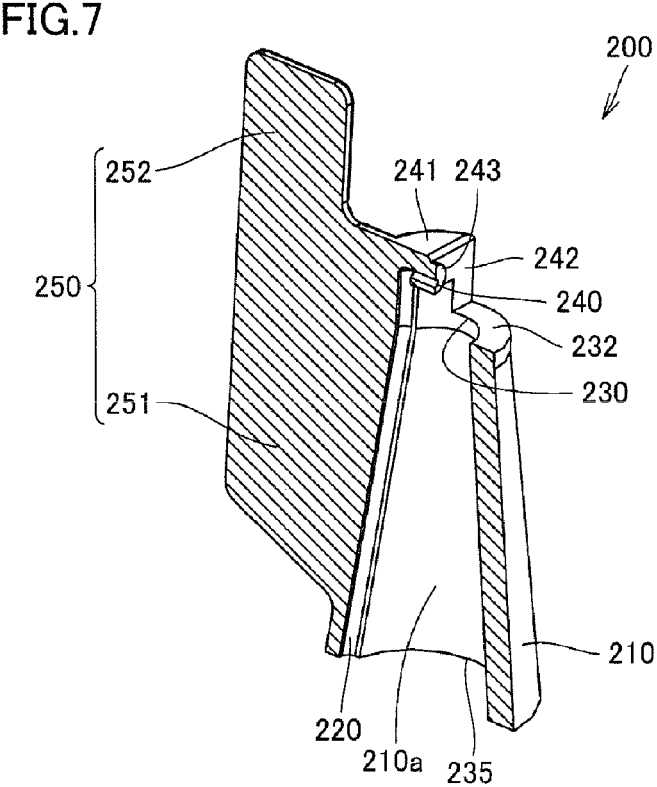
FIG. 7 is a cross-sectional perspective view taken along a VII-VII line shown in FIG. 6, and is a first cross-sectional perspective view illustrating the suction channel formation member used in the nebulizer kit according to the first embodiment.

In the nebulizer kit 1000, the lower end of the particle segregating portion 300 makes contact with the upper end of the protrusion 252 of the suction channel formation member 200 (see FIG. 5). Vertical movement of the suction channel formation member 200 relative to the case body 100 is fixed (that is, the suction channel formation member 200 is positioned). Thus the suction channel formation member 200 is securely prevented from being pushed upward by the compressed air expelled from the nozzle hole 115. The aerosol can thus be produced continuously at the atomizing area M.

The nebulizer kit 1000 may be configured so that the suction channel formation member 200 is not fixed to the case body 100 in a rotation direction and the suction channel formation member 200 can freely rotate around the compressed air introduction tube 113 relative to the case body 100. In this case, in the case where the nebulizer kit 1000 is tilted, the suction channel formation member 200 rotates under the weight of the plate-shaped gripping portion 250 so that the plate-shaped gripping portion 250 is positioned downward in a gravitational direction. A lower end of the suction channel 221 can be continuously submerged in the liquid W held in the liquid reservoir portion 116. Thus the suction channel 221 can continually suck up the liquid W even in the case where the nebulizer kit 1000 is tilted.

As described above, the particle segregating portion 300 is fixed to the flow channel formation member 400 (the central cylinder portion 412). When the flow channel formation member 400 is removed from the case body 100, the particle segregating portion 300 and the flow channel formation member 400 are removed as well. The particle segregating portion 300 and the flow channel formation member 400 of the nebulizer kit 1000 are thus convenient when breaking down and cleaning those members.

In the particle segregating portion 300, the blade portions 340 are provided on the inner side of the upper cylinder portion 320. The blade portions 340 are positioned toward one side (end) of the particle segregating portion 300 in the lengthwise direction thereof. The blade portions 340 can be cleaned easily. In addition, the diameter of the particle segregating portion 300 decreases as the particle segregating portion 300 progresses from the lower cylinder portion 310 toward the upper cylinder portion 320. The particle segregating portion 300 can effectively segregate particles. Although the main purpose of the particle segregating portion 300 is to segregate aerosol particles based on the particle diameters, there are cases where particles having the required diameters can be obtained without using the particle segregating portion 300. In this case, it is preferable to use the nebulizer kit 1000 with the particle segregating portion 300 removed. For example, in the case where particles (aerosol) 15 μm in diameter are required, and particles (aerosol) 15 μm in diameter are produced at the atomizing area M, it is preferable to use the nebulizer kit 1000 with the particle segregating portion 300 removed.

Second Embodiment

Figure 15:
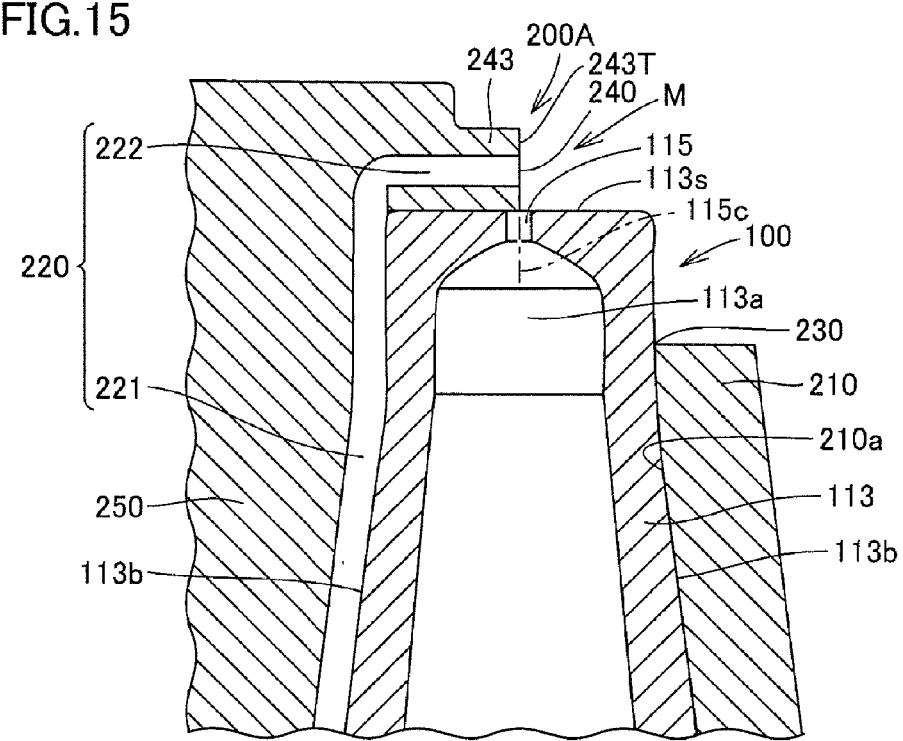
FIG. 15 is a cross-sectional view illustrating an atomizing area and the vicinity thereof in a nebulizer kit according to a second embodiment.

The present embodiment will be described with reference to FIG. 15. A nebulizer kit according to the present embodiment includes a suction channel formation member 200A instead of the suction channel formation member 200 (see FIG. 13 and so on) according to the aforementioned first embodiment.

As described above, the liquid suction port 240 of the suction channel formation member 200 (see FIG. 13 and so on) does not overlap with the nozzle hole 115, and is instead disposed slightly back from the nozzle hole 115. However, in the suction channel formation member 200A, the liquid suction port 240 is positioned above the region in which the nozzle hole 115 is provided when the nozzle hole 115 is viewed from the liquid suction port 240.

Figure 13:
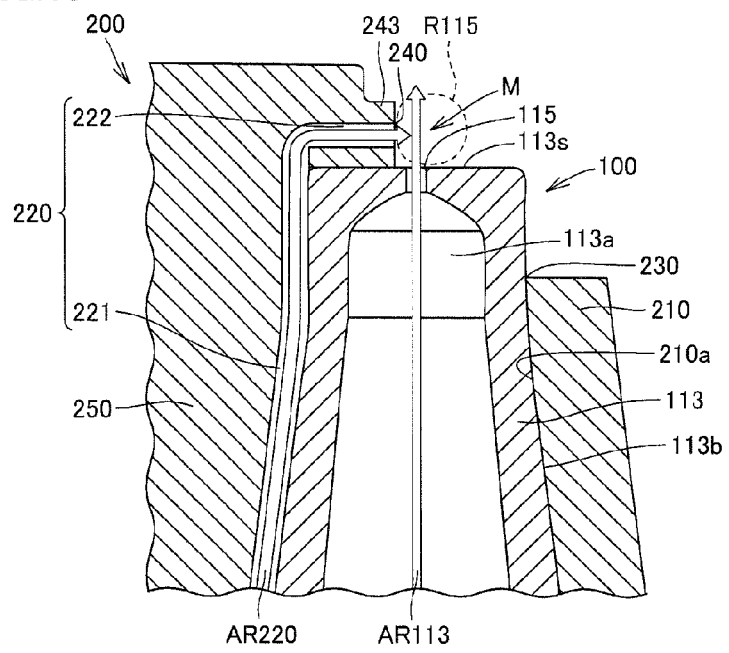
FIG. 13 is a cross-sectional view illustrating an atomizing area and the vicinity thereof when aerosol is produced by the nebulizer kit according to the first embodiment.

The position of the liquid suction port 240 is closer to the nozzle hole 115 in the suction channel formation member 200A than in the suction channel formation member 200 (see FIG. 13 and so on). It is easier for a negative pressure to be produced at the atomizing area M in the suction channel formation member 200A than in the suction channel formation member 200 (see FIG. 13 and so on). Accordingly, a lower flow of compressed air introduced into the compressed air introduction tube 113 can be achieved in the suction channel formation member 200A than in the suction channel formation member 200 (see FIG. 13 and so on).

In the case where the nozzle hole 115 is formed in a circular shape (to rephrase, in the case where the nozzle hole 115 is formed from a circular column-shaped space), a center line 115c of the nozzle hole 115 may be positioned on a plane that includes the liquid suction port 240. In this case, a leading end area 243T of the liquid suction port formation member 243 and the center line 115c of the nozzle hole 115 are positioned in the same plane.

It is preferable for a position of the liquid suction port 240 relative to the nozzle hole 115 (that is, a distance between the liquid suction port 240 and the nozzle hole 115) to be optimized in accordance with the flow amount and so on of the compressed air introduced into the compressed air introduction tube 113 in order to more efficiently produce the aerosol at the atomizing area M. According to experimental results, a comparatively high amount of compressed air results in more aerosol being produced when more than half of the nozzle hole 115 is exposed. On the other hand, a comparatively low amount of compressed air results in more aerosol being produced when essentially half of the nozzle hole 115 is exposed.

Third Embodiment

Figure 16:
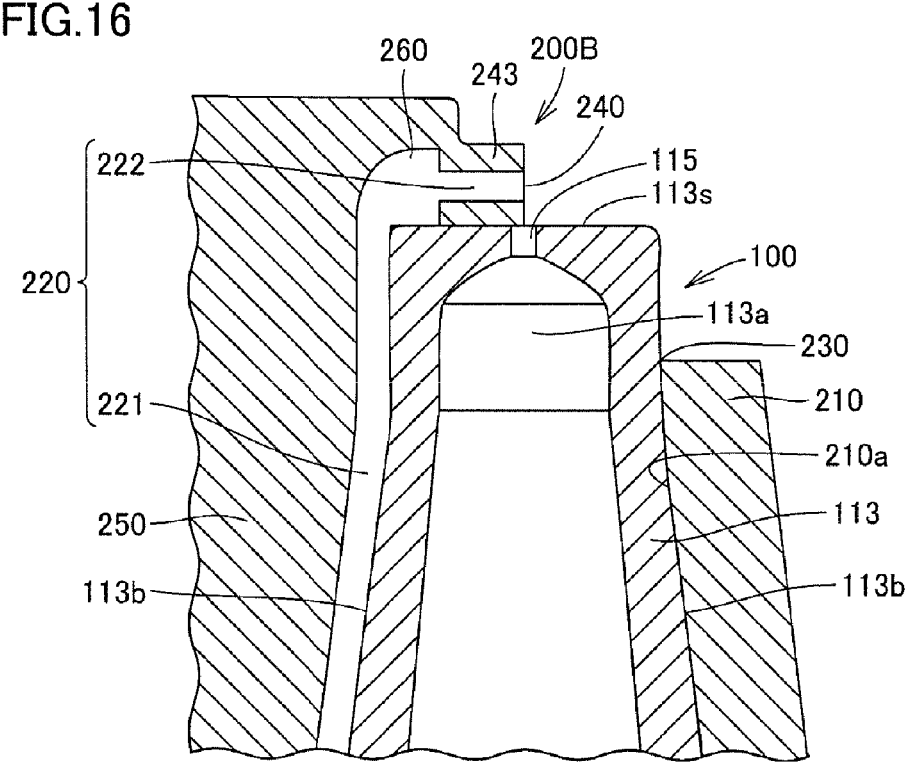
FIG. 16 is a cross-sectional view illustrating an atomizing area and the vicinity thereof in a nebulizer kit according to a third embodiment.

The present embodiment will be described with reference to FIG. 16. A nebulizer kit according to the present embodiment includes a suction channel formation member 200B instead of the suction channel formation member 200A (see FIG. 15 and so on) according to the aforementioned second embodiment.

In the suction channel formation member 200B, a liquid collecting portion 260 having a larger cross-sectional channel area than the suction channel 222 is provided in a region where the suction channel 221 and the suction channel 222 intersect (an intersecting region).

The liquid W that has been sucked upward under the negative pressure reaches the liquid collecting portion 260 after passing through the suction channel 221. After first collecting in the liquid collecting portion 260, the liquid W is discharged from the liquid suction port 240 through the suction channel 222. By providing the liquid collecting portion 260, the liquid W can be discharged from the liquid suction port 240 continuously in a stable manner without interruption.

Fourth Embodiment

Figure 17:
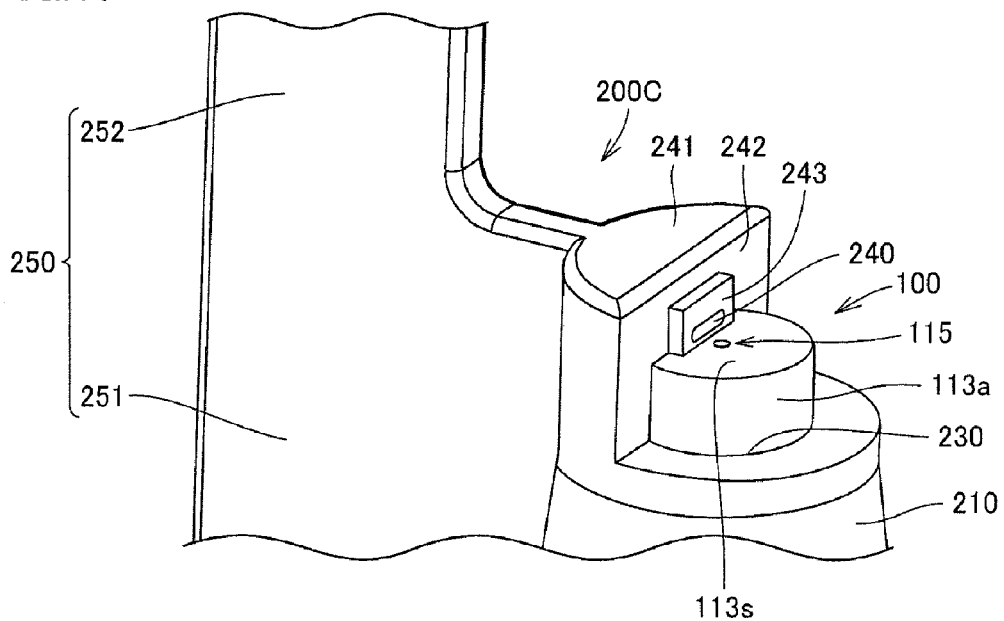
FIG. 17 is a perspective view illustrating an atomizing area and the vicinity thereof in a nebulizer kit according to a fourth embodiment.

The present embodiment will be described with reference to FIG. 17. A nebulizer kit according to the present embodiment includes a suction channel formation member 200C instead of the suction channel formation member 200 (see FIG. 10 and so on) according to the aforementioned first embodiment.

In the suction channel formation member 200C, the liquid suction port 240 is formed having a rounded slot shape. The opening of the liquid suction port 240 is shaped so as to extend parallel to the leading end surface 113s of the compressed air introduction tube 113 (that is, horizontally). The liquid suction port 240 may be formed so that the shape of the opening thereof intersects with the center axis of the nozzle hole 115 at a right angle.

The liquid W that has been sucked upward under the negative pressure is discharged from the liquid suction port 240. The liquid W discharged from the liquid suction port 240 spreads out in the horizontal direction and makes contact with the compressed air expelled from the nozzle hole 115 as a thin liquid film.

A small amount of the liquid W that has become a liquid film gradually makes contact with the compressed air expelled from the nozzle hole 115. The liquid W is more easily broken up by the compressed air expelled from the nozzle hole 115, and thus an improvement in the misting efficiency is achieved.

Fifth Embodiment

Figure 18:
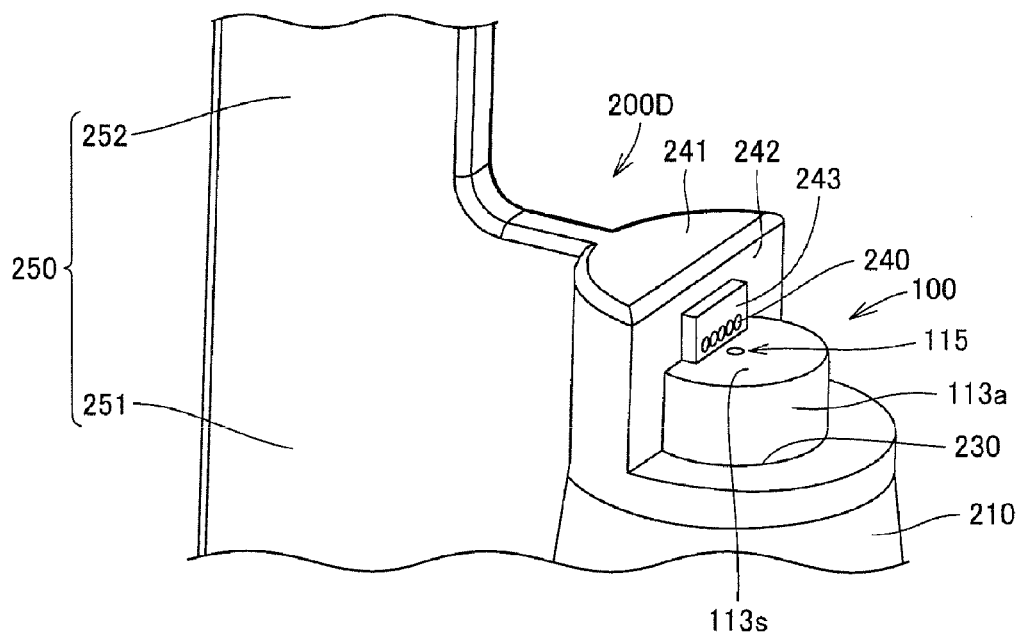
FIG. 18 is a perspective view illustrating an atomizing area and the vicinity thereof in a nebulizer kit according to a fifth embodiment.

The present embodiment will be described with reference to FIG. 18. A nebulizer kit according to the present embodiment includes a suction channel formation member 200D instead of the suction channel formation member 200 (see FIG. 10 and so on) according to the aforementioned first embodiment.

In the suction channel formation member 200D, a plurality of liquid suction ports 240 are provided. The plurality of liquid suction ports 240 are arranged in a row parallel to the leading end surface 113s of the compressed air introduction tube 113 (that is, horizontally). The plurality of liquid suction ports 240 may be arranged in a row that intersects with the center axis of the nozzle hole 115 at a right angle.

The liquid W that has been sucked upward under the negative pressure is discharged from each of the plurality of liquid suction ports 240. The amount of the liquid W discharged from each individual liquid suction port 240 is lower than in the suction channel formation member 200 according to the aforementioned first embodiment. The small amount of liquid W discharged from each individual liquid suction port 240 makes contact with the compressed air expelled from the nozzle hole 115.

The small amount of liquid W discharged from each individual liquid suction port 240 gradually makes contact with the compressed air expelled from the nozzle hole 115. The liquid W is more easily broken up by the compressed air expelled from the nozzle hole 115, and thus an improvement in the misting efficiency is achieved.

Sixth Embodiment

Figure 19:
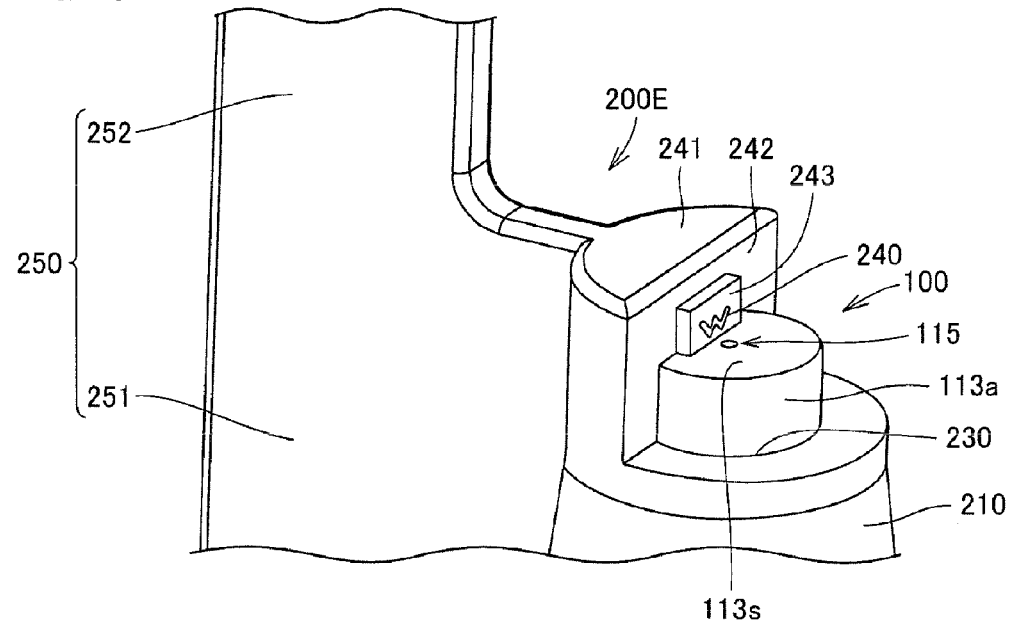
FIG. 19 is a perspective view illustrating an atomizing area and the vicinity thereof in a nebulizer kit according to a sixth embodiment.

The present embodiment will be described with reference to FIG. 19. A nebulizer kit according to the present embodiment includes a suction channel formation member 200E instead of the suction channel formation member 200 (see FIG. 10 and so on) according to the aforementioned first embodiment.

In the suction channel formation member 200E, the liquid suction port 240 is formed having a W shape. The liquid W that has been sucked upward under the negative pressure is gradually discharged from the narrow area at the lower end of the liquid suction port 240. The amount of the liquid W discharged from the liquid suction port 240 is lower than in the suction channel formation member 200 according to the aforementioned first embodiment. The small amount of liquid W discharged from the liquid suction port 240 makes contact with the compressed air expelled from the nozzle hole 115.

The small amount of liquid W discharged from the liquid suction port 240 gradually makes contact with the compressed air expelled from the nozzle hole 115. The liquid W is more easily broken up by the compressed air expelled from the nozzle hole 115, and thus an improvement in the misting efficiency is achieved. The same actions and effects as in the present embodiment can also be achieved in the case where the liquid suction port 240 is formed in a V shape, an M shape, or the like.

Seventh Embodiment

Figure 20:
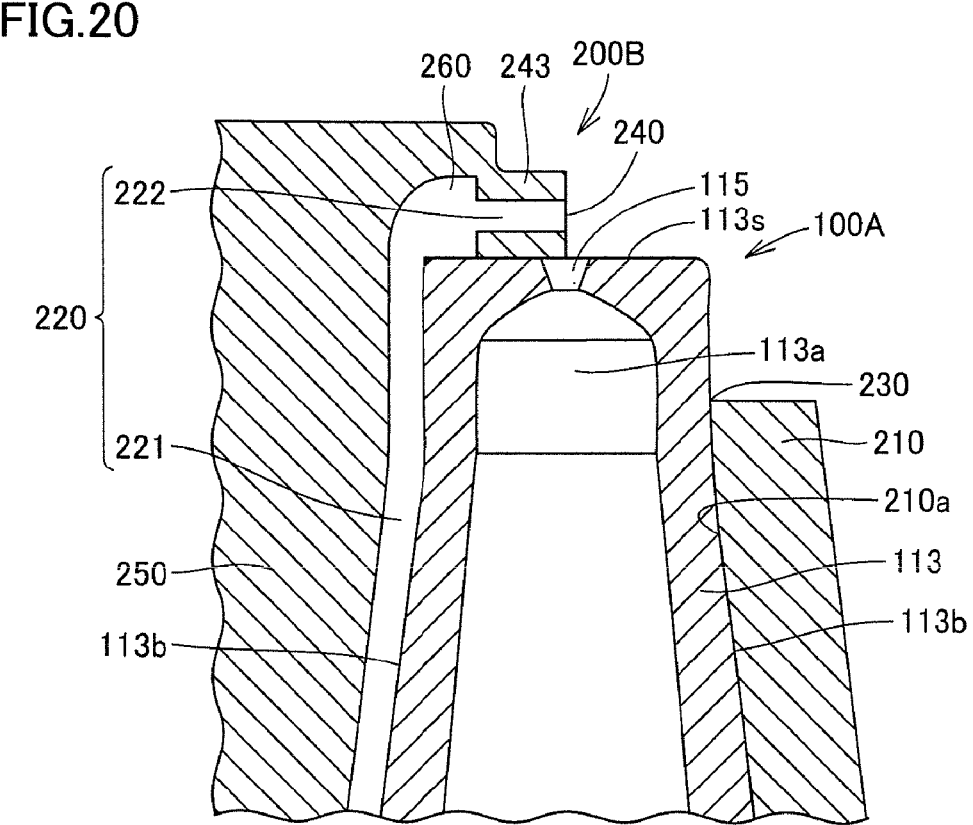
FIG. 20 is a cross-sectional view illustrating an atomizing area and the vicinity thereof in a nebulizer kit according to a seventh embodiment.

The present embodiment will be described with reference to FIG. 20. A nebulizer kit according to the present embodiment includes a case body 100A instead of the case body 100 (see FIG. 16 and so on) according to the aforementioned third embodiment. The configuration of the case body 100A described hereinafter can also be applied in the first embodiment (see FIG. 10), the second embodiment (see FIG. 15), the fourth embodiment (see FIG. 17), the fifth embodiment (see FIG. 18), and the sixth embodiment (see FIG. 19).

In the case body 100A, the nozzle hole 115, which is defined by a round, cylindrical inner circumferential surface, is configured as a tapered surface that widens outward. The diameter of the nozzle hole 115 gradually increases following the direction in which the compressed air flows. A loss of pressure in the compressed air decreases as the compressed air introduced into the compressed air introduction tube 113 passes through the nozzle hole 115. The compressed air is used more efficiently when producing the aerosol, and thus a compressor whose capacity (flow rate) and overall size are lower can be used.

Eighth Embodiment

Figure 21:
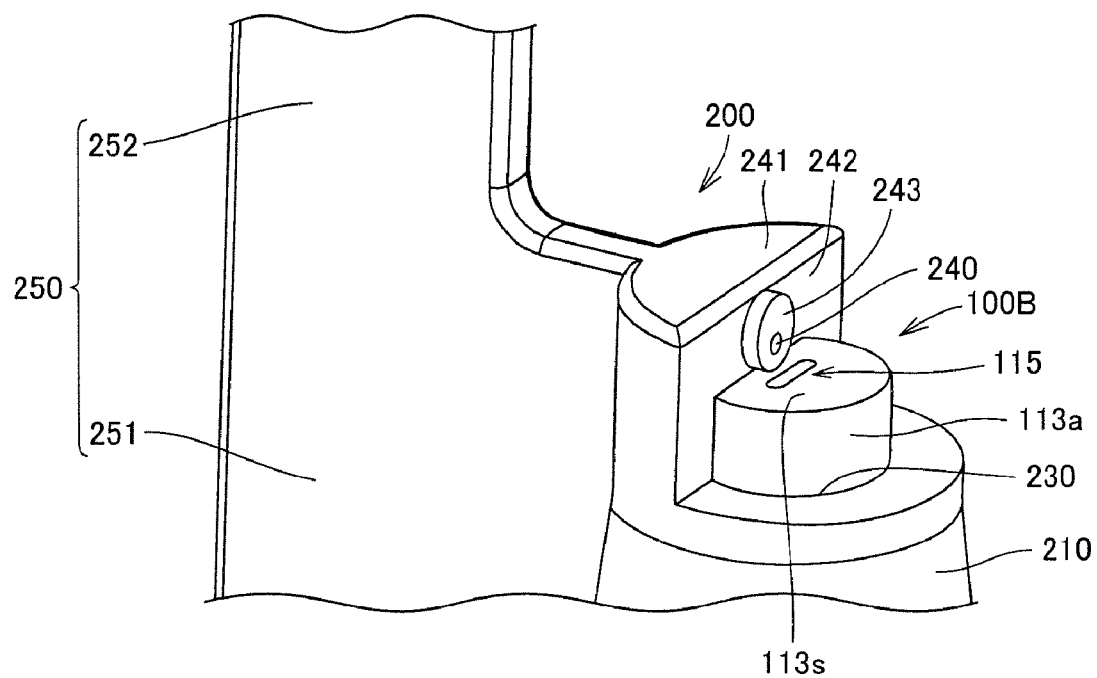
FIG. 21 is a perspective view illustrating an atomizing area and the vicinity thereof in a nebulizer kit according to an eighth embodiment.

The present embodiment will be described with reference to FIG. 21. A nebulizer kit according to the present embodiment includes a case body 100B instead of the case body 100 (see FIG. 10 and so on) according to the aforementioned first embodiment. The configuration of the case body 100B described hereinafter can also be applied in the second embodiment (see FIG. 15), the third embodiment (see FIG. 16), the fourth embodiment (see FIG. 17), the fifth embodiment (see FIG. 18), and the sixth embodiment (see FIG. 19).

In the case body 100B, the nozzle hole 115 is formed having rounded slot shape. The opening of the nozzle hole 115 is shaped so as to extend orthogonally (that is, horizontally) to the direction of the center axis of the liquid suction port 240 (the suction channel 222 in FIG. 11). The compressed air expands in the horizontal direction and is thus expelled from the nozzle hole 115 in a flat (rectangular) shape.

The liquid W that has been sucked upward under the negative pressure is discharged from the liquid suction port 240. The liquid W discharged from the liquid suction port 240 makes contact with the compressed air expelled in an approximately rectangular shape. The liquid W makes contact with the compressed air across a wide range. The liquid W is more easily broken up by the compressed air expelled from the nozzle hole 115, and thus an improvement in the misting efficiency is achieved.

Ninth Embodiment

Figure 22:
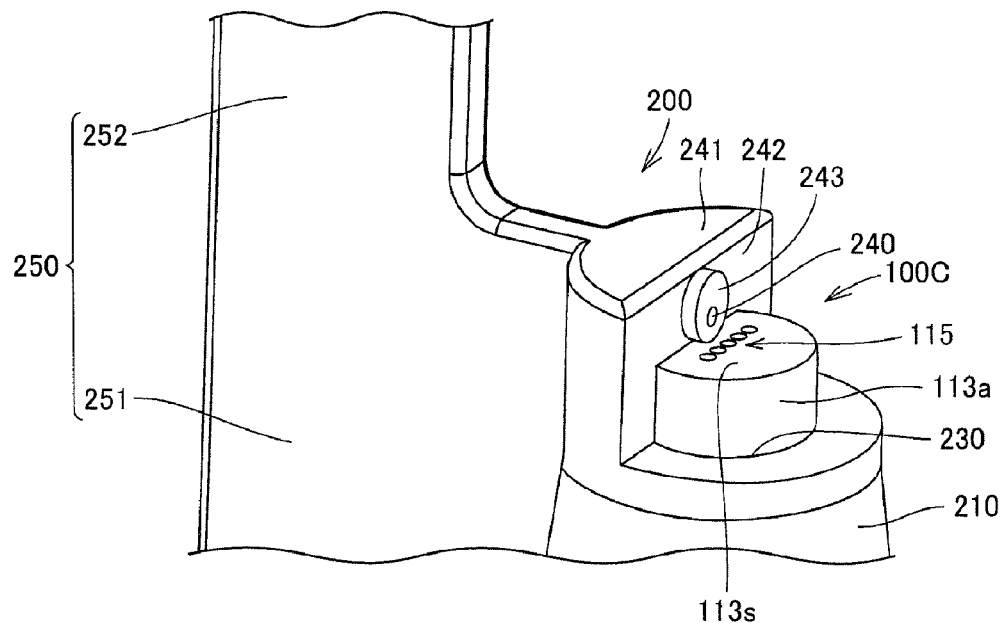
FIG. 22 is a perspective view illustrating an atomizing area and the vicinity thereof in a nebulizer kit according to a ninth embodiment.
Figure 23:
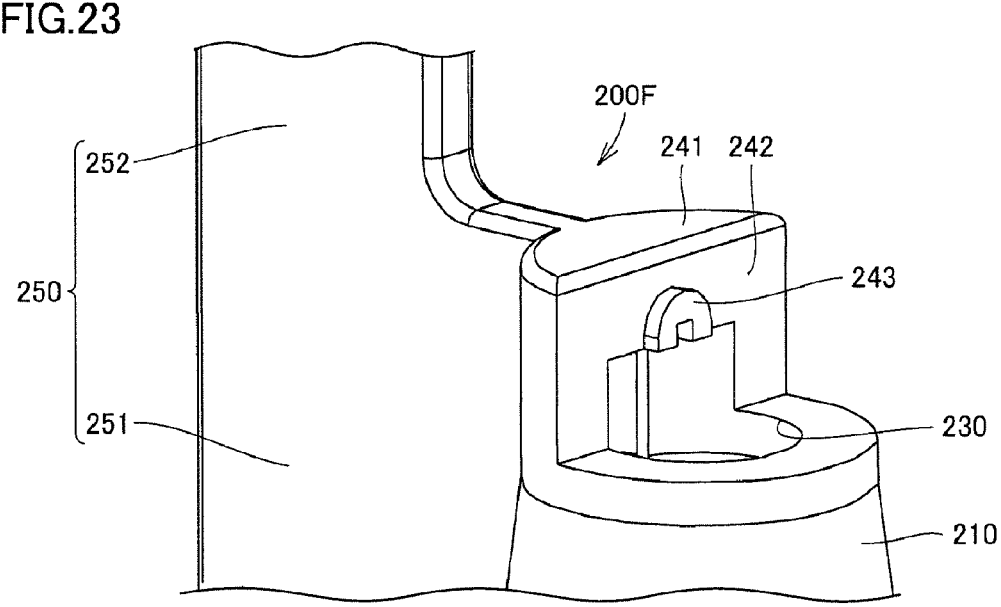
FIG. 23 is a perspective view illustrating a suction channel formation member used in a nebulizer kit according to a tenth embodiment.

The present embodiment will be described with reference to FIG. 22. A nebulizer kit according to the present embodiment includes a case body 100C instead of the case body 100 (see FIG. 10 and so on) according to the aforementioned first embodiment. The configuration of the case body 100C described hereinafter can also be applied in the second embodiment (see FIG. 15), the third embodiment (see FIG. 16), the fourth embodiment (see FIG. 17), the fifth embodiment (see FIG. 18), and the sixth embodiment (see FIG. 19).

In the case body 100C, a plurality of nozzle holes 115 are provided. The plurality of nozzle holes 115 are arranged in a row that extends orthogonally (that is, horizontally) to the direction of the center axis of the liquid suction port 240 (the suction channel 222 in FIG. 11).

The liquid W that has been sucked upward under the negative pressure is discharged from the liquid suction port 240. The liquid W discharged from the liquid suction port 240 makes contact with the compressed air expelled from each of the plurality of nozzle holes 115. The liquid W makes contact with the compressed air across a wide range. The liquid W is more easily broken up by the compressed air expelled from the nozzle hole 115, and thus an improvement in the misting efficiency is achieved.

Tenth Embodiment

The present embodiment will be described with reference to FIGS. 23 and 24. A nebulizer kit according to the present embodiment includes a suction channel formation member 200F instead of the suction channel formation member 200 (see FIGS. 6, 7, and so on) according to the aforementioned first embodiment. The configuration of the suction channel formation member 200F described hereinafter can also be applied in the second embodiment (see FIG. 15), the third embodiment (see FIG. 16), the fourth embodiment (see FIG. 17), the fifth embodiment (see FIG. 18), the sixth embodiment (see FIG. 19), the seventh embodiment (see FIG. 20), the eighth embodiment (see FIG. 21), and the ninth embodiment (see FIG. 22).

In the suction channel formation member 200 according to the first embodiment (see FIGS. 6, 7, and so on), the suction channel formation portion 220 is provided in the inner circumferential surface 210*a* of the cylinder portion 210 as an indentation that extends approximately linearly from the opening 235 toward the opening 230, and is provided so as to pass through the interior of the expanded portion 241 and the liquid suction port formation member 243.

However, as shown in FIGS. 23 and 24, in the suction channel formation member 200F according to the present embodiment, the suction channel formation portion 220 is provided as an overall groove-shaped indentation and is not configured to pass through the liquid suction port formation member 243. The liquid suction port formation member 243 is formed in a U shape.

The suction channel formation member 200F is also contained and disposed within the case body 100 so that the outer circumferential surface 113*b* of the compressed air introduction tube 113 is covered by the cylinder portion 210. The suction channel 221 is formed along the outer circumferential surface 113*b* of the compressed air introduction tube 113. The suction channel 222 is formed so as to follow the leading end surface 113*s* of the compressed air introduction tube 113. The same actions and effects as described in the first embodiment can be achieved by the suction channel formation member 200F as well.

Eleventh Embodiment

The present embodiment will be described with reference to FIGS. 25 and 26. A nebulizer kit according to the present embodiment includes a suction channel formation member 200G instead of the suction channel formation member 200 (see FIGS. 6, 7, and so on) according to the aforementioned first embodiment, and includes a case body 100D instead of the case body 100 (see FIG. 10 and so on) according to the aforementioned first embodiment.

Like the suction channel formation member 200F in the aforementioned tenth embodiment (see FIGS. 23 and 24), the suction channel formation portion 220 (see FIG. 26) in the suction channel formation member 200G is provided as an overall groove-shaped indentation and is not configured to pass through the liquid suction port formation member 243. The liquid suction port formation member 243 is formed in a U shape.

In the case body 100D, a platform 143 having an indentation 144 is provided in the leading end surface 113*s* of the upper tip area 113*a*. The suction channel formation member 200G is attached to the case body 100D (the compressed air introduction tube 113) as indicated by an arrow in FIG. 26. The platform 143 is fitted into an inner side 244 of the liquid suction port formation member 243. The liquid suction port 240 (see FIG. 25) is formed by the indentation 144 in the platform 143 and the inner side 244 of the liquid suction port formation member 243. The same actions and effects as described in the first embodiment can be achieved by the suction channel formation member 200G and the case body 100D as well.

Twelfth Embodiment

The present embodiment will be described with reference to FIGS. 27 to 29. FIG. 27 is a perspective view illustrating an atomizing area and the vicinity thereof in a nebulizer kit according to the present embodiment. FIG. 28 is a cross-sectional view taken along a XXVIII-XXVIII line shown in FIG. 27. FIG. 29 is a cross-sectional view schematically illustrating a state when aerosol is produced at the atomizing area in the nebulizer kit according to the present embodiment.

The nebulizer kit according to the present embodiment includes a suction channel formation member 200H instead of the suction channel formation member 200 (see FIGS. 6, 7, and so on) according to the aforementioned first embodiment. The configuration of the suction channel formation member 200H described hereinafter can also be applied in the second embodiment (see FIG. 15), the third embodiment (see FIG. 16), the fourth embodiment (see FIG. 17), the fifth embodiment (see FIG. 18), the sixth embodiment (see FIG. 19), the seventh embodiment (see FIG. 20), the eighth embodiment (see FIG. 21), and the ninth embodiment (see FIG. 22).

As shown in FIGS. 27 and 28, in the suction channel formation member 200H, a leading end surface of the liquid suction port formation member 243 provided so as to protrude from the end surface 242 of the expanded portion 241 is sloped. An upper sloped surface region 270 that slopes toward the suction channel 221 as the region progresses upward is provided in an upper area of the liquid suction port 240. An angle of slope α of the upper sloped surface region 270 relative to the center axis of the nozzle hole 115 is set to be, for example, no less than 20° and no more than 45°. The angle of slope α is set to 35° from the standpoint of improving the misting efficiency.

Figure 28:
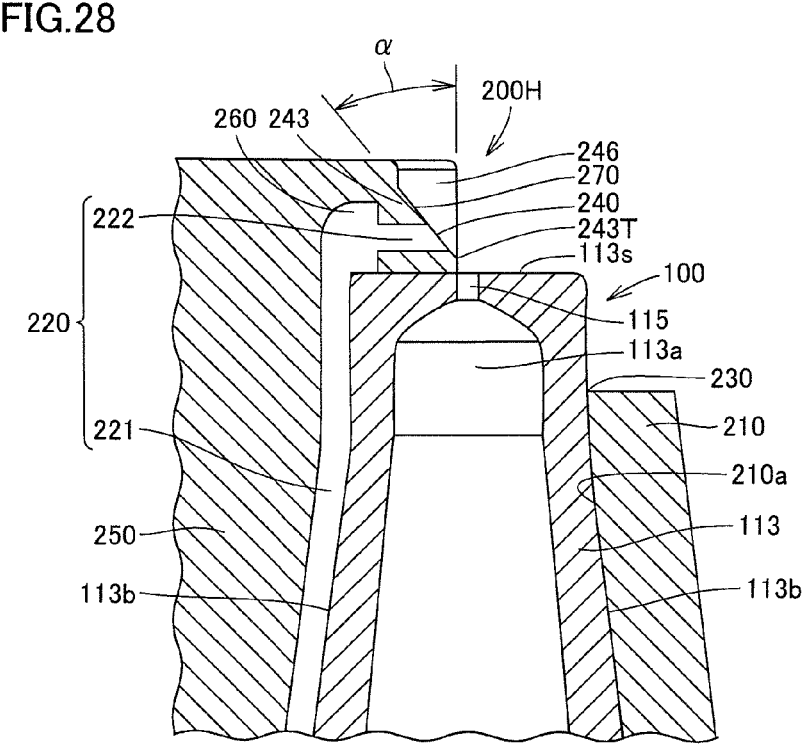
FIG. 28 is a cross-sectional view taken along a XXVIII-XXVIII line shown in FIG. 27.

As shown in FIG. 28, the leading end area 243T of the liquid suction port formation member 243 is disposed so as to follow the inner circumferential surface of the end of the nozzle hole 115 (that is, so as to make contact with an outer edge of the nozzle hole 115). Like the aforementioned case described with reference to FIG. 15 (the second embodiment), the leading end area 243T may be disposed so as to match the center line of the nozzle hole 115 (the center line 115c in FIG. 15).

Figure 27:
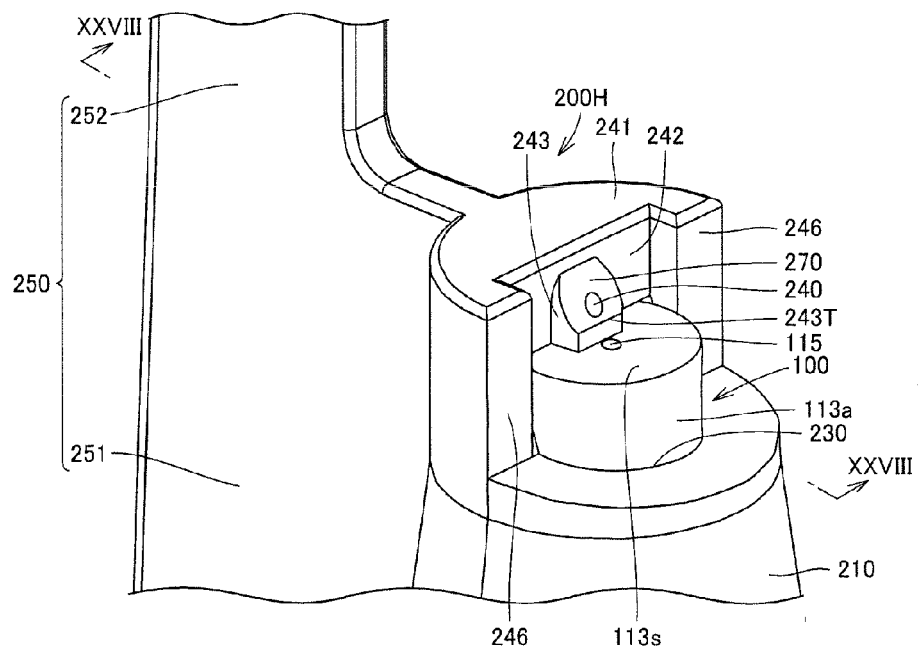
FIG. 27 is a perspective view illustrating an atomizing area and the vicinity thereof in a nebulizer kit according to a twelfth embodiment.

As shown in FIGS. 27 and 28, two expanded portions 246 are provided in the end surface 242 of the expanded portion 241. The expanded portions 246 are disposed so as to enclose the upper tip area 113a from both outer sides of the upper tip area 113a. As shown in FIG. 28, in the present embodiment, a leading end surface of the expanded portions 246 and the leading end area 243T of the liquid suction port formation member 243 are located in the same plane.

Actions and Effects

Figure 29:
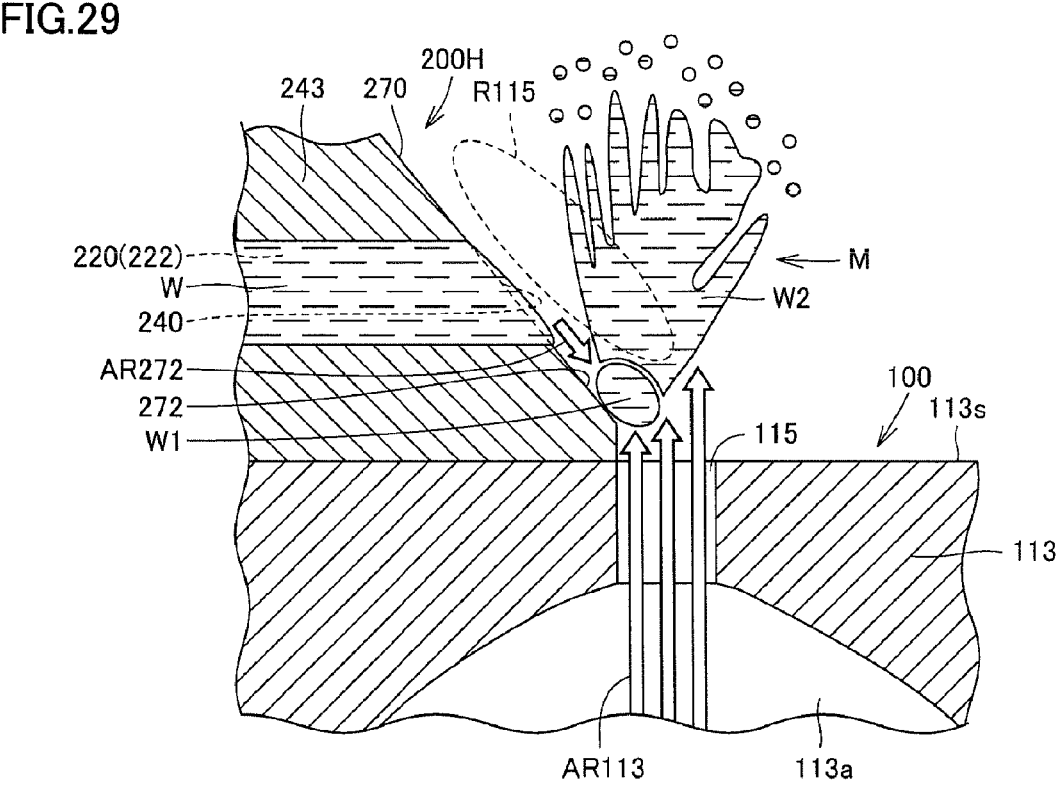
FIG. 29 is a cross-sectional view schematically illustrating a state when aerosol is produced at an atomizing area in the nebulizer kit according to the twelfth embodiment.

With reference to FIG. 29, in the suction channel formation member 200H, the upper sloped surface region 270 is provided above the liquid suction port 240. The liquid suction port 240 and the upper sloped surface region 270 are sloped so as to gradually recede away from a channel along which the compressed air expelled from the nozzle hole 115 progresses (see the arrow AR113). Because the liquid suction port 240 is sloped (to rephrase, because the liquid suction port 240 is formed so as to recede from the nozzle hole 115 progressively as the liquid suction port 240 progresses upward), the amount of liquid W supplied can be adjusted by increasing or decreasing the slope of the liquid suction port 240. For example, the amount of liquid W supplied can be reduced to an optimal value by increasing the slope of the liquid suction port 240 (that is, increasing the value of the angle of slope α). By optimizing the slope of the liquid suction port 240, the compressed air expelled from the nozzle hole 115 can be used to break up the liquid W with the highest energy efficiency as possible. In addition, because the liquid suction port 240 is sloped, the compressed air expelled from the nozzle hole 115 can be securely suppressed from entering into the liquid suction port 240. Therefore, according to the suction channel formation member 200H, the energy usage efficiency when atomizing the liquid W can be improved further.

In the present embodiment, a sloped surface 272 is also provided below the liquid suction port 240. The upper sloped surface region 270, the liquid suction port 240, and the sloped surface 272 slope toward the nozzle hole 115 along the same direction. The liquid W discharged from the liquid suction port 240 turns into a droplet W1 and slides down along the sloped surface 272 (see an arrow AR272). The droplet W1 gradually advances into a region above the nozzle hole 115, starting with the area of the droplet W1 on the front thereof in the direction of the slide, and then makes contact with the compressed air. The droplet W1 is then broken up, starting with the area of the droplet W1 on the front thereof in the direction of the slide, due to the contact with the compressed air.

By providing the sloped surface 272 below the liquid suction port 240, small amounts of the droplet W1 are consecutively supplied to the compressed air expelled from the nozzle hole 115. The liquid W (the droplet W1) is more easily broken up by the compressed air expelled from the nozzle hole 115, and thus an improvement in the misting efficiency is achieved.

In order to reduce the size of the droplet W1, it is preferable for the sloped surface 272 (that is, a region of the suction channel formation member 200 located between the liquid suction port 240 and the nozzle hole 115) to be more hydrophilic than the other regions of the suction channel formation member 200H where the sloped surface 272 is provided. Reducing the size of the droplet W1 makes it possible to obtain smaller particles when the droplet W1 is broken up. Coating the sloped surface 272 with a hydrophilic liquid, providing fine non-planarities in the sloped surface 272, and so on may be used to increase the hydrophilic properties of the sloped surface 272.

Providing the upper sloped surface region 270 above the liquid suction port 240 increases the size of a space for dispersing aerosol W2 produced when the droplet W1 breaks up. Thus the aerosol W2 can be produced in a broader space (atomizing area M).

It is preferable for the angle of slope α of the upper sloped surface region 270 relative to the center axis of the nozzle hole 115 to be optimized in accordance with the flow amount and so on of the compressed air introduced into the compressed air introduction tube 113 in order to more efficiently produce the aerosol at the atomizing area M.

Thirteenth Embodiment

Figure 30:
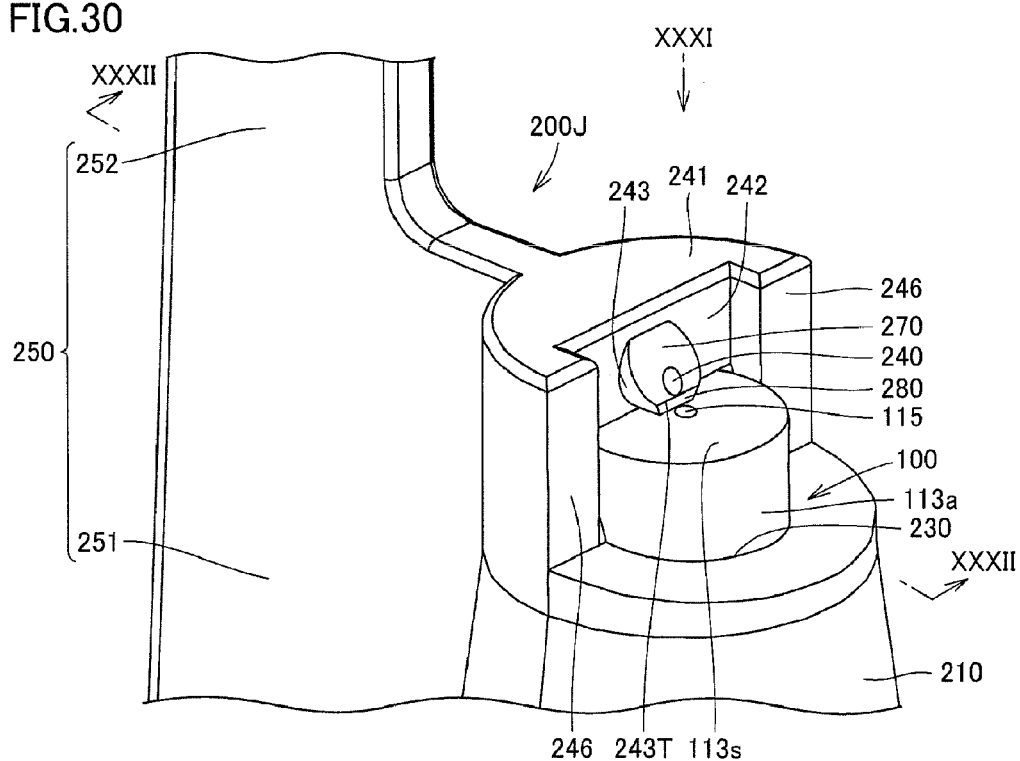
FIG. 30 is a perspective view illustrating an atomizing area and the vicinity thereof in a nebulizer kit according to a thirteenth embodiment.
Figure 31:
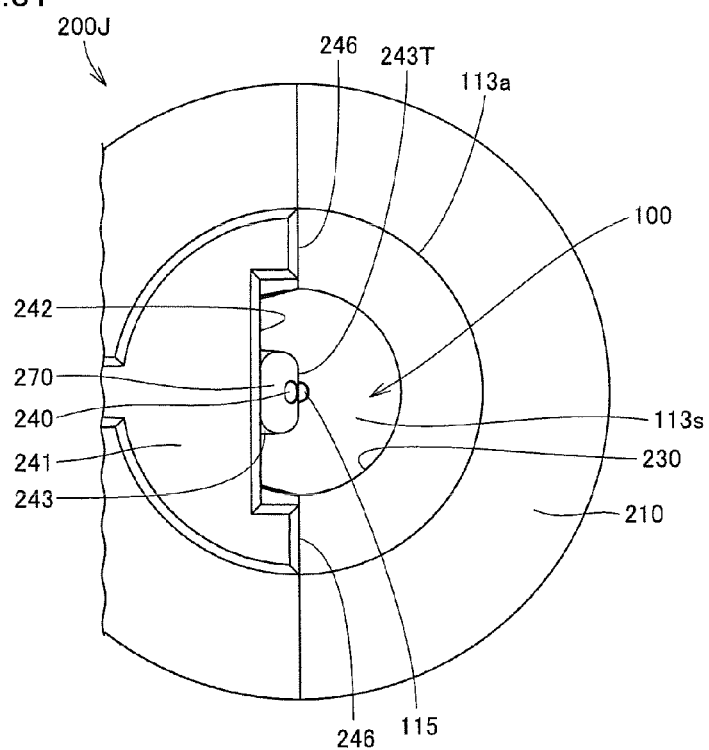
FIG. 31 is a plan view seen from the direction of an arrow XXXI shown in FIG. 30.
Figure 32:
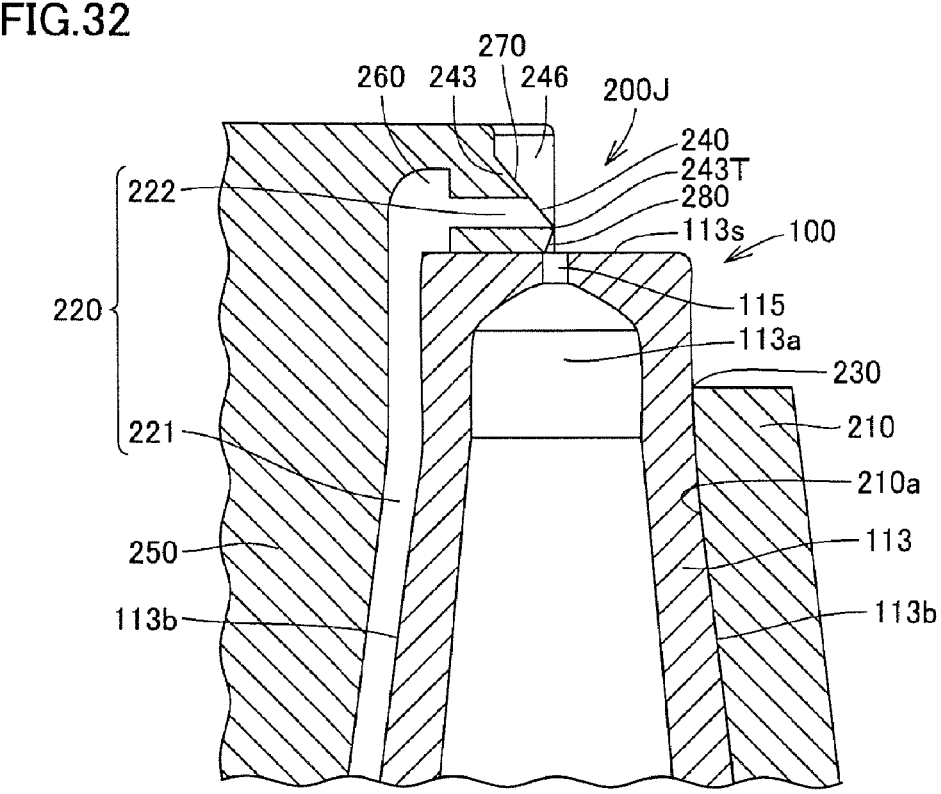
FIG. 32 is a cross-sectional view taken along a XXXII-XXXII line shown in FIG. 30.

The present embodiment will be described with reference to FIGS. 30 to 32. FIG. 30 is a perspective view illustrating an atomizing area and the vicinity thereof in a nebulizer kit according to the present embodiment. FIG. 31 is a plan view illustrating a case body 100 and the like as viewed from the direction of an arrow XXXI shown in FIG. 30. FIG. 32 is a cross-sectional view taken along a XXXII-XXXII line shown in FIG. 30.

The nebulizer kit according to the present embodiment includes a suction channel formation member 200J instead of the suction channel formation member 200H (see FIG. 27 and so on) according to the aforementioned twelfth embodiment. The configuration of the suction channel formation member 200J described hereinafter can also be applied in the first embodiment (see FIG. 10), the second embodiment (see FIG. 15), the third embodiment (see FIG. 16), the fourth embodiment (see FIG. 17), the fifth embodiment (see FIG. 18), the sixth embodiment (see FIG. 19), the seventh embodiment (see FIG. 20), the eighth embodiment (see FIG. 21), and the ninth embodiment (see FIG. 22).

As shown in FIG. 30, in the suction channel formation member 200J, a lower sloped surface region 280 that slopes in the direction of the suction channel 221 (see FIG. 32) as the region progresses downward is provided below the liquid suction port 240. A lower end area of the lower sloped surface region 280 is disposed so as to make contact with an outer edge of the nozzle hole 115.

As shown in FIGS. 31 and 32, the leading end area 243T of the liquid suction port formation member 243 is located in an area where the upper sloped surface region 270 and the lower sloped surface region 280 intersect (see FIG. 32). The sloped surface 272 according to the aforementioned twelfth embodiment (see FIG. 29) may furthermore be provided between the lower sloped surface region 280 and the liquid suction port 240. When the nozzle hole 115 is viewed from the liquid suction port 240, the leading end area 243T of the liquid suction port formation member 243 is positioned in the center of the nozzle hole 115.

According to the suction channel formation member 200J, the direction in which the compressed air expelled from the nozzle hole 115 advances gradually changes along the lower sloped surface region 280, spreading in a direction moving away from the liquid suction port 240. The compressed air expelled from the nozzle hole 115 can be securely suppressed from entering into the liquid suction port 240. Therefore, according to the suction channel formation member 200J, the usage efficiency of the compressed air is high when producing the aerosol.

Fourteenth Embodiment

Figure 33:
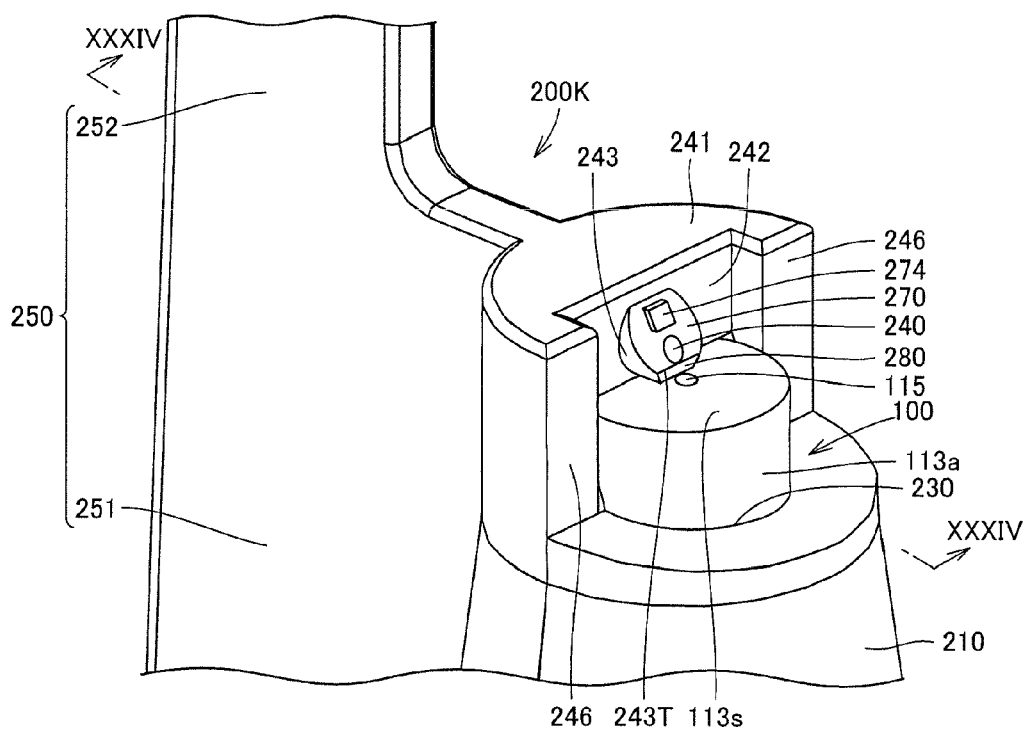
FIG. 33 is a perspective view illustrating an atomizing area and the vicinity thereof in a nebulizer kit according to a fourteenth embodiment.
Figure 34:
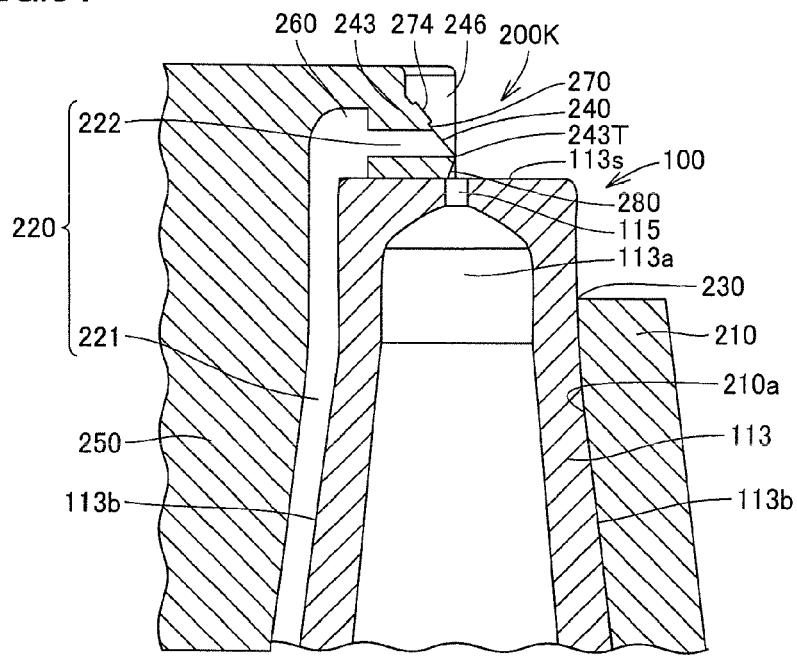
FIG. 34 is a cross-sectional view taken along a XXXIV-XXXIV line shown in FIG. 33.

The present embodiment will be described with reference to FIGS. 33 and 34. FIG. 33 is a perspective view illustrating an atomizing area and the vicinity thereof in a nebulizer kit according to the present embodiment. FIG. 34 is a cross-sectional view taken along a XXXIV-XXXIV line shown in FIG. 33.

A nebulizer kit according to the present embodiment includes a suction channel formation member 200K instead of the suction channel formation member 200J (see FIG. 30 and so on) according to the aforementioned thirteenth embodiment. The configuration of the suction channel formation member 200K described hereinafter can also be applied in the first embodiment (see FIG. 10), the second embodiment (see FIG. 15), the third embodiment (see FIG. 16), the fourth embodiment (see FIG. 17), the fifth embodiment (see FIG. 18), the sixth embodiment (see FIG. 19), the seventh embodiment (see FIG. 20), the eighth embodiment (see FIG. 21), and the ninth embodiment (see FIG. 22).

As shown in FIGS. 33 and 34, in the suction channel formation member 200K, a protrusion 274 is provided in the surface of the upper sloped surface region 270. The protrusion 274 is quadrangular in shape. The protrusion 274 protrudes from the upper sloped surface region 270 by approximately 0.2 mm. The protrusion 274 may have a semi-spherical shape. According to the suction channel formation member 200K, providing the protrusion 274 in the upper sloped surface region 270 makes it possible to increase the value of the negative pressure produced at the atomizing area M and the vicinity thereof (to rephrase, reduces the pressure at the atomizing area M and the vicinity thereof beyond the surrounding pressure). The quantity of the aerosol can be increased as a result. The aforementioned twelfth embodiment describes the angle of slope α of the upper sloped surface region 270 relative to the center axis of the nozzle hole 115 (see FIG. 28) as being set to be, for example, no less than 20° and no more than 45°. However, providing the protrusion 274 ameliorates a situation where it is difficult to suck the liquid due to insufficient negative pressure due to the protrusion 274 not being provided, and makes it possible to suck the liquid, even in the case where the angle of slope α is greater than 45° (50°, 60°, or the like). Furthermore, providing the protrusion 274 makes it possible to increase the quantity of the aerosol even in the case where the angle of slope α is set to 45° or less (this is useful in cases of low compressor capabilities).

Fifteenth Embodiment

Figure 35:
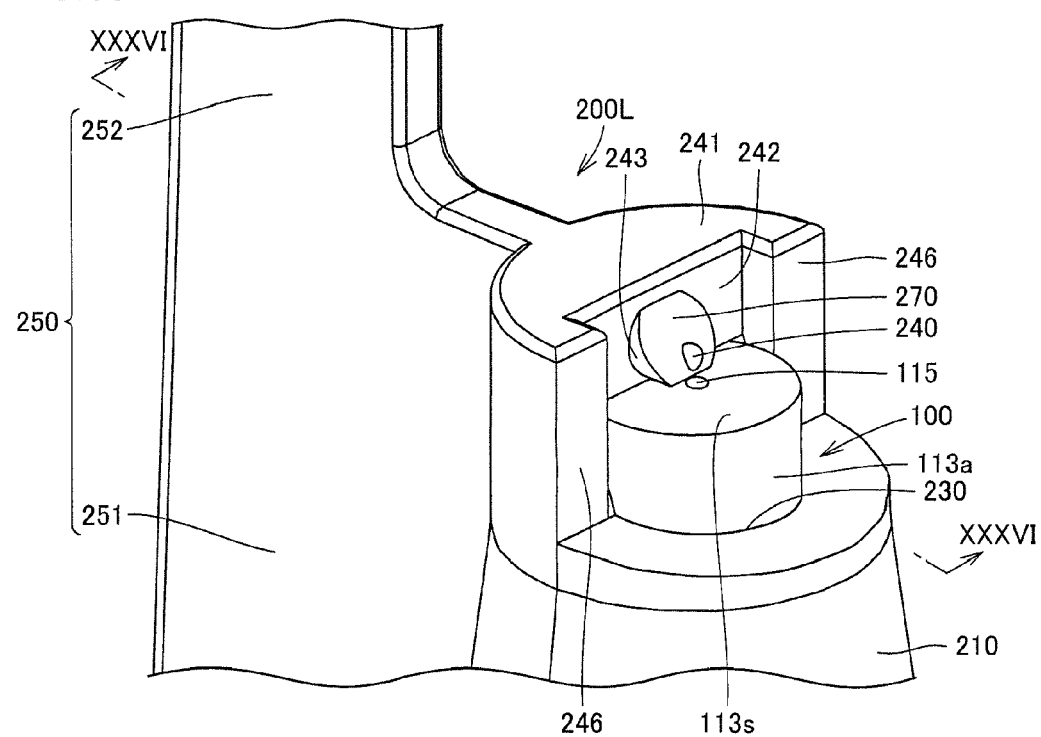
FIG. 35 is a perspective view illustrating an atomizing area and the vicinity thereof in a nebulizer kit according to a fifteenth embodiment.
Figure 36:
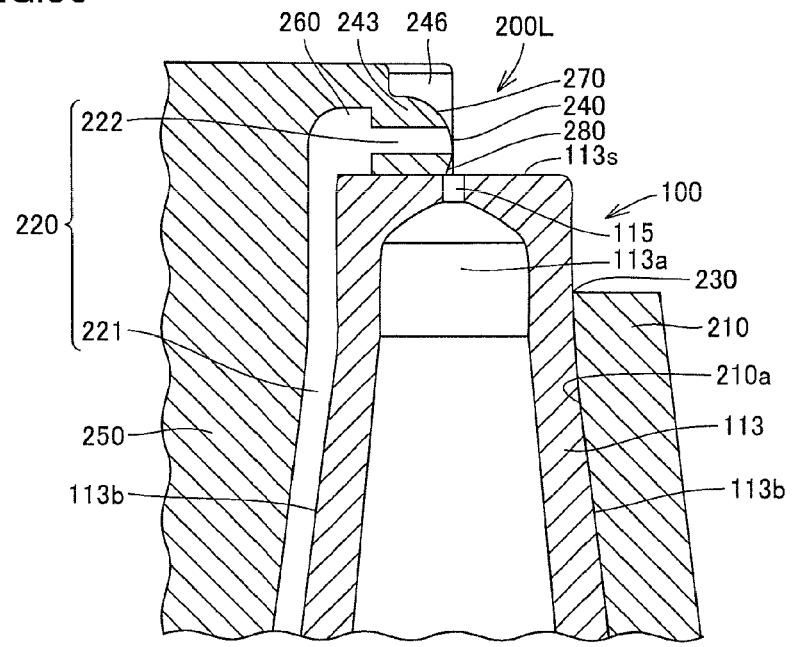
FIG. 36 is a cross-sectional view taken along a XXXVI-XXXVI line shown in FIG. 35.

The present embodiment will be described with reference to FIGS. 35 and 36. FIG. 35 is a perspective view illustrating an atomizing area and the vicinity thereof in a nebulizer kit according to the present embodiment. FIG. 36 is a cross-sectional view taken along a XXXVI-XXXVI line shown in FIG. 35.

The nebulizer kit according to the present embodiment includes a suction channel formation member 200L instead of the suction channel formation member 200J (see FIG. 30 and so on) according to the aforementioned thirteenth embodiment. The configuration of the suction channel formation member 200L described hereinafter can also be applied in the first embodiment (see FIG. 10), the second embodiment (see FIG. 15), the third embodiment (see FIG. 16), the fourth embodiment (see FIG. 17), the fifth embodiment (see FIG. 18), the sixth embodiment (see FIG. 19), the seventh embodiment (see FIG. 20), the eighth embodiment (see FIG. 21), and the ninth embodiment (see FIG. 22).

As shown in FIGS. 35 and 36, in the suction channel formation member 200L, a leading end surface of the liquid suction port formation member 243 is formed so as to curve in a convex shape. Both the upper sloped surface region 270 and the lower sloped surface region 280 are curved in a convex shape as well.

Because the upper sloped surface region 270 and the lower sloped surface region 280 are formed having a convex shape, the liquid W discharged from the liquid suction port 240 easily spreads across a wide range, and easily forms a liquid film. The liquid W that has formed a liquid film is more easily broken up by the compressed air expelled from the nozzle hole 115, and thus an improvement in the misting efficiency is achieved.

Sixteenth Embodiment

Figure 37:
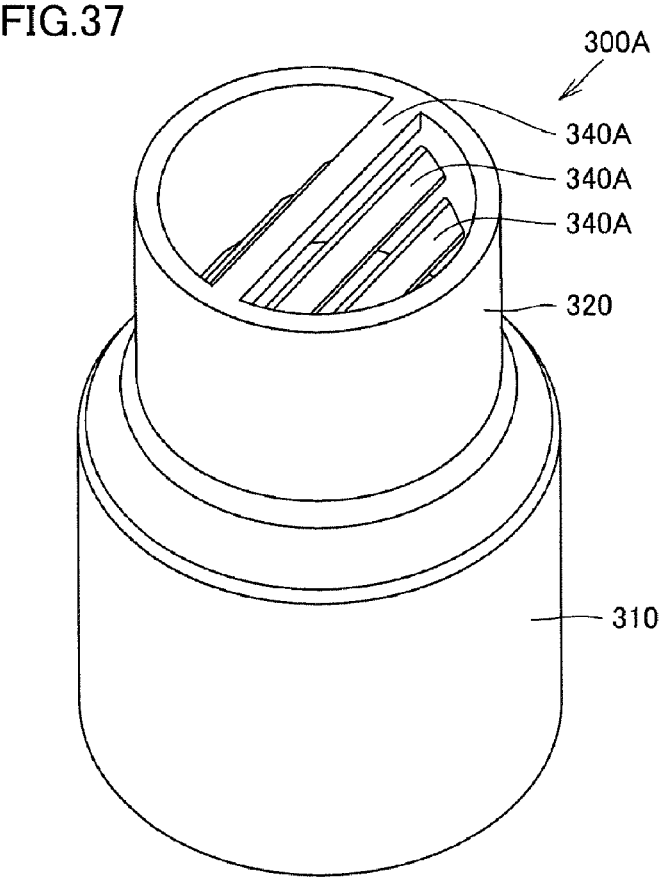
FIG. 37 is a perspective view illustrating a particle segregating portion used in a nebulizer kit according to a sixteenth embodiment.
Figure 38:
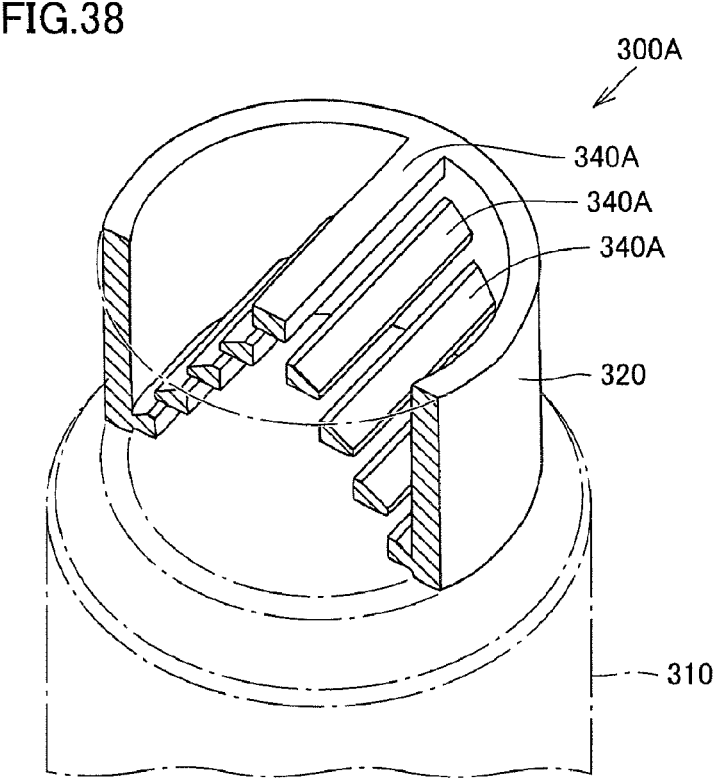

The present embodiment will be described with reference to FIGS. 37 and 38. A nebulizer kit according to the present embodiment includes a particle segregating portion 300A instead of the particle segregating portion 300 (see FIG. 3 and so on) according to the aforementioned first embodiment. The configuration of the particle segregating portion 300A described hereinafter can also be applied in the aforementioned second to fifteenth embodiments.

Figure 14:
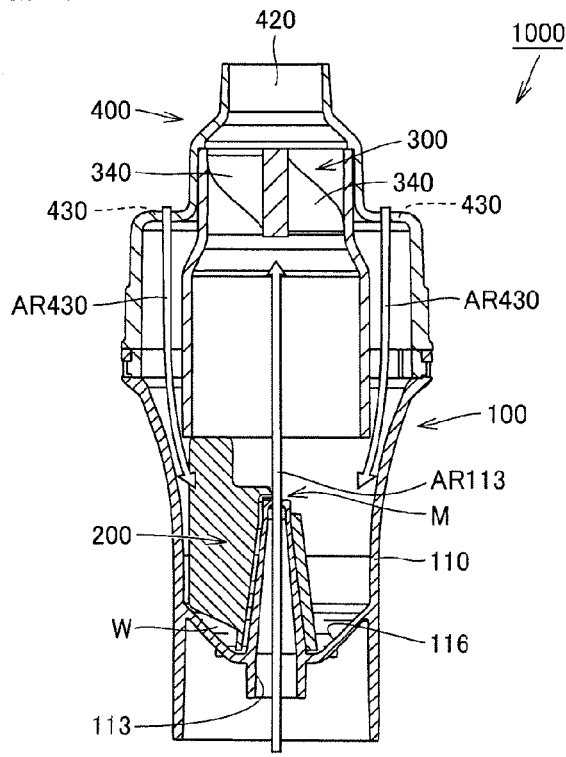
FIG. 14 is a cross-sectional view illustrating a state of the nebulizer kit as a whole when aerosol is produced by the nebulizer kit according to the first embodiment.

In the particle segregating portion 300 according to the aforementioned first embodiment, the four blade portions 340 occupy a space between the atomizing area M (see FIG. 14 and so on) and the aerosol discharge port 420 (see FIG. 14 and so on) in a fan shape. The particle segregating portion 300A according to the present embodiment includes a plurality of blade portions 340A. The plurality of blade portions 340A are formed in slat shapes, and are disposed in an essentially triangular shape, when viewed as a cross-section, progressing from the side on which the lower cylinder portion 310 is located toward the upper cylinder portion 320. The plurality of blade portions 340A are positioned so as to be parallel to each other (see FIG. 38). The plurality of blade portions 340A occupy a space between the atomizing area M and the aerosol discharge port 420 in a linear shape.

Even in the case where the particle segregating portion 300A is used, large (for example, 10 μm or greater) particles of the aerosol moving toward the aerosol discharge port 420 from the atomizing area M adhere to the surfaces of the blade portions 340A. Aerosol having desired particle diameters (for example, greater than or equal to 2 μm and less than 10 μm) segregated by the blade portions 340A is then discharged to the exterior through the aerosol discharge port 420 (see FIG. 3 and so on). The aerosol is then sucked into the nose or mouth of the user through the mouthpiece 500 (see FIG. 1).

Seventeenth Embodiment

Figure 39:
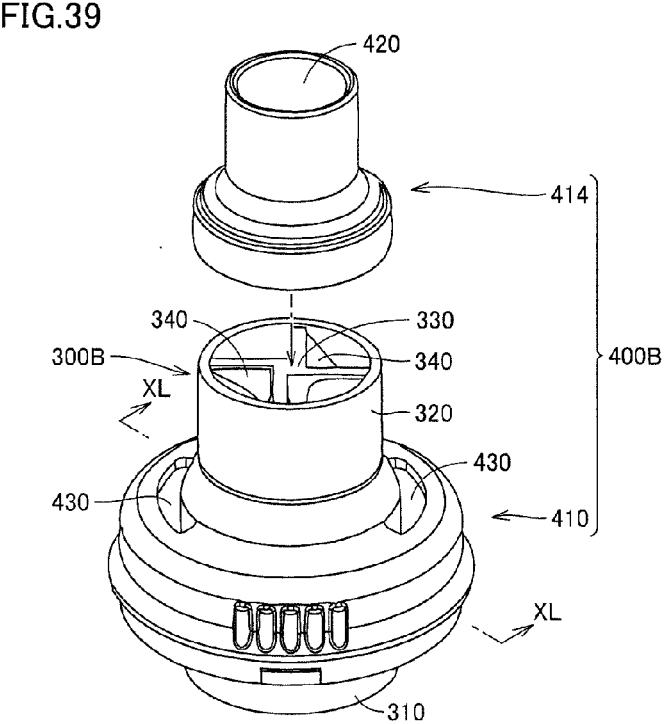
Figure 40:
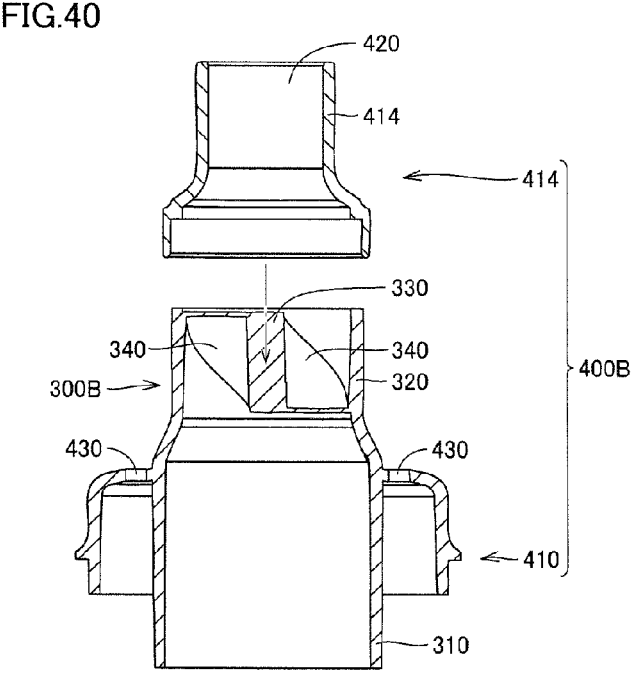

The present embodiment will be described with reference to FIGS. 39 and 40. A nebulizer kit according to the present embodiment includes a particle segregating portion 300B instead of the particle segregating portion 300 (see FIG. 3 and so on) according to the aforementioned first embodiment, and includes a flow channel formation member 400B instead of the flow channel formation member 400 (see FIG. 3 and so on). The configuration of the particle segregating portion 300B and the flow channel formation member 400B described hereinafter can also be applied in the aforementioned second to fifteenth embodiments.

In the present embodiment, the upper cylinder portion 414 and the lower cylinder portion 410 of the flow channel formation member 400B are configured as separate entities, and the particle segregating portion 300B is provided as an integral part of the lower cylinder portion 410 within the lower cylinder portion 410. The upper cylinder portion 414 is fitted into an upper end of the upper cylinder portion 320 in the particle segregating portion 300B.

Even in the case where the particle segregating portion 300B and the flow channel formation member 400B are used, large (for example, 10 μm or greater) particles of the aerosol moving toward the aerosol discharge port 420 from the atomizing area M (see FIG. 14 and so on) adhere to the surfaces of the blade portions 340. Aerosol having desired particle diameters (for example, greater than or equal to 2 μm and less than 10 μm) segregated by the blade portions 340 is then discharged to the exterior through the aerosol discharge port 420. The aerosol is then sucked into the nose or mouth of the user through the mouthpiece 500 (see FIG. 1).

Eighteenth Embodiment

Figure 41:
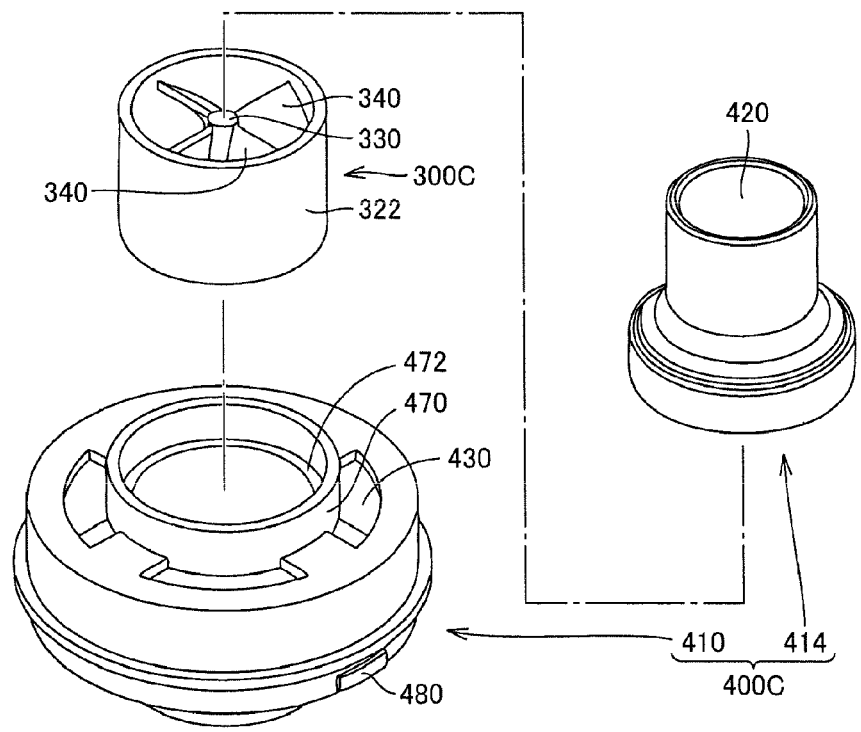

The present embodiment will be described with reference to FIG. 41. A nebulizer kit according to the present embodiment includes a particle segregating portion 300C instead of the particle segregating portion 300 (see FIG. 3 and so on) according to the aforementioned first embodiment, and includes a flow channel formation member 400C instead of the flow channel formation member 400 (see FIG. 3 and so on). The configuration of the particle segregating portion 300C and the flow channel formation member 400C described hereinafter can also be applied in the aforementioned second to fifteenth embodiments.

In the present embodiment, the upper cylinder portion 414 and the lower cylinder portion 410 of the flow channel formation member 400C are configured as separate entities. A cylindrical fixing portion 470 is provided in the lower cylinder portion 410. A step 472 is provided on an inner side of the cylindrical fixing portion 470. A cylindrical portion 322 of the particle segregating portion 300C is fitted inside the cylindrical fixing portion 470. The four blade portions 340 are provided on an inner side of the cylindrical portion 322. The particle segregating portion 300C is fixed to the flow channel formation member 400C by being sandwiched between the upper cylinder portion 414 and the lower cylinder portion 410.

Even in the case where the particle segregating portion 300C and the flow channel formation member 400C are used, large (for example, 10 μm or greater) particles of the aerosol moving toward the aerosol discharge port 420 from the atomizing area M (see FIG. 14 and so on) adhere to the surfaces of the blade portions 340. Aerosol having desired particle diameters (for example, greater than or equal to 2 μm and less than 10 μm) segregated by the blade portions 340 is then discharged to the exterior through the aerosol discharge port 420. The aerosol is then sucked into the nose or mouth of the user through the mouthpiece 500 (see FIG. 1).

Nineteenth Embodiment

Figure 42:
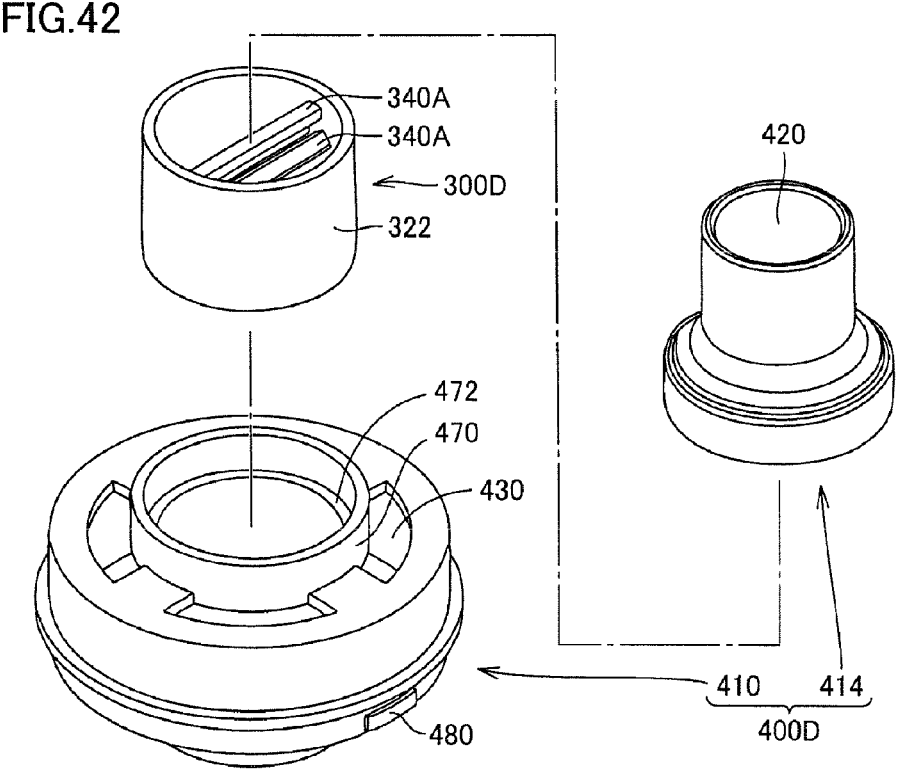

The present embodiment will be described with reference to FIG. 42. A nebulizer kit according to the present embodiment includes a particle segregating portion 300D instead of the particle segregating portion 300 (see FIG. 3 and so on) according to the aforementioned first embodiment, and includes a flow channel formation member 400D instead of the flow channel formation member 400 (see FIG. 3 and so on). The configuration of the particle segregating portion 300D and the flow channel formation member 400D described hereinafter can also be applied in the aforementioned second to fifteenth embodiments.

In the present embodiment, the upper cylinder portion 414 and the lower cylinder portion 410 of the flow channel formation member 400D are configured as separate entities. The cylindrical fixing portion 470 is provided in the lower cylinder portion 410. The step 472 is provided on an inner side of the cylindrical fixing portion 470. The cylindrical portion 322 of the particle segregating portion 300D is fitted inside the cylindrical fixing portion 470. The plurality of blade portions 340A are provided on an inner side of the cylindrical portion 322. The particle segregating portion 300D is fixed to the flow channel formation member 400D by being sandwiched between the upper cylinder portion 414 and the lower cylinder portion 410.

Even in the case where the particle segregating portion 300D and the flow channel formation member 400D are used, large (for example, 10 μm or greater) particles of the aerosol moving toward the aerosol discharge port 420 from the atomizing area M (see FIG. 14 and so on) adhere to the surfaces of the blade portions 340A. Aerosol having desired particle diameters (for example, greater than or equal to 2 μm and less than 10 μm) segregated by the blade portions 340A is then discharged to the exterior through the aerosol discharge port 420. The aerosol is then sucked into the nose or mouth of the user through the mouthpiece 500 (see FIG. 1).

Twentieth Embodiment

Figure 43:
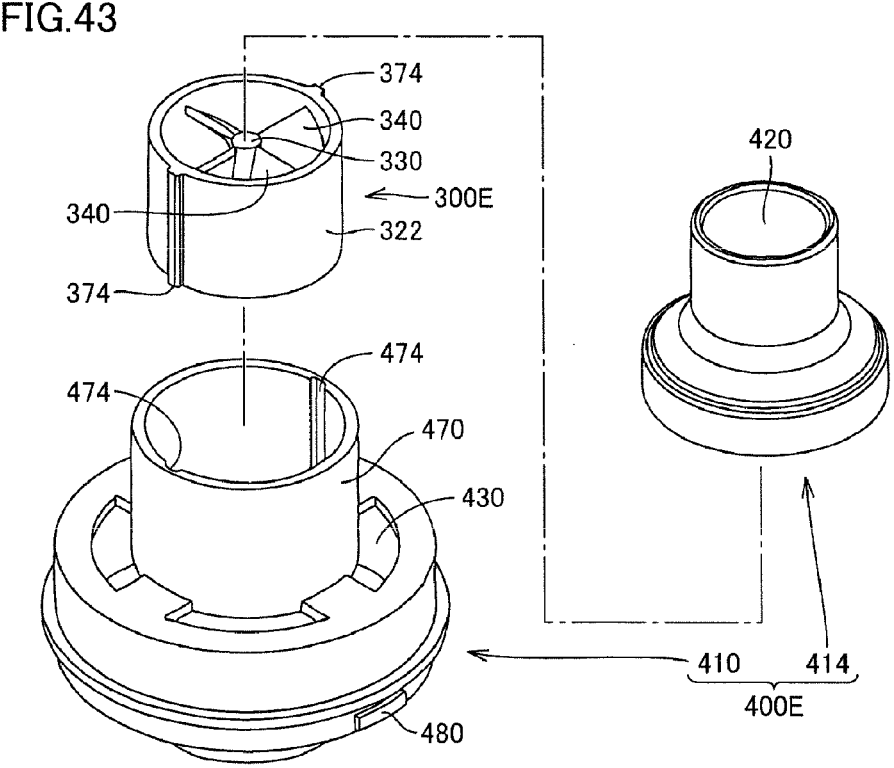

The present embodiment will be described with reference to FIG. 43. A nebulizer kit according to the present embodiment includes a particle segregating portion 300E instead of the particle segregating portion 300 (see FIG. 3 and so on) according to the aforementioned first embodiment, and includes a flow channel formation member 400E instead of the flow channel formation member 400 (see FIG. 3 and so on). The configuration of the particle segregating portion 300E and the flow channel formation member 400E described hereinafter can also be applied in the aforementioned second to fifteenth embodiments.

In the present embodiment, the upper cylinder portion 414 and the lower cylinder portion 410 of the flow channel formation member 400E are configured as separate entities. The cylindrical fixing portion 470 is provided in the lower cylinder portion 410. An interlocking recess 474 is provided on an inner side of the cylindrical fixing portion 470. The cylindrical portion 322 of the particle segregating portion 300E is fitted inside the cylindrical fixing portion 470. The four blade portions 340 are provided on an inner side of the cylindrical portion 322. An interlocking protrusion 374 is provided on an outer side of the cylindrical portion 322. The particle segregating portion 300E is fixed to the flow channel formation member 400E by being sandwiched between the upper cylinder portion 414 and the lower cylinder portion 410 with the interlocking protrusion 374 and the interlocking recess 474 interlocking with each other.

Even in the case where the particle segregating portion 300E and the flow channel formation member 400E are used, large (for example, 10 μm or greater) particles of the aerosol moving toward the aerosol discharge port 420 from the atomizing area M (see FIG. 14 and so on) adhere to the surfaces of the blade portions 340. Aerosol having desired particle diameters (for example, greater than or equal to 2 μm and less than 10 μm) segregated by the blade portions 340 are then discharged to the exterior through the aerosol discharge port 420. Movement of the particle segregating portion 300E in a rotation direction relative to the flow channel formation member 400E is limited, and thus aerosol having a particle size closer to a design value is discharged to the exterior. The aerosol is then sucked into the nose or mouth of the user through the mouthpiece 500 (see FIG. 1).

Twenty-first Embodiment

Figure 44:
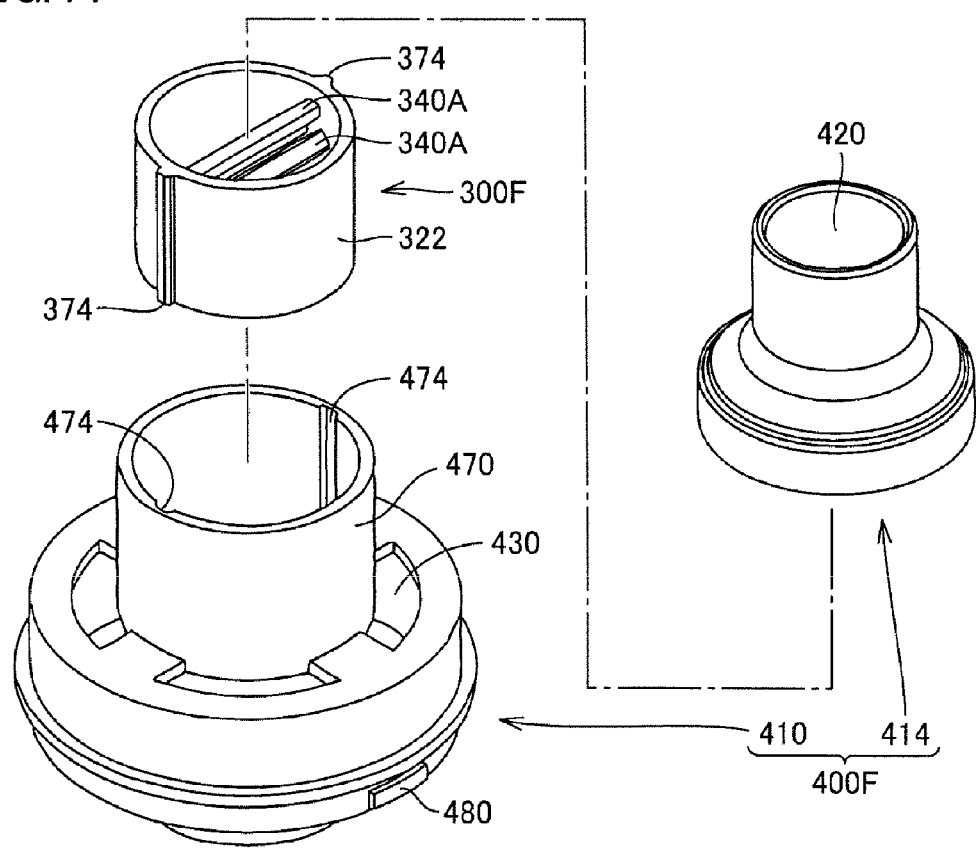

The present embodiment will be described with reference to FIG. 44. A nebulizer kit according to the present embodiment includes a particle segregating portion 300F instead of the particle segregating portion 300 (see FIG. 3 and so on) according to the aforementioned first embodiment, and includes a flow channel formation member 400F instead of the flow channel formation member 400 (see FIG. 3 and so on). The configuration of the particle segregating portion 300F and the flow channel formation member 400F described hereinafter can also be applied in the aforementioned second to fifteenth embodiments.

In the present embodiment, the upper cylinder portion 414 and the lower cylinder portion 410 of the flow channel formation member 400F are configured as separate entities. The cylindrical fixing portion 470 is provided in the lower cylinder portion 410. The interlocking recess 474 is provided on an inner side of the cylindrical fixing portion 470. The cylindrical portion 322 of the particle segregating portion 300F is fitted inside the cylindrical fixing portion 470. The plurality of blade portions 340A are provided on an inner side of the cylindrical portion 322. The interlocking protrusion 374 is provided on an outer side of the cylindrical portion 322. The particle segregating portion 300F is fixed to the flow channel formation member 400F by being sandwiched between the upper cylinder portion 414 and the lower cylinder portion 410 with the interlocking protrusion 374 and the interlocking recess 474 interlocking with each other.

Even in the case where the particle segregating portion 300F and the flow channel formation member 400F are used, large (for example, 10 μm or greater) particles of the aerosol moving toward the aerosol discharge port 420 from the atomizing area M (see FIG. 14 and so on) adhere to the surfaces of the blade portions 340A. Aerosol having desired particle diameters (for example, greater than or equal to 2 μm and less than 10 μm) segregated by the blade portions 340A is then discharged to the exterior through the aerosol discharge port 420. Movement of the particle segregating portion 300F in a rotation direction relative to the flow channel formation member 400F is limited, and thus aerosol having a particle size closer to a design value is discharged to the exterior. The aerosol is then sucked into the nose or mouth of the user through the mouthpiece 500 (see FIG. 1).

Twenty-Second Embodiment

Figure 45:
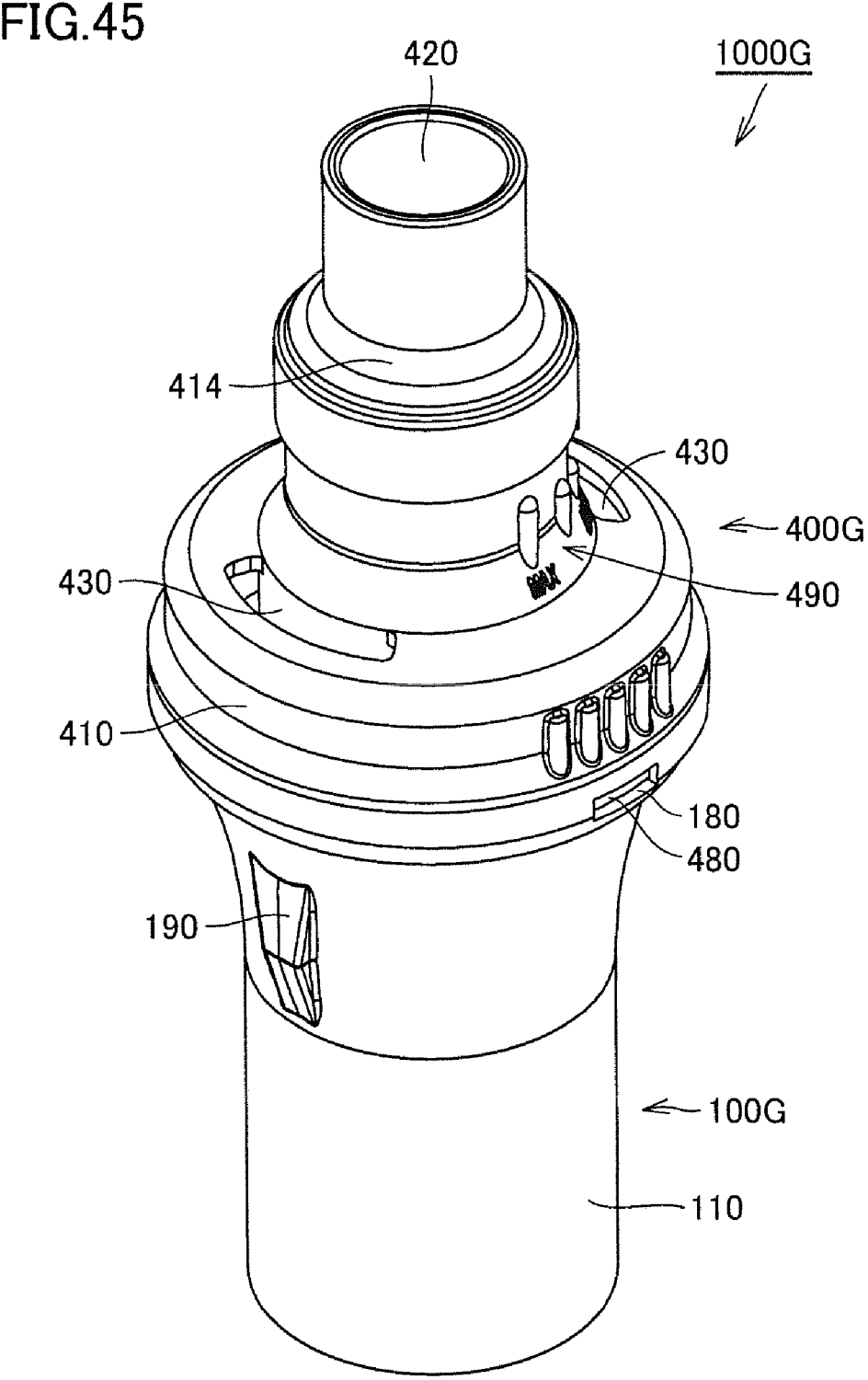

A nebulizer kit 1000G according to the present embodiment will be described with reference to FIGS. 45 to 54. FIG. 45 is perspective view illustrating the nebulizer kit 1000E FIG. 46 is an exploded perspective view illustrating the nebulizer kit 1000G.

Nebulizer Kit 1000G

Figure 46:
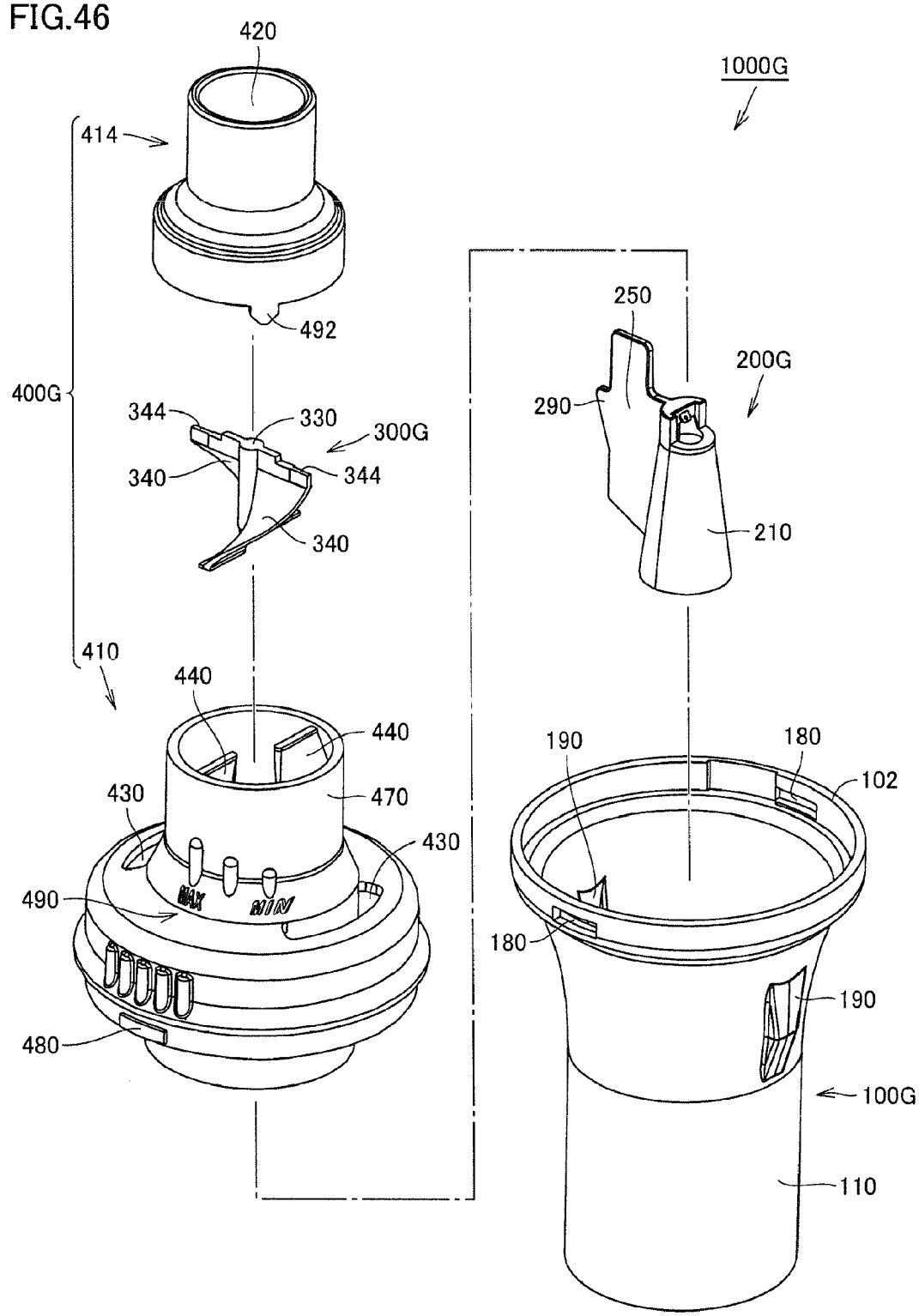

As shown in FIGS. 45 and 46, the nebulizer kit 1000G includes a case body 100G, the suction channel formation member 200G (see FIG. 46), a particle segregating portion 300G (see FIG. 46), and a flow channel formation member 400G.

Case Body 100G/Suction Channel Formation Member 200G

Figure 25:
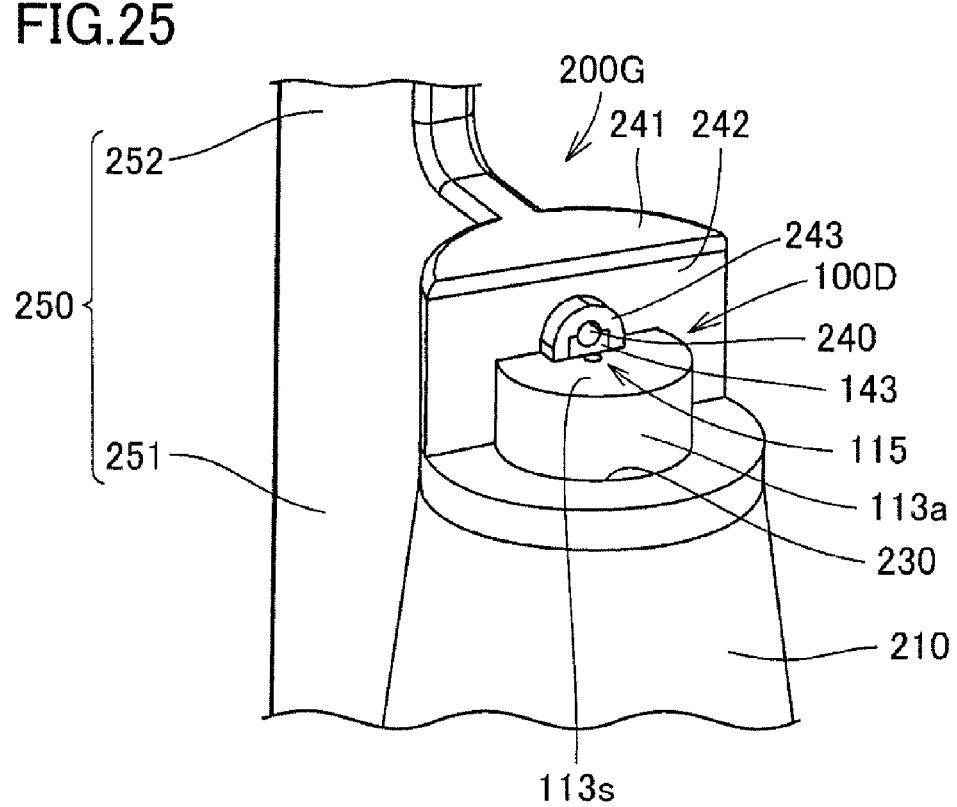
FIG. 25 is a perspective view illustrating an atomizing area and the vicinity thereof in a nebulizer kit according to an eleventh embodiment.
Figure 26:
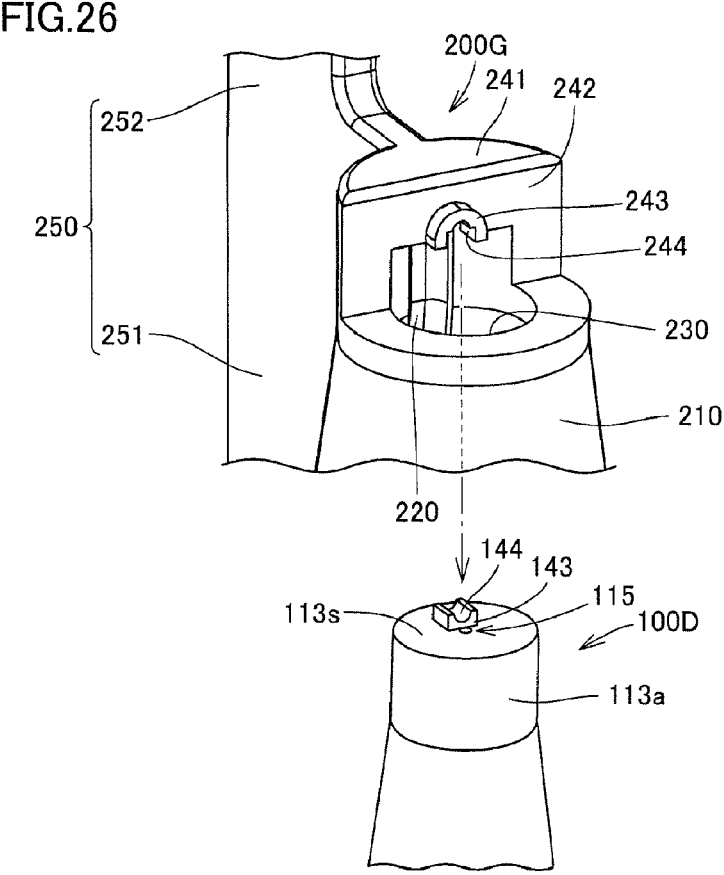
FIG. 26 is a perspective view illustrating a state when a suction channel formation member in the nebulizer kit according to the eleventh embodiment is attached to a case body (a compressed air introduction tube).
Figure 47:
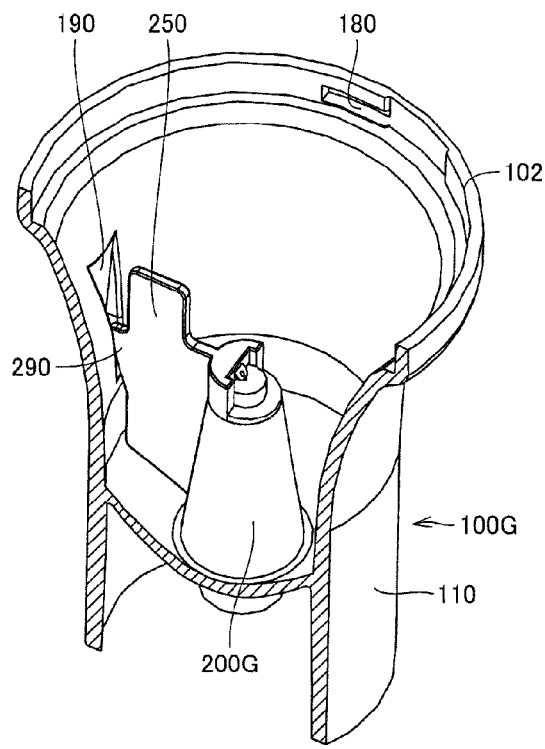

FIG. 47 is a cross-sectional perspective view illustrating the case body 100G and the suction channel formation member 200G. As shown in FIGS. 46 and 47, recesses 190 that are recessed from an inner side of the cylinder portion 110 toward an outer side of the cylinder portion 110 are provided in the cylinder portion 110 of the case body 100G. Aside from the recesses 190, the configurations of the case body 100A (see FIG. 20), 100B (see FIG. 21), 100C (see FIG. 22), and 100D (see FIG. 25) according to the aforementioned embodiments may be employed for the configuration of the case body 100G.

Figure 24:
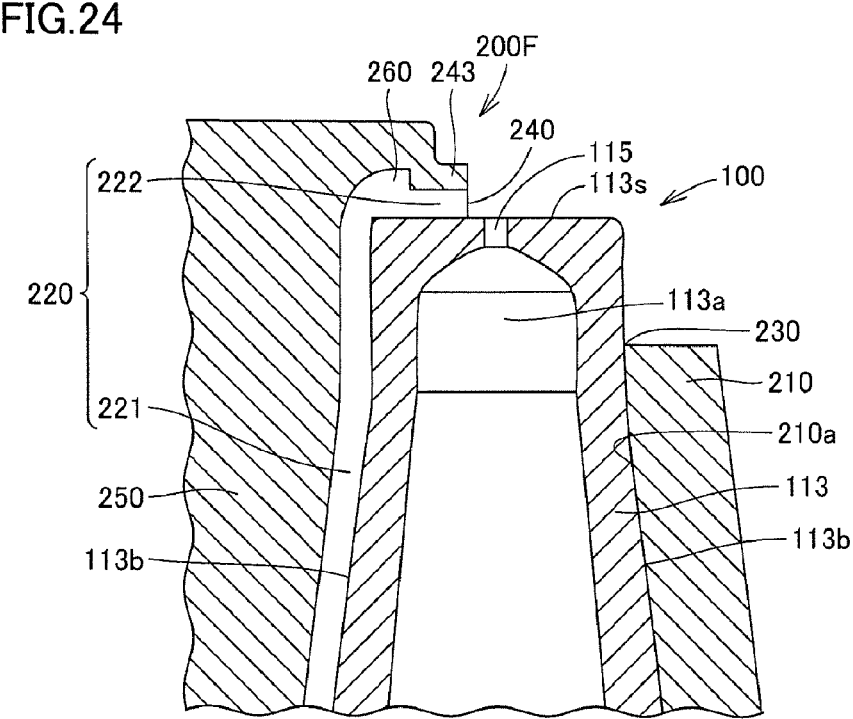
FIG. 24 is a cross-sectional view illustrating an atomizing area and the vicinity thereof in the nebulizer kit according to the tenth embodiment.

A protrusion 290 that protrudes away from the cylinder portion 210 may be provided in the plate-shaped gripping portion 250 of the suction channel formation member 200G. When the suction channel formation member 200G is disposed within the case body 100G, the protrusion 290 of the suction channel formation member 200G is fitted into an inner side of one of the recesses 190 of the case body 100G (see FIG. 47). The suction channel formation member 200G is thus fixed to the case body 100G. Aside from the protrusion 290, the configurations of the suction channel formation member 200 (see FIG. 3), 200A (see FIG. 15), 200B (see FIG. 16), 200C (see FIG. 17), 200D (see FIG. 18), 200E (see FIG. 19), 200F (see FIG. 24), and 200G (see FIG. 25) according to the aforementioned embodiments may be employed for the configuration of the suction channel formation member 200G.

Particle Segregating Portion 300G/Flow Channel Formation Member 400G

Referring again to FIG. 46, in the particle segregating portion 300G, two blade portions 340 are provided around the center shaft portion 330. In the particle segregating portion 300G, the two blade portions 340 are configured so as to be independent from the cylindrical fixing portion 470 (corresponding to the upper cylinder portion 320 indicated in FIGS. 39 and 40). The two blade portions 340 occupy a space between the atomizing area M and the aerosol discharge port 420 in a fan shape. Thin plate portions 344 that extend upward are provided in the upper ends of the blade portions 340. In the present embodiment, the orientation of the blade portions 340 relative to the atomizing area M (see FIGS. 11, 32, and so on) is adjusted by rotating the blade portions 340.

Specifically, in the flow channel formation member 400G, the upper cylinder portion 414 and the lower cylinder portion 410 are separate entities that are fixed to each other. The cylindrical fixing portion 470 is provided in the lower cylinder portion 410, extending upward. Two blade portions 440 are provided on an inner side of the cylindrical fixing portion 470 (see also FIG. 50). The blade portions 440 are formed having the same shape as the blade portions 340. When the cylindrical fixing portion 470 is taken as corresponding to the upper cylinder portion 320 (see FIGS. 39 and 40) in the particle segregating portion 300G, the blade portions 440 are positioned on an inner side of the upper cylinder portion 320 (toward an end of the particle segregating portion). A scale 490 is provided on an outer side of the cylindrical fixing portion 470.

Figure 48:
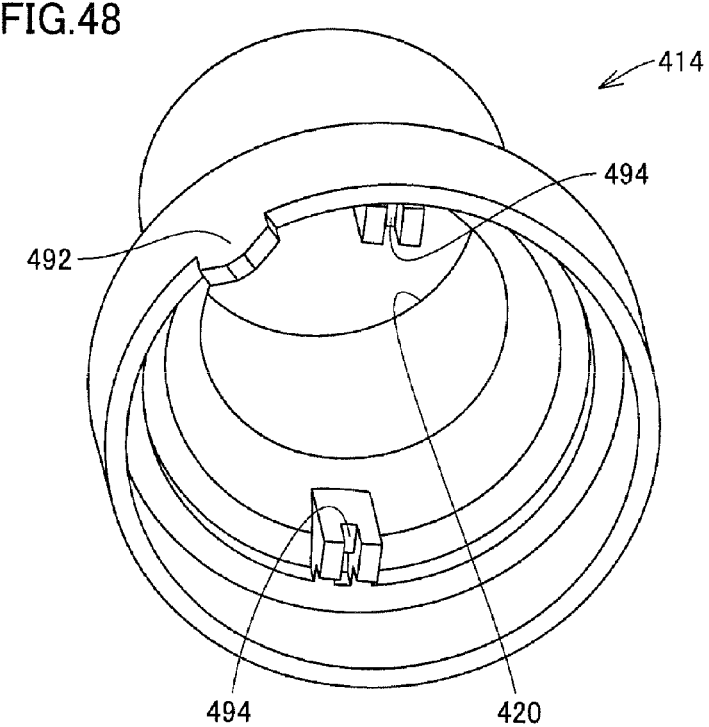

FIG. 48 is a perspective view illustrating the upper cylinder portion 414 of the flow channel formation member 400G Attachment recesses 494 are provided on an inner side of the upper cylinder portion 414. The attachment recesses 494 correspond to the shape of the thin plate portions 344 (see FIG. 46) in the particle segregating portion 300G (see FIG. 46). An indicator portion 492 that corresponds to the scale 490 is provided extending downward from the lower end of the upper cylinder portion 414 (see also FIG. 46).

Figure 49:
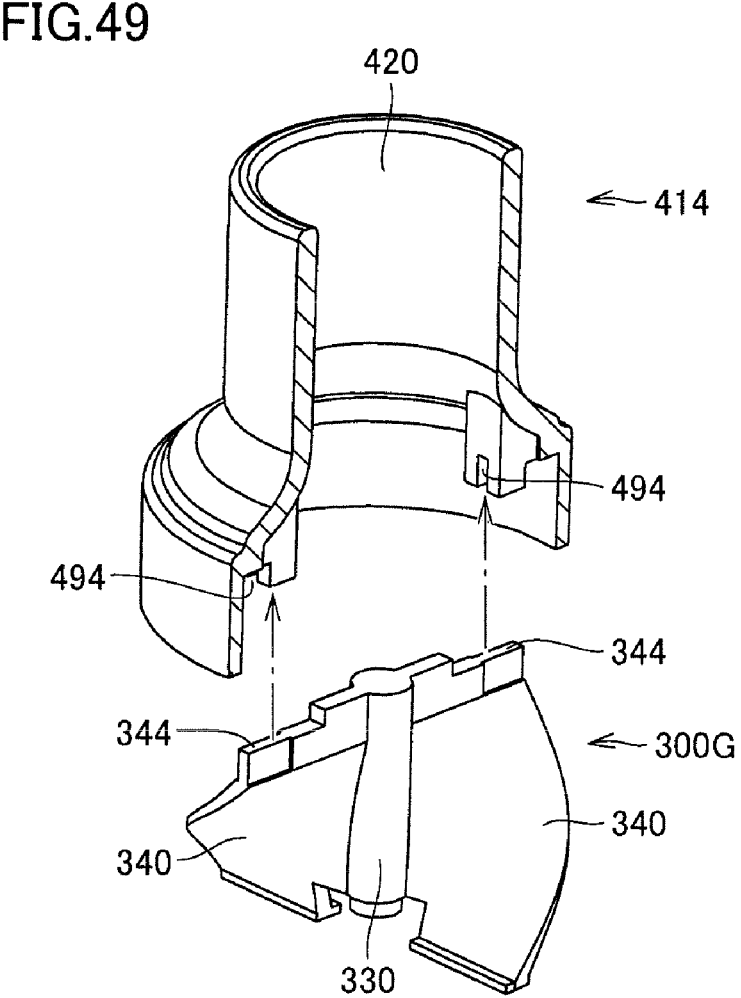

FIG. 49 is a cross-sectional perspective view illustrating a state in which the particle segregating portion 300G and the upper cylinder portion 414 of the flow channel formation member 400G are fixed to each other. The particle segregating portion 300G is configured to be removable from the flow channel formation member 400G, and is fixed to the flow channel formation member 400G by being sandwiched between the upper cylinder portion 414 and the lower cylinder portion 410 (see FIG. 46).

When the particle segregating portion 300G is fixed to the flow channel formation member 400G, the thin plate portions 344 of the particle segregating portion 300G interlock with inner sides of the attachment recesses 494 in the upper cylinder portion 414. Thus when the upper cylinder portion 414 rotates (see an arrow AR492 in FIG. 51), the upper cylinder portion 414 and the particle segregating portion 300G rotate integrally in the same direction.

Figure 50:
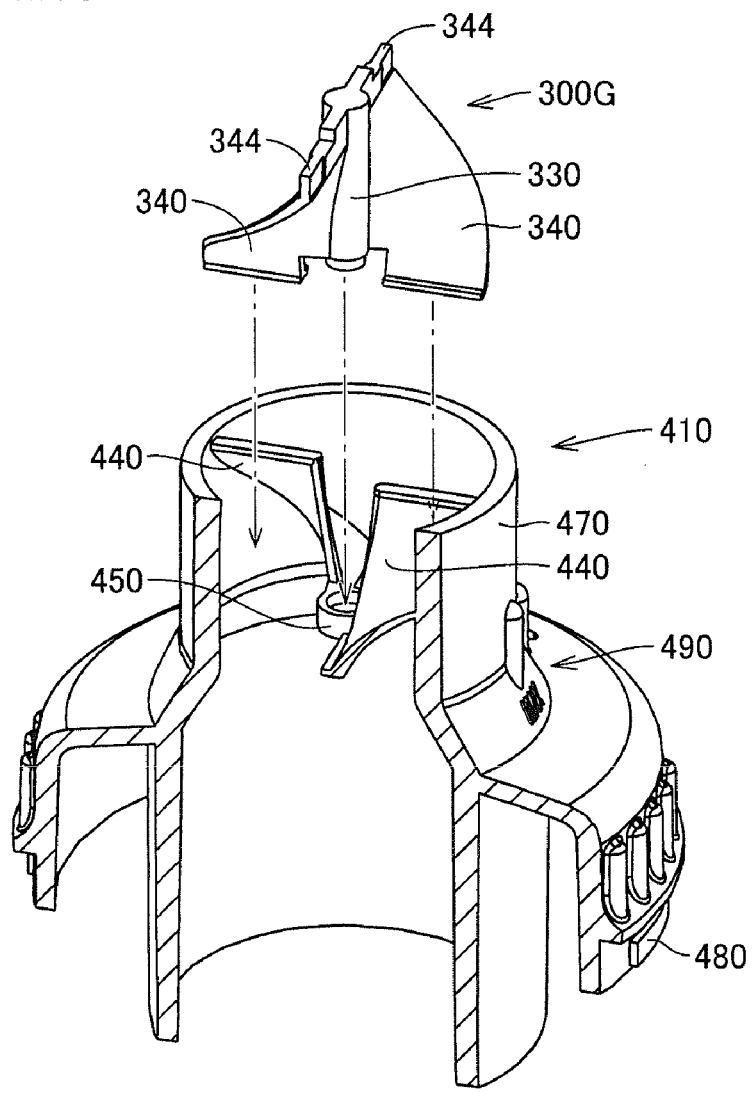

FIG. 50 is a cross-sectional perspective view illustrating a state in which the particle segregating portion 300G and the lower cylinder portion 410 of the flow channel formation member 400G are fixed to each other. As described above, the particle segregating portion 300G is fixed to the flow channel formation member 400G by being sandwiched between the upper cylinder portion 414 (see FIG. 46) and the lower cylinder portion 410. The blade portions 340 of the particle segregating portion 300G are configured to be removable from the lower cylinder portion 410 of the flow channel formation member 400G.

When the particle segregating portion 300G is fixed to the flow channel formation member 400G, a lower end of the center shaft portion 330 in the particle segregating portion 300G is fitted into a receiving portion 450 provided in the center of the cylindrical fixing portion 470. When the upper cylinder portion 414 (see FIG. 49 and so on) is rotated (see the arrow AR492 in FIG. 51), the particle segregating portion 300G rotates integrally with the upper cylinder portion 414 central to the receiving portion 450.

Operations of Nebulizer Kit 1000G

Figure 51:
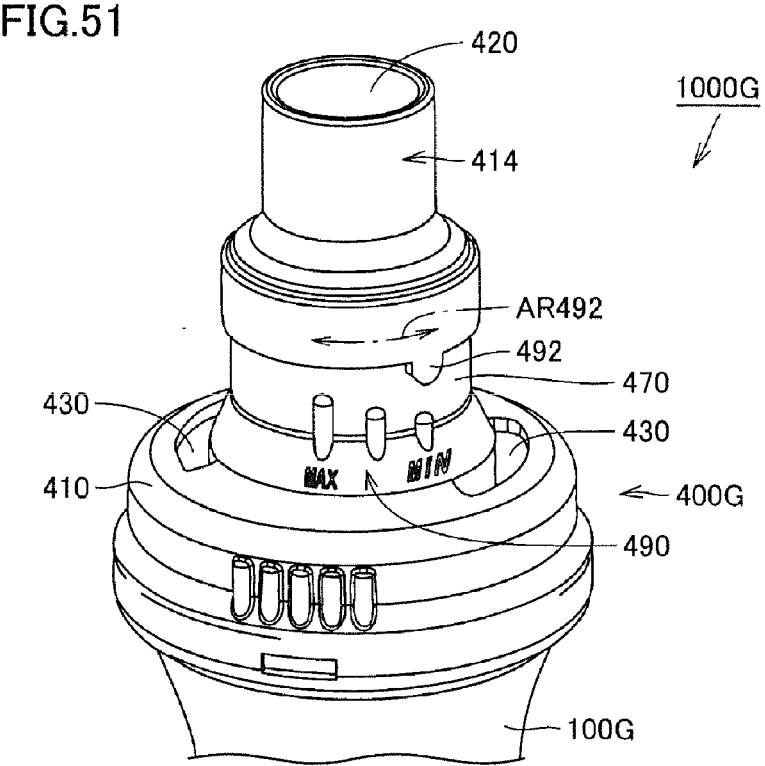

FIG. 51 is perspective view illustrating operations of the nebulizer kit 1000G In the nebulizer kit 1000G, the suction channel formation member 200G (see FIG. 47) is fixed to the case body 100G (see FIG. 47). The aerosol produced at the atomizing area M (see FIGS. 11, 32, and so on) moves toward the aerosol discharge port 420 with a predetermined directivity. In the nebulizer kit 1000G, the blade portions 340 (see FIG. 46 and so on) are positioned between the atomizing area M and the aerosol discharge port 420. The configuration is such that the orientation of the blade portions 340 relative to the atomizing area M can be adjusted.

Figure 52:
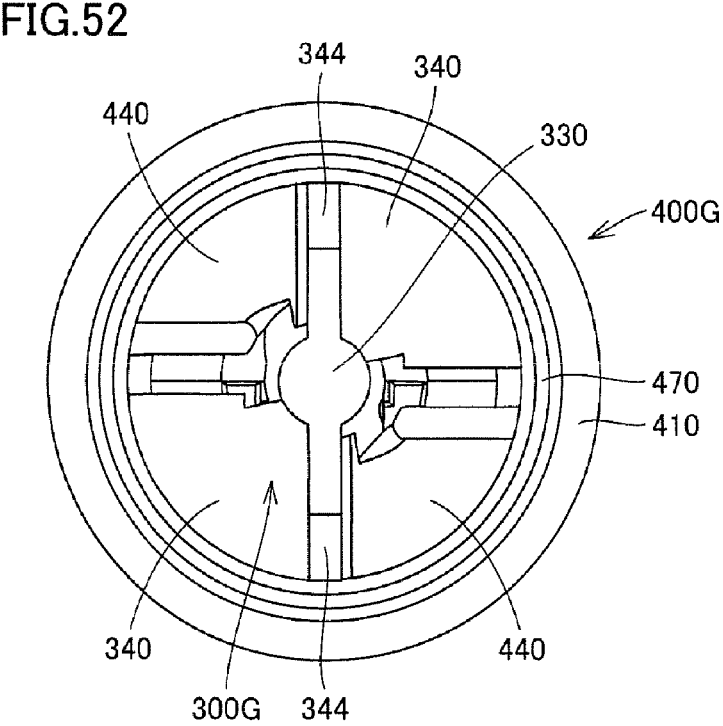

FIG. 52 is a first plan view illustrating the particle segregating portion 300G and the flow channel formation member 400G, looking down on the nebulizer kit 1000G from the aerosol discharge port 420. In FIG. 52, the indicator portion 492 of the upper cylinder portion 414 is set to "MIN" in the scale 490 (see FIG. 51).

In the state shown in FIG. 52, an aerosol channel formed between the atomizing area M and the aerosol discharge port 420 is almost completely occupied by the blade portions 340 and the blade portions 440. Almost all of large particles of the aerosol moving toward the aerosol discharge port 420 from the atomizing area M adhere to the surfaces of the blade portions 340 and the blade portions 440.

Figure 53:
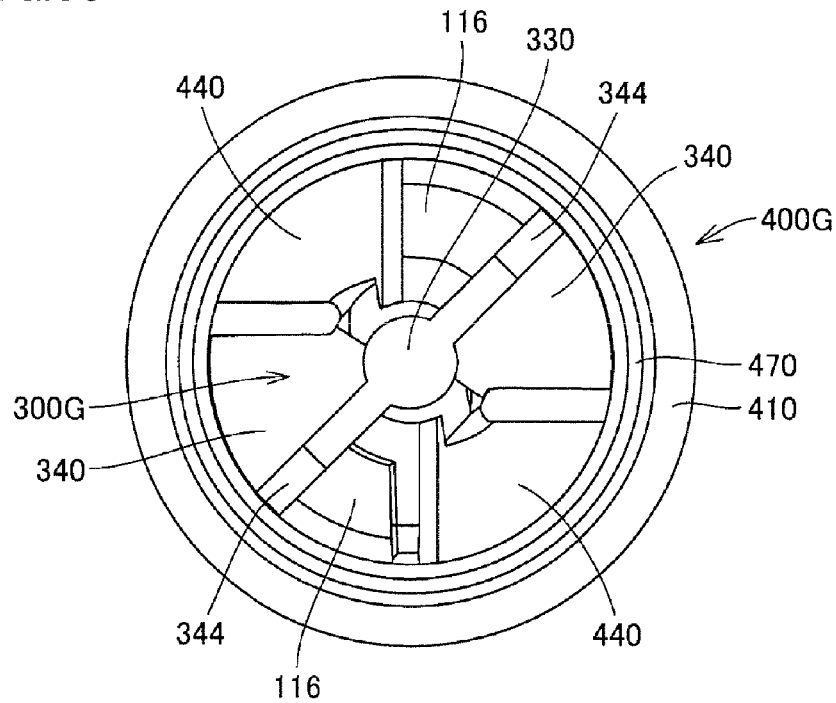

FIG. 53 is a second plan view illustrating the particle segregating portion 300G and the flow channel formation member 400G, looking down on the nebulizer kit 1000G from the aerosol discharge port 420. In FIG. 53, the indicator portion 492 of the upper cylinder portion 414 is set between "MIN" and "MAX" in the scale 490 (see FIG. 51). Compared to the blade portions 340 shown in FIG. 52, the blade portions 340 shown in FIG. 53 have been rotated clockwise by a predetermined angle as a result of the upper cylinder portion 414 rotating.

In the state shown in FIG. 53, the blade portions 340 are partially located underneath the blade portions 440. The aerosol channel formed between the atomizing area M and the aerosol discharge port 420 is slightly occupied by the blade portions 340 and the blade portions 440 (that is, the liquid reservoir portion 116 is partially exposed). Large particles of the aerosol moving toward the aerosol discharge port 420 from the atomizing area M can therefore also pass between the blade portions 340 and the blade portions 440 and be discharged to the exterior from the aerosol discharge port 420.

FIG. 54 is a third plan view illustrating the particle segregating portion 300G and the flow channel formation member 400G, looking down on the nebulizer kit 1000G from the aerosol discharge port 420. In FIG. 54, the indicator portion 492 of the upper cylinder portion 414 is set to "MAX" in the scale 490 (see FIG. 51). Compared to the blade portions 340 shown in FIG. 53, the blade portions 340 shown in FIG. 54 have been further rotated clockwise by a predetermined angle as a result of the upper cylinder portion 414 rotating.

In the state shown in FIG. 54, the blade portions 340 are almost entirely located underneath the blade portions 440. The aerosol channel formed between the atomizing area M and the aerosol discharge port 420 is thus almost completely unoccupied by the blade portions 340. Large particles of the aerosol moving toward the aerosol discharge port 420 from the atomizing area M can therefore also pass between the blade portions 340 and the blade portions 440 and be discharged to the exterior from the aerosol discharge port 420.

Actions and Effects

The orientation of the blade portions 340 relative to the atomizing area M is adjusted by rotating the blade portions 340. The width of the aerosol channel formed between the atomizing area M and the aerosol discharge port 420 (that is, the percentage of the channel occupied by the blade portions 340) increases or decreases when the blade portions 340 rotate. The size of the aerosol particles discharged from the aerosol discharge port 420 depends on the width of the aerosol channel formed between the atomizing area M and the aerosol discharge port 420. Therefore, according to the nebulizer kit 1000G, aerosol having a particle size that is optimal for water, a saline solution, a drug solution for treating a disease in the respiratory system or the like, or a vaccine administered to a user can be obtained.

Meanwhile, as shown in FIG. 50, the flow channel formation member 400G tapers so that the inner diameter thereof decreases as the member progresses from the bottom (an area toward the atomizing area M) toward the cylindrical fixing portion 470 (the aerosol discharge port 420). The blade portions 440 and the blade portions 340 can thus effectively segregate particles.

Twenty-Third Embodiment

The present embodiment will be described with reference to FIGS. 55 and 56. A nebulizer kit according to the present embodiment includes a particle segregating portion 300H instead of the particle segregating portion 300G (see FIG. 46 and so on) according to the aforementioned twenty-second embodiment, and includes a flow channel formation member 400H instead of the flow channel formation member 400G (see FIG. 46 and so on).

The particle segregating portion 300H according to the present embodiment includes a plurality of blade portions 340A on an inner side of the cylindrical portion 322. The plurality of blade portions 340A are formed in slat shapes, and are disposed in an essentially triangular shape when viewed as a cross-section. The plurality of blade portions 340A are positioned so as to be parallel to each other (see FIG. 56). The plurality of blade portions 340A occupy a space between the atomizing area M and the aerosol discharge port 420 in a linear shape.

The thin plate portions 344 that are fitted into the attachment recesses 494 of the upper cylinder portion 414 (see FIG. 46) are provided in an upper end of the cylindrical portion 322. The interlocking protrusion 374 that is fitted into the interlocking recess 474 of the cylindrical fixing portion 470 is provided in the outer surface of the cylindrical portion 322.

The aerosol produced at the atomizing area M (see FIGS. 11, 32, and so on) moves toward the aerosol discharge port 420 (see FIG. 46) with a predetermined directivity in this present embodiment as well. The blade portions 340A are positioned between the atomizing area M and the aerosol discharge port 420. The configuration is such that the orientation of the blade portions 340A relative to the atomizing area M can be adjusted.

The orientation of the blade portions 340A relative to the atomizing area M is adjusted by rotating the blade portions 340A. The width of the aerosol channel formed between the atomizing area M and the aerosol discharge port 420 (that is, the percentage of the channel occupied by the blade portions 340A) increases or decreases when the blade portions 340A rotate. The size of the aerosol particles discharged from the aerosol discharge port 420 depends on the width of the aerosol channel formed between the atomizing area M and the aerosol discharge port 420. Therefore, according to the nebulizer kit of the present embodiment as well, aerosol having a particle size that is optimal for water, a saline solution, a drug solution for treating a disease in the respiratory system or the like, or a vaccine administered to a user can be obtained.

Twenty-Fourth Embodiment

The present embodiment will be described with reference to FIG. 57. A nebulizer kit according to the present embodiment includes a particle segregating portion 300J instead of the particle segregating portion 300G (see FIG. 46 and so on) according to the aforementioned twenty-second embodiment, and includes a flow channel formation member 400J instead of the flow channel formation member 400G (see FIG. 46 and so on).

In the particle segregating portion 300J, a connection portion 376, a gripping portion 378, and a projection 388 are provided in the outer circumferential surface of the cylindrical portion 322. The connection portion 376 projects in the normal direction relative to the cylindrical portion 322. The gripping portion 378 is provided so as to hang downward from a leading end of the connection portion 376 in the direction in which the connection portion 376 projects. The shape of the connection portion 376 corresponds to the shape of a notched portion 476 provided in the flow channel formation member 400J, which will be mentioned later. The shape of the projection 388 corresponds to the shape of a recessed groove 478 provided in the flow channel formation member 400J, which will be mentioned later. The projection 388 is fitted into the recessed groove 478.

In the flow channel formation member 400J, the notched portion 476 is provided in the cylindrical fixing portion 470. The notched portion 476 is provided parallel to the direction of the cylinder axis of the cylindrical fixing portion 470. The connection portion 376 of the particle segregating portion 300J is fitted into the notched portion 476. The particle segregating portion 300J can be kept at a predetermined height as a result of the notched portion 476 and the connection portion 376 interlocking with each other. A scale 496 is provided on an outer surface of the cylindrical fixing portion 470, in the vicinity of the notched portion 476.

The aerosol produced at the atomizing area M (see FIGS. 11, 32, and so on) moves toward the aerosol discharge port 420 (see FIG. 57) with a predetermined directivity in this present embodiment as well. The blade portions 340 are positioned between the atomizing area M and the aerosol discharge port 420. The configuration is such that the position of the blade portions 340 relative to the atomizing area M can be adjusted.

A gap between the blade portions 340 and the atomizing area M is increased or decreased by changing the position of the particle segregating portion 300J relative to the flow channel formation member 400J using the gripping portion 378. The size of the aerosol particles discharged from the aerosol discharge port 420 also depends on the gap between the blade portions 340 and the atomizing area M. Therefore, according to the nebulizer kit of the present embodiment as well, aerosol having a particle size that is optimal for water, a saline solution, a drug solution for treating a disease in the respiratory system or the like, or a vaccine administered to a user can be obtained.

Twenty-Fifth Embodiment

The present embodiment will be described with reference to FIGS. 58 and 59. A nebulizer kit according to the present embodiment includes a particle segregating portion 300K instead of the particle segregating portion 300G (see FIG. 46 and so on) according to the aforementioned twenty-second embodiment, and includes a flow channel formation member 400K instead of the flow channel formation member 400G (see FIG. 46 and so on).

In the particle segregating portion 300K, a projection 377 and the interlocking protrusion 374 are provided in the outer circumferential surface of the cylindrical portion 322. The shape of the projection 377 corresponds to the shape of an engagement long-hole 427 provided in the flow channel formation member 400K (upper cylinder portion 414). The shape of the interlocking protrusion 374 corresponds to the shape of the interlocking recess 474 provided in the flow channel formation member 400K (lower cylinder portion 410). The interlocking protrusion 374 is fitted into the interlocking recess 474.

As shown in FIG. 59, a single blade portion 440 is provided on the inner side of the cylindrical portion 322, and a slat-shaped shaft portion 329 is supported by the blade portion 440. The slat-shaped shaft portion 329 is disposed following the cylinder axis of the cylindrical portion 322.

The particle segregating portion 300K includes three blade portions 340B. A fitting hole 349 is provided in each of the three blade portions 340B. The three blade portions 340B are fitted onto the slat-shaped shaft portion 329 in order using the fitting holes 349. It is preferable that the fitting holes 349 are configured so as to engage with the slat-shaped shaft portion 329 using friction.

The aerosol produced at the atomizing area M (see FIGS. 11, 32, and so on) moves toward the aerosol discharge port 420 (see FIG. 58) with a predetermined directivity in this present embodiment as well. The blade portions 340B are positioned between the atomizing area M and the aerosol discharge port 420. The configuration is such that the orientations of the blade portions 340B relative to the atomizing area M can be adjusted.

The orientations of the blade portions 340B relative to the atomizing area M are adjusted by rotating the blade portions 340B. The width of the aerosol channel formed between the atomizing area M and the aerosol discharge port 420 (that is, the percentage of the channel occupied by the blade portions 340B) increases or decreases when the blade portions 340B rotate. The size of the aerosol particles discharged from the aerosol discharge port 420 depends on the width of the aerosol channel formed between the atomizing area M and the aerosol discharge port 420. Therefore, according to the nebulizer kit of the present embodiment as well, aerosol having a particle size that is optimal for water, a saline solution, a drug solution for treating a disease in the respiratory system or the like, or a vaccine administered to a user can be obtained.

The three blade portions 340B can be attached at independent angles relative to the slat-shaped shaft portion 329. Because the percentage of the channel occupied by the blade portions 340B can be adjusted over a smaller range, the nebulizer kit according to the present embodiment is highly convenient for obtaining aerosol having an optimal particle size. Furthermore, because the blade portions 340B can be easily removed from the cylindrical portion 322, the nebulizer kit according to the present embodiment is also highly convenient in terms of cleaning.

Although several embodiments of the present invention have been described thus far, it should be noted that the embodiments disclosed above are to be understood as being in all ways exemplary and in no way limiting. The technical scope of the present invention is defined by the scope of the appended claims, and all changes that fall within the same essential spirit as the scope of the claims are intended to be included therein as well.

REFERENCE SIGNS LIST 100, 100A, 100B, 100C, 100D, 100G, 900 case body
102, 230, 235, 924a opening
110, 210, 322 cylindrical portion
113, 913 compressed air introduction tube
113a, 913a upper tip area
113b outer circumferential surface
113s leading end surface
115, 915 nozzle hole
115c center line
116, 916 liquid reservoir portion
143 platform
144, 190 indentation
180 interlocking hole
200, 200A, 200B, 200C, 200D, 200E, 200F, 200G, 200H, 200J, 200K, 200L suction channel formation member
210a inner circumferential surface
220 suction channel formation portion
221, 222 suction channel
232 upper end surface
240 liquid suction port
241, 246 expanded portion
242 end surface
243 liquid suction port formation member
243T leading end area
244 inner side
250 plate-shaped gripping portion
251 plate portion
252, 274, 290 protrusion
260 liquid collection portion
270 upper sloped surface region
272 sloped surface
280 lower sloped surface region
300, 300A, 300B, 300C, 300D, 300E, 300F, 300G, 300H, 300J, 300K particle segregating portion
310, 410 lower cylinder portion
320, 414 upper cylinder portion
329 slat-shaped shaft portion
330 center shaft portion
340, 340A, 340B, 440 blade portion
344 thin plate portion
349 fitting hole
374, 480 interlocking protrusion
376 connection portion
377, 388 projection
378 gripping portion
400, 400B, 400C, 400D, 400E, 400F, 400G, 400H, 400J, 400K, 930 flow channel formation member
412 central cylinder portion
420, 932 aerosol discharge port
427 engagement long-hole
430 outside air introduction port
450 receiving portion
470 cylindrical fixing portion
472 step
474 interlocking recess
476 notched portion
478 recessed groove
490, 496 scale
492 indicator portion
494 attachment recess
500 mouthpiece
510 main body
511 compressed air expulsion port
512 tube
902 upper opening
920 atomizing area formation member
922 baffle portion
923 baffle support portion
924 liquid suction tube formation area
925 projection
925T lower end
934 outside air introduction tube
1000, 1000G, 1000Z nebulizer kit 2000 nebulizer
AR113, AR220, AR272, AR430, AR492, AR913, AR915, AR922, AR932, AR934 arrow
M atomizing area
R115 exit region
W liquid
W1 droplet
W2 aerosol

The invention claimed is:

1. A nebulizer kit comprising:
a case body, having an open upper end, and including a compressed air introduction tube, extending upward, into which compressed air is introduced and in an upper end portion of which a nozzle hole that expels the compressed air is formed, and further including a liquid reservoir portion provided surrounding an outer circumferential surface of the compressed air introduction tube at a bottom area of the compressed air introduction tube;
a suction channel formation member that forms a suction channel that sucks a liquid held in the liquid reservoir portion toward the upper end portion of the compressed air introduction tube and forms an atomizing area in an exit region of the nozzle hole provided in the compressed air introduction tube by covering the outer circumferential surface of the compressed air introduction tube to supply the liquid directly into the flow of compressed air; and
a flow channel formation member, including an aerosol discharge port that discharges an aerosol formed at the atomizing area to the exterior, that is attached to the case body so as to cover an upper opening of the case body,
wherein the suction channel includes:
a first suction channel that extends upward along the outer circumferential surface of the compressed air introduction tube; and
a second suction channel that extends from the first suction channel toward the nozzle hole at a leading end area of the compressed air introduction tube and has a liquid suction port that expels the liquid that has been sucked up,
a particle segregating portion that has a blade portion and that segregates particles of the aerosol using the blade portion and discharges the aerosol of a desired particle size to the exterior is provided between the atomizing area and the aerosol discharge port;
the suction channel formation member is fixed to the case body;
an orientation or a position of the blade portion relative to the atomizing area can be adjusted; and
the position of the blade portion relative to the atomizing area is adjusted by moving the blade portion so as to increase or decrease a gap between the blade portion and the atomizing area.

2. The nebulizer kit according to claim 1, wherein the orientation of the blade portion relative to the atomizing area is adjusted by rotating the blade portion.

3. The nebulizer kit according to claim 2, wherein the blade portion is configured to occupy a space between the atomizing area and the aerosol discharge port in a fan shape.

4. The nebulizer kit according to claim 2, wherein the blade portion is configured to occupy a space between the atomizing area and the aerosol discharge port in a linear shape.

5. The nebulizer kit according to claim 1, wherein the blade portion is configured to be removable from the flow channel formation member.

6. The nebulizer kit according to claim 1, wherein the blade portion is provided toward an end of the particle segregating portion in the lengthwise direction of the particle segregating portion.

7. The nebulizer kit according to claim 1, wherein the particle segregating portion is configured to be removable from the flow channel formation member.

8. The nebulizer kit according to claim 1, wherein the flow channel formation member includes an upper cylinder portion having the aerosol discharge port; and
the blade portion and the particle segregating portion are assembled with the upper cylinder portion.

9. The nebulizer kit according to claim 1, wherein a channel through which the aerosol flows between the atomizing area and the aerosol discharge port is configured to have a smaller inner diameter in an area near the aerosol discharge port than in an area near the atomizing area.

10. A nebulizer comprising:
a main body including a compressor that discharges compressed air;
a compressed air tube portion through which the compressed air discharged by the compressor is introduced; and
the nebulizer kit according to claim 1, to which one end of the compressed air tube portion is attached and that produces an aerosol.

* * * * *